US012773206B2

(12) United States Patent
Phillips et al.

(10) Patent No.: US 12,773,206 B2
(45) Date of Patent: *Oct. 27, 2026

(54) MAGNET-ASSISTED SUTURE GRASPER COMPRISING A SUTURE RETRIEVAL NEEDLE, A GRASPER MAGNET, AND A SPRING

(71) Applicant: APPLIED MEDICAL TECHNOLOGY, INC.

(72) Inventors: Grant Wesley Phillips, Richfield, OH (US); Steven Alfred Soeder, North Royalton, OH (US); George J. Picha, Brecksville, OH (US)

(73) Assignee: APPLIED MEDICAL TECHNOLOGY, INC., Brecksville, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/129,988

(22) PCT Filed: Nov. 18, 2022

(86) PCT No.: PCT/US2022/050475

§ 371 (c)(1),
(2) Date: May 14, 2025

(87) PCT Pub. No.: WO2024/107206

PCT Pub. Date: May 23, 2024

(65) Prior Publication Data

US 2026/0102154 A1 Apr. 16, 2026

(51) Int. Cl.
*A61B 17/04* (2006.01)
*A61B 17/00* (2006.01)

(52) U.S. Cl.
CPC *A61B 17/0469* (2013.01); *A61B 2017/00876* (2013.01)

(58) Field of Classification Search
CPC ............ A61B 17/0469; A61B 17/0482; A61B 2017/047; A61B 2017/0472;
(Continued)

(56) References Cited

U.S. PATENT DOCUMENTS 1,212,870 A 1/1917 Zolper
3,762,418 A 10/1973 Wasson
(Continued)

FOREIGN PATENT DOCUMENTS

EP 778004 B1 3/2003
EP 3017778 A1 * 5/2016 ............. A61B 17/52
(Continued)

OTHER PUBLICATIONS

Owens, J., "How Does a Clicky Pen Work?" You Tube, pp. 1-8 (2022), available at https://www.youtube.com/watch?v=Zv5Qa2kGL04, last accessed Sep. 29, 2022.
(Continued)

*Primary Examiner* — Katherine H Schwiker
*Assistant Examiner* — Zehra Jaffri
(74) *Attorney, Agent, or Firm* — EVENTIDE LAW LLC

(57) ABSTRACT

A magnet-assisted suture grasper for grasping a magnetic suture is provided. The magnet-assisted suture grasper includes a suture retrieval needle, a retriever body, a grasper member, a grasper magnet, and a spring. Translation of the retriever body within a needle lumen of the suture retrieval needle in a first direction causes the grasper member to move from a first position to a second position, thereby exposing the grasper magnet from the needle lumen and allowing contact between the grasper magnet and a magnetic suture attracted thereto. Translation of the retriever body within the needle lumen in a second direction opposite the first direction causes the grasper member to move from the second position to the first position, thereby sequestering the
(Continued)

grasper magnet and grasping the magnetic suture within the needle lumen. The spring allows the grasper member to move reversibly upon pushing contact.

22 Claims, 31 Drawing Sheets

(58) Field of Classification Search
CPC . A61B 17/0483; A61B 17/29; A61B 17/0485; A61B 17/0491; A61B 2017/00876; A61B 17/28
See application file for complete search history.

(56) References Cited

U.S. PATENT DOCUMENTS 4,115,015 A 9/1978 Torii
4,266,881 A 5/1981 Rubens
4,540,300 A 9/1985 Midorikawa
4,560,298 A 12/1985 Oki et al.
D292,297 S 10/1987 Bingham
4,711,592 A 12/1987 Gregory
4,759,650 A 7/1988 Granoff
4,969,764 A 11/1990 Gregory
4,986,682 A 1/1991 Lu
5,022,773 A 6/1991 Waldinger et al.
5,026,190 A 6/1991 Longarzo
D321,207 S 10/1991 Granoff
D321,718 S 11/1991 Ambasz
5,131,775 A 7/1992 Chen
5,152,626 A 10/1992 Eppler
5,174,814 A 12/1992 Burwell et al.
5,364,365 A 11/1994 Wortrich
5,501,692 A 3/1996 Riza
5,651,626 A 7/1997 Chen
5,653,716 A 8/1997 Malo et al.
5,722,981 A 3/1998 Stevens
5,756,941 A 5/1998 Snell
5,817,111 A 10/1998 Riza
5,824,009 A * 10/1998 Fukuda .............. A61B 17/0469 606/139
5,864,490 A 1/1999 Van Bost
5,928,250 A 7/1999 Koike et al.
5,997,204 A 12/1999 Ducrocq
6,159,224 A 12/2000 Yoon
6,213,661 B1 4/2001 Coon
6,318,921 B1 11/2001 Craine
D457,917 S 5/2002 Traut et al.
6,450,721 B1 9/2002 D'Amico et al.
6,547,470 B2 4/2003 Legg
6,551,304 B1 4/2003 Whalen et al.
6,719,765 B2 4/2004 Bonutti
D494,218 S 8/2004 Anand
D495,001 S 8/2004 Anand
6,830,402 B2 12/2004 Sunatori
6,981,812 B1 1/2006 Hsieh
D537,878 S 3/2007 Anand
D542,349 S 5/2007 Anand
7,226,229 B1 6/2007 Register
D548,788 S 8/2007 Anand
7,334,954 B1 2/2008 Rentz
D571,400 S 6/2008 Anand
D574,429 S 8/2008 Kusaba et al.
D591,136 S 4/2009 Cheldin
D616,497 S 5/2010 Shiina
7,887,212 B2 2/2011 Liu
7,948,648 B2 5/2011 Silverbrook et al.
7,969,587 B2 6/2011 Silverbrook
8,031,177 B2 10/2011 Lapstun et al.
8,087,841 B2 1/2012 Liu
8,094,325 B2 1/2012 Silverbrook
8,182,167 B2 5/2012 Liu
8,240,931 B1 8/2012 Collins
8,262,241 B2 9/2012 Liu
8,267,947 B2 9/2012 Pantages et al.
8,287,204 B2 10/2012 Silverbrook et al.
8,297,868 B2 10/2012 Underwood et al.
8,360,669 B2 1/2013 Underwood et al.
8,414,210 B2 4/2013 Silverbrook et al.
8,632,270 B2 1/2014 Liu
8,702,753 B2 4/2014 Mikkaichi et al.
D725,112 S 3/2015 Bo
9,351,721 B2 5/2016 Auerbach et al.
D758,988 S 6/2016 An et al.
9,474,572 B2 10/2016 Lowry
9,770,238 B2 9/2017 Bonutti
10,245,021 B2 4/2019 Phillips et al.
10,299,786 B2 5/2019 Levine et al.
10,343,445 B2 7/2019 Wu
10,503,284 B1 12/2019 Chang et al.
10,960,705 B1 3/2021 Yu
10,974,540 B1 4/2021 Yu
11,241,904 B2 2/2022 Yu
11,672,530 B2 6/2023 Williams et al.
11,723,655 B2 8/2023 Phillips et al.
11,839,373 B2 12/2023 Phillips et al.
12,114,854 B2 10/2024 Phillips et al.
2003/0139752 A1 7/2003 Pasricha et al.
2003/0216613 A1 11/2003 Suzuki et al.
2004/0116963 A1 6/2004 Lattouf
2005/0154403 A1 7/2005 Sauer et al.
2006/0069398 A1 3/2006 Suzuki et al.
2007/0118153 A1 5/2007 Funamura et al.
2008/0154286 A1 6/2008 Abbott et al.
2008/0188877 A1 * 8/2008 Hickingbotham .......................... A61B 17/3211 606/162
2008/0243148 A1 10/2008 Mikkaichi et al.
2008/0269783 A1 10/2008 Griffith
2009/0224561 A1 9/2009 Jackson, III
2009/0318958 A1 12/2009 Ochiai
2010/0280530 A1 11/2010 Hashiba
2011/0015653 A1 1/2011 Bogart et al.
2011/0112555 A1 5/2011 Overes et al.
2011/0118757 A1 5/2011 Pierce
2011/0144666 A1 6/2011 Egle et al.
2011/0245850 A1 10/2011 Van Der Burg et al.
2012/0277766 A1 11/2012 Ferree
2013/0074849 A1 3/2013 Rousseau et al.
2013/0317291 A1 11/2013 Yamamoto
2015/0038976 A1 2/2015 Roschak et al.
2015/0039027 A1 2/2015 Broom et al.
2015/0100071 A1 4/2015 Phillips et al.
2015/0327850 A1 11/2015 Kostrzewski
2016/0324517 A1 11/2016 Liu
2017/0049439 A1 2/2017 Keyser et al.
2018/0049733 A1 2/2018 Zhao et al.
2018/0296201 A1 10/2018 Holsten et al.
2019/0076141 A1 3/2019 Liu
2019/0133591 A1 5/2019 Dobashi et al.
2020/0214695 A1 7/2020 Liu
2020/0360017 A1 11/2020 Liu
2021/0045735 A1 2/2021 Nobles et al.
2021/0059667 A1 3/2021 Williams et al.
2022/0104802 A1 4/2022 Liu
2022/0104803 A1 4/2022 Desjardin et al.
2022/0125426 A1 4/2022 Khanicheh et al.
2023/0141192 A1 5/2023 Phillips et al.
2024/0057998 A1 2/2024 Phillips et al.

FOREIGN PATENT DOCUMENTS

JP 2006-25932 A 2/2006
JP 2010514467 A 5/2010
WO 2010129312 A2 11/2010
WO 2011025767 A1 3/2011
WO 2022245819 A1 11/2022
WO 2022245822 A1 11/2022

OTHER PUBLICATIONS

Medacta International, "FastShuttle Suture Passer System Product Catalog," pp. 1-8 (2019), available at https://media.medacta.com/

(56) References Cited

OTHER PUBLICATIONS media/pc-99116sm180-rev-00.pdf, last accessed Sep. 29, 2022.
Imhoff, J., "Performing Incision-Less Hernia Repair for Kids," Michigan Health, pp. 1-5 (Feb. 17, 2020), available at https://labblog.uofmhealth.org/industry-dx/performing-incision-less-hernia-repairs-for-kids, last accessed Feb. 16, 2022.
Johnson, K.N., et al., "Ultrasound-Guided Pediatric Inguinal Hernia Repair," Journal of Pediatric Surgery, vol. 56, pp. 1240-1245 (epublished Mar. 11, 2021).
Young, R., "Rethinking the Simple Suture Passer," Orthopedics This Week, RRY Publications, pp. 1-8 (Apr. 29, 2016), available at https://ryortho.com/2016/04/rethinking-the-simple-suture-passer/, last accessed Apr. 25, 2022.
Orthomed, Inc., "Suture Passer with Crochet Hook," pp. 1-2 (2022), available at https://www.orthomedinc.com/surgical-instruments/suture-passer-with-crochet-hook, last accessed Sep. 29, 2022.
Mediflex Surgical Products, "5mm Curved Maryland Dissector with Cross Serrations," pp. 1-4 (2022), available at https://mediflex.com/products/5mm-curved-maryland-dissector, last accessed Sep. 29, 2022.
Coopersurgical, Inc., "Carter-Thomason CloseSure System—Port Site Closure," pp. 1-2 (2022), available at https://www.coopersurgical.com/detail/carter-thomason-closesure-system-port-site-closure/, last accessed Sep. 29, 2022.
Endoscopy Superstore, "Arthro-Pro Suture Manipulator Grasper," Manufacturer: Advanced Endoscopy Devices, pp. 1-2 (2022), available at https://www.endoscopysuperstore.com/arthro-pro-suture-manipulator-grasper.aspx#, last accessed Sep. 29, 2022.
Arthrex, Inc., "Back Grasper with SR Handle," pp. 1-3 (2022), available at https://www.arthrex.io/products/AR-12531SR, last accessed Sep. 29, 2022.
Arthrex, Inc., "CrabClaw," pp. 1-3 (2022), available at https://www.arthrex.com/shoulder/crabclaw, last accessed Sep. 29, 2022.
Smith & Nephew, "Meniscus Mender II," pp. 1-2 (2022), available at https://www.smith-nephew.com/professional/products/all-products/meniscus-mender-ii/, last accessed Sep. 29, 2022.
DePuy Synthes, "Chia Percpasser Suture Passer," pp. 1-5 (2021), available at https://www.jnjmedtech.com/en-US/product/chia-percpasserr-suture-passer, last accessed Sep. 29, 2022.
DePuy Synthes, "IDEAL Suture Shuttle," pp. 1-4 (2021), available at https://www.jnjmedtech.com/en-US/product/ideal-suture-shuttle, last accessed Sep. 29, 2022.
Arthrex, Inc., "SutureLasso," pp. 1-5 (2022), available at https://www.arthrex.com/shoulder/suturelassos, last accessed Sep. 29, 2022.
Medtronic, "Endoscopic Suturing Devices," pp. 1-3 (2022), available at https://www.medtronic.com/covidien/en-us/products/hand-instruments-ligation/endoscopic-suturing-devices.html, last accessed Sep. 29, 2022.
Zimmer Biomet, "SpeedSnare Surgical Suture Passer," pp. 1-7 (2022), available at https://www.zimmerbiomet.com/en/products-and-solutions/specialties/sports-medicine/speedsnare-surgical-suture-passer.html, last accessed Sep. 29, 2022.
Wikipedia, "Veress needle," pp. 1-3 (Apr. 3, 2022), available at https://en.wikipedia.org/wiki/Veress_needle, last accessed Sep. 29, 2022.
Coopersurgical, Inc., "Carter-Thomason II Port Site Closure System," pp. 1-2 (2022), available at https://www.coopersurgical.com/detail/carter-thomason-ii-port-site-closure-system/, last accessed Sep. 29, 2022.
Mediflex Surgical Products, "SafePass Suture Grasper," pp. 1-4 (2022), available at https://mediflex.com/products/safepass%E2%84%A2-suture-grasper-box-of-10-sterile, last accessed Sep. 29, 2022.
Zimmer Biomet, "Dragon Tongue Suture Passer," pp. 1-5 (2022), available at https://www.zimmerbiomet.com/en/products-and-solutions/specialties/sports-medicine/dragon-tongue-suture-passer.html, last accessed Sep. 29, 2022.
Medtronic, "Port-Site Closure Devices," pp. 1-4 (2022), available at https://www.medtronic.com/covidien/en-us/products/trocars-access/port-site-closure-devices.html; last accessed Sep. 20, 2022.
International Search Report and Written Opinion of PCT/US2022/050475, dated Mar. 14, 2023, pp. 1-7.
Notice of Reasons for Rejection, Japanese Pat. Appl. No. 2025-528587, issued Jul. 28, 2026, pp. 1-5 (including English translation).

* cited by examiner

MAGNET-ASSISTED SUTURE GRASPER COMPRISING A SUTURE RETRIEVAL NEEDLE, A GRASPER MAGNET, AND A SPRING

FIELD OF THE INVENTION

The invention relates to a magnet-assisted suture grasper for grasping a magnetic suture, and more particularly to a magnet-assisted suture grasper comprising a suture retrieval needle, a retriever body, a grasper member, a grasper magnet, and a spring.

BACKGROUND OF THE INVENTION

Suture passing is required in many surgical procedures. A suture passer is a surgical instrument which provides a means of delivery and/or retrieval of a suture through some bodily tissue. There are many existing instruments on the market which utilize a mechanical solution to secure a suture for passing.

Increasingly, minimally invasive techniques are being employed over open surgery due to reduction in risk, faster recovery time, and generally better cosmesis. Minimally invasive techniques typically make use of a scope and specialized tools that can be inserted through existing openings of a patient (e.g., via endoscope, colonoscope, etc.) or artificially created openings of the patient (e.g., via laparoscope, arthroscope, etc.) to gain access to the targeted intracorporeal working space.

Working with indirect visualization of surgical instruments through a scope presents a significant technical challenge to the use of suture passers for retrieval. Retrieving a suture using a typical suture passer requires precise positioning and careful manipulation of the suture passer to position one or more grasping elements of the suture passer around the suture. The suture passer must be held relatively steady in position while the grasping elements are closed about the suture, capturing the suture and holding it firmly so it can be retrieved. Skillful manipulation in this manner is hampered by the fact that most scopes employ a single camera and present a two-dimensional image to the suture passer operator and thus do not provide stereoscopic imaging. The lack of stereoscopic imaging hampers the operator's ability to perceive depth, which increases the level of difficulty associated with precisely positioning the grasping elements around the suture. While three-dimensional imaging systems exist, they are expensive and to date remain relatively rare in the field.

Most existing suture passer designs utilize a multi-arm design, where two or more arms are opened and brought around a suture, then closed around the suture to capture it. The arms may be separate, creating a pincer-style grasper with jaws to grasp a suture, or they may be connected, forming a snare-type grasper forming an eye through which a suture can be threaded.

Unfortunately, regardless of the arm design, these devices require precise positioning to get the jaws of the grasper around the suture, or to thread the suture through the eye of the snare before the suture can be captured. As noted, this is difficult under indirect visualization because camera systems for indirect visualization are typically non-stereoscopic. Without a three-dimensional image, a surgeon must rely on visual cues to judge the instrument position and depth, which makes it difficult to get the instrument positioned properly. Once the instrument is in position, the surgeon then needs to hold the instrument and the suture very steady while attempting to close the grasper around the suture. The long moment arm created by the length of the instrument magnifies even very minor movements, so that a small movement can bring the two components out of alignment. Failed attempts at grasping a suture can extend procedure times and lead to frustration in the operating room.

A magnetic U-stitch suturing device intended to address these difficulties has been disclosed in U.S. Pat. No. 10,245,021. The magnetic U-stitch suturing device is made of two hypodermic needles allowing one or more sutures, at the same time, and a retrieval probe to be advanced into a cavity, such as a stomach cavity, of a patient. The one or more sutures can be magnetic sutures, each including a suture magnet, as described in U.S. Pub. No. 2021/0059667. Both the suture and retrieval probe comprise magnets of opposite polarities on their leading ends. Thus, after the suture and retrieval probe are inside the stomach cavity, the suture and retrieval probe may mate and the suture may be transferred from one hypodermic needle to the other using magnetic attraction. In doing so, the suture forms a loop through the stomach. Once removed, this loop, having two ends that are positioned outside the patient's body, can be pulled tight in order to pull the stomach wall closer to the surface of the patient's body. With the stomach wall close to the surface of the patient's body, it is easier to insert a gastrostomy device.

Unfortunately, certain procedures, such as inguinal hernia repair through high ligation of the patent processus vaginalis, require passing of a suture in a space, e.g., a peritoneal cavity, that is not sufficiently large to permit advancement of the two hypodermic needles of the magnetic U-stitch suturing device simultaneously.

Other suture instruments and/or sutures including magnets also have been disclosed. For example, U.S. Pat. No. 10,299,786 discloses a suture insertion device utilizing small gauge needles for threading one or more sutures through subcutaneous tissue. The suture insertion device can include a magnetic capture mechanism for contacting a magnetically attractive strand in transverse alignment. U.S. Pat. Nos. 6,719,765 and 9,770,238 disclose instruments for passing a medical implement through tissue with magnetic forces. U.S. Pat. No. 6,551,304 discloses an apparatus and method for retrieving a remotely located device equipped with a magnetic coupler. U.S. Pat. No. 8,702,753 and U.S. Pub. No. 2008/0243148 disclose sutures to which magnetic anchors are attached. U.S. Pub. No. 2020/0360017 discloses a suturing apparatus in which a suture thread may be automatically passed between a needle and a transfer tube. The suturing apparatus can include electromagnetic coils to engage and release a suture from the system. U.S. Pub. No. 2020/0214695 discloses a suturing system including a forceps arm and a suture that may be magnetic to thus engage with each other. U.S. Pub. No. 2022/0104802 discloses a suturing system including a rod having a magnetic tube extending from an end thereof and a magnetic needle having an end attracted into the tube to magnetically engage therewith. U.S. Pub. No. 2021/0059667 discloses a magnetic suture that has a ferrule with a tapered region in which a knotted suture is provided and secured with an adhesive and a straight region in which a magnet is provided.

Applied Medical Technology, Inc.'s international application PCT/US2022/029627, filed May 17, 2022, discloses a magnet-assisted suture grasper including a suture retrieval needle, a retriever body, a grasper wire, a grasper arm, and a grasper magnet. Translation of the retriever body within a needle lumen of the suture retrieval needle in a first direction causes the grasper arm to move from a first position to a second position, thereby exposing the grasper magnet from the needle lumen and allowing contact between the grasper magnet and a magnetic suture attracted thereto. Translation of the retriever body within the needle lumen in a second direction opposite the first direction causes the grasper arm to move from the second position to the first position, thereby sequestering the grasper magnet and grasping the magnetic suture within the needle lumen.

Applied Medical Technology, Inc.'s international application PCT/US2022/029631, filed May 17, 2022, discloses a magnet-assisted suture grasper including a suture retrieval needle, a retriever body, a grasper arm, and a grasper magnet. Another magnet-assisted suture grasper including a handle, a stem, first and second grasper jaws, a grasper magnet, and an actuator body also is disclosed.

Improved suture passers that reduce the technical difficulty associated with capturing and retrieving sutures under indirect non-stereoscopic visualization are needed.

BRIEF SUMMARY OF THE INVENTION

A magnet-assisted suture grasper for grasping a magnetic suture is disclosed. The magnet-assisted suture grasper comprises: (a) a suture retrieval needle comprising a proximal end, a distal end, and a needle body extending therebetween, the needle body defining a needle body axis between the proximal and distal ends of the suture retrieval needle, the needle body having a proximal hole, a distal hole, and a needle lumen extending therebetween along the needle body axis; (b) a retriever body partially disposed within the needle lumen and translatable therein along the needle body axis; (c) a grasper member comprising an elongated proximal-to-intermediate portion and an enlarged distal terminus, the grasper member extending distally from the retriever body and being reversibly moveable with respect to the needle lumen between a first position and a second position, the enlarged distal terminus of the grasper member comprising a blunt distal end and extending partially from the distal hole of the needle body when the grasper member is in the first position and extending entirely beyond the distal hole of the needle body when the grasper member is in the second position; (d) a grasper magnet being disposed adjacent the elongated proximal-to-intermediate portion of the grasper member, the magnet-assisted suture grasper sequestering the grasper magnet within the needle lumen when the grasper member is in the first position and exposing the grasper magnet from the needle lumen when the grasper member is in the second position; and (e) a spring. The enlarged distal terminus of the grasper member extends further distally than the grasper magnet. Translation of the retriever body within the needle lumen in a first direction along the needle body axis causes the grasper member to move from the first position to the second position, thereby exposing the grasper magnet and allowing contact between the grasper magnet and a magnetic suture attracted thereto. Translation of the retriever body within the needle lumen in a second direction opposite the first direction along the needle body axis causes the grasper member to move from the second position to the first position, thereby sequestering the grasper magnet and grasping the magnetic suture within the needle lumen. The spring allows the grasper member to move reversibly further in the second direction from the first position upon pushing contact in the second direction at the enlarged distal terminus of the grasper member and returns the grasper member to the first position upon cessation of the pushing contact.

In some embodiments, the suture retrieval needle is a hypodermic needle. In some of these embodiments, the suture retrieval needle is straight, the needle body axis thereby being straight. In some of these embodiments, the suture retrieval needle is curved, the needle body axis thereby being curved.

In some embodiments, the suture retrieval needle has a sharp tip.

In some embodiments, the magnet-assisted suture grasper further comprises a proximal hub.

In some embodiments, the retriever body comprises a proximal end, a distal end, and a retriever tube extending therebetween; the retriever tube defines a retriever tube axis between the proximal and distal ends of the retriever body; the retriever tube has a proximal hole, a distal hole, and a retriever tube lumen extending therebetween along the retriever tube axis; and the proximal hole of the retriever tube is in fluid communication with the distal hole of the needle body through the retriever tube lumen and the needle lumen.

In some embodiments, the retriever body comprises a proximal end, a distal end, a distal hole, and a retriever body cavity extending within the retriever body from the distal hole of the retriever body.

In some embodiments, translation of the retriever body within the needle lumen is limited to a straight path as the translation of the retriever body causes the grasper member to move between the first and second positions.

In some embodiments, the grasper member is more flexible than the needle body.

In some embodiments, the elongated proximal-to-intermediate portion of the grasper member comprises a grasper wire having a proximal end and a distal end; the grasper wire is fixedly disposed within the retriever body and extends distally therefrom; the enlarged distal terminus extends distally from the distal end of the grasper wire and is reversibly moveable between the first position and the second position; and the grasper magnet is disposed adjacent the grasper wire.

In some of these embodiments, the enlarged distal terminus is reversibly moveable between the first position and the second position based on translation of the enlarged distal terminus from partially inside of the needle lumen to entirely outside of the needle lumen through the distal hole of the needle body; and the enlarged distal terminus has a size sufficiently small to allow contact between the grasper magnet and a suture magnet of a magnetic suture attracted thereto when the enlarged distal terminus is in the second position and to allow a suture of the magnetic suture to pass when the enlarged distal terminus is in the first position, and sufficiently large to block the suture magnet of the magnetic suture from exiting the needle lumen through the distal hole of the needle body when the enlarged distal terminus is in the first position.

Also in some of these embodiments, the grasper wire is formed from a round wire; and the enlarged distal terminus is fixedly attached to the grasper wire.

Also in some of these embodiments, the grasper wire and the enlarged distal terminus are formed from a flat wire having a rectangular cross-section; the enlarged distal terminus comprises opposing first and second portions of the flat wire that have been folded inwardly toward each other, thereby forming the enlarged distal terminus; and the enlarged distal terminus is integral to the grasper wire.

Also in some of these embodiments, the enlarged distal terminus comprises a hook.

Also in some of these embodiments, the enlarged distal terminus fills 50% or more of an area of the distal hole of the needle body when the enlarged distal terminus is in the first position.

In some embodiments, the elongated proximal-to-intermediate portion and the enlarged distal terminus are formed from a cut tube; the elongated proximal-to-intermediate portion comprises a proximal cylindrical portion and an intermediate semi-cylindrical portion; the enlarged distal terminus comprises a distal cylindrical portion; the proximal cylindrical portion is fixedly attached to the retriever tube and extends distally therefrom; and the grasper magnet is disposed adjacent the intermediate semi-cylindrical portion.

In some of these embodiments, the enlarged distal terminus is reversibly moveable between the first position and the second position based on translation of the enlarged distal terminus from partially inside of the needle lumen to entirely outside of the needle lumen through the distal hole of the needle body; and the enlarged distal terminus has a size sufficiently small to allow contact between the grasper magnet and a suture magnet of a magnetic suture attracted thereto when the enlarged distal terminus is in the second position and to allow a suture of the magnetic suture to pass when the enlarged distal terminus is in the first position, and sufficiently large to block the suture magnet of the magnetic suture from exiting the needle lumen through the distal hole of the needle body when the enlarged distal terminus is in the first position. Also in some of these embodiments, the in enlarged distal terminus comprises a hook. Also in some of these embodiments, the enlarged distal terminus fills 50% or more of an area of the distal hole of the needle body when the enlarged distal terminus is in the first position.

In some embodiments, the grasper member is integral to the retriever body; the retriever body and the elongated proximal-to-intermediate portion and the enlarged distal terminus of the grasper member are formed from a cut tube; the retriever body comprises a proximal cylindrical portion, the elongated proximal-to-intermediate portion comprises an intermediate semi-cylindrical portion, and the enlarged distal terminus comprises a distal cylindrical portion; and the grasper magnet is disposed adjacent the intermediate semi-cylindrical portion.

In some of these embodiments, the enlarged distal terminus is reversibly moveable between the first position and the second position based on translation of the enlarged distal terminus from partially inside of the needle lumen to entirely outside of the needle lumen through the distal hole of the needle body; and the enlarged distal terminus has a size sufficiently small to allow contact between the grasper magnet and a suture magnet of a magnetic suture attracted thereto when the enlarged distal terminus is in the second position and to allow a suture of the magnetic suture to pass when the enlarged distal terminus is in the first position, and sufficiently large to block the suture magnet of the magnetic suture from exiting the needle lumen through the distal hole of the needle body when the enlarged distal terminus is in the first position. Also in some of these embodiments, the enlarged distal terminus comprises a hook. Also in some of these embodiments, the enlarged distal terminus fills 50% or more of an area of the distal hole of the needle body when the enlarged distal terminus is in the first position.

In some embodiments, the magnet-assisted suture grasper further comprises a magnet wire having a proximal portion and a distal portion, wherein the proximal portion of the magnet wire is fixedly disposed within the retriever body and the grasper magnet is fixedly attached to the distal portion of the magnet wire, either directly or indirectly. In some of these embodiments, the magnet-assisted suture grasper further comprises a grasper ferrule comprising a proximal end, a distal end, and a ferrule body extending therebetween, the ferrule body having a proximal hole, a distal hole, and a ferrule lumen extending therebetween, wherein: the grasper ferrule is fixedly disposed within the retriever body; and the magnet wire extends distally from the retriever body. Also in some of these embodiments, the grasper ferrule has been crimped onto the grasper member and the magnet wire with the elongated proximal-to-intermediate portion of the grasper member and the proximal portion of the magnet wire being disposed within the ferrule lumen of the grasper ferrule; and the retriever body has been crimped onto the grasper ferrule with the grasper ferrule, the elongated proximal-to-intermediate portion of the grasper member, and the proximal portion of the magnet wire being disposed within the retriever body. Also in some of these embodiments, the retriever body has been crimped onto the grasper ferrule, the elongated proximal-to-intermediate portion of the grasper member, and the proximal portion of the magnet wire, with the grasper ferrule, the elongated proximal-to-intermediate portion of the grasper member, and the proximal portion of the magnet wire being disposed within the retriever body, and with the elongated proximal-to-intermediate portion of the grasper member and the proximal portion of the magnet wire being disposed adjacent the grasper ferrule and not within the ferrule lumen of the grasper ferrule. Also in some of these embodiments, the magnet wire further comprises a magnet wire distal terminus at the distal end of the magnet wire, the magnet-assisted suture grasper further comprises a magnet ferrule fixedly attached to the magnet wire distal terminus, and the grasper magnet is fixedly attached to the magnet ferrule.

In some embodiments, the grasper magnet is fixedly attached to the elongated proximal-to-intermediate portion of the grasper member, either directly or indirectly.

In some embodiments, the magnet-assisted suture grasper further comprises a lock mechanism that can be reversibly engaged in a setting that prevents translation of the retriever body within the needle lumen in the first direction but not the second direction when the grasper member is in the first position, wherein the spring is a part of the lock mechanism.

In some of these embodiments, maintaining the lock mechanism in the setting does not require energy input.

In some of these embodiments, the setting that prevents translation of the retriever body within the needle lumen in the first direction but not the second direction when the grasper member is in the first position is a first setting; and the lock mechanism can be reversibly engaged in a second setting that prevents translation of the retriever body within the needle lumen in the first direction but not the second direction when the grasper member is in the second position. In some examples of these embodiments, maintaining the lock mechanism in the first setting or the second setting does not require energy input.

A system for passing a magnetic suture also is disclosed. The system comprises the magnet-assisted suture grasper. The system also comprises a magnetic suture comprising a suture magnet and a suture extending from the suture magnet.

BRIEF DESCRIPTION OF THE DRAWINGS

These and other features, aspects, and advantages of the present disclosure are better understood when the following detailed description is read with reference to the accompanying drawings, which are as follows.

DETAILED DESCRIPTION

Figure 1:
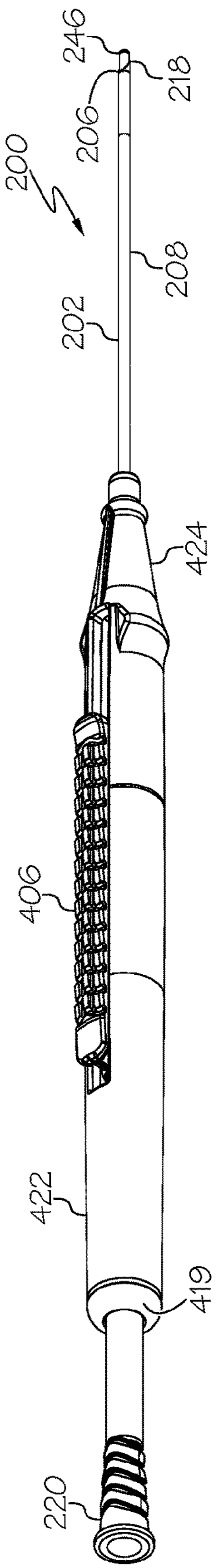
FIG. 1 is a perspective view of a magnet-assisted suture grasper comprising a suture retrieval needle, a retriever body, a grasper member comprising an elongated proximal-to-intermediate portion and an enlarged distal terminus, a grasper magnet, and a spring, as disclosed herein, in which an advancer assembly of the device is in an unlocked fully retracted position, the grasper member is in a first position, and the grasper magnet is sequestered within the suture retrieval needle as discussed herein. In this embodiment, the magnet-assisted suture grasper also comprises a grasper ferrule and a magnet wire.
Figure 2:
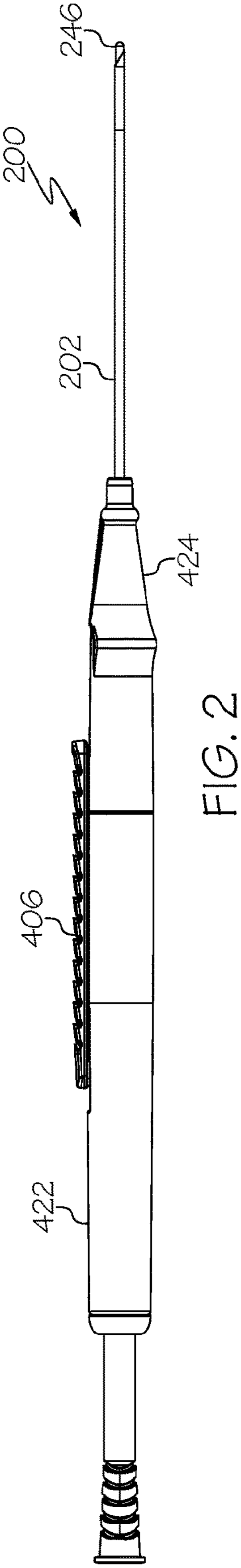
FIG. 2 is a side view of the magnet-assisted suture grasper of FIG. 1.
Figure 3:
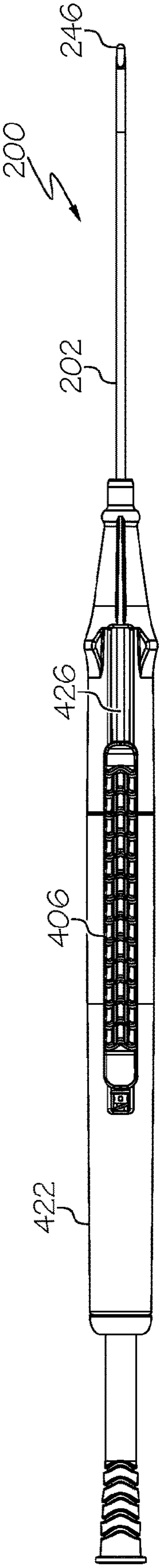
FIG. 3 is a top view of the magnet-assisted suture grasper of FIG. 1.
Figure 4:
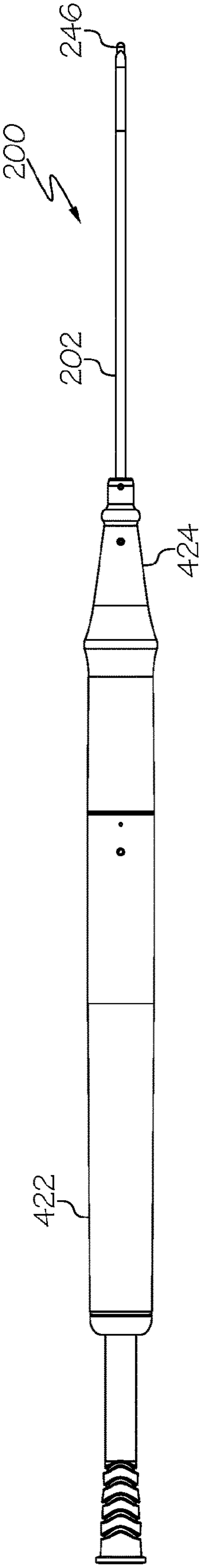
FIG. 4 is a bottom view of the magnet-assisted suture grasper of FIG. 1.
Figure 6:
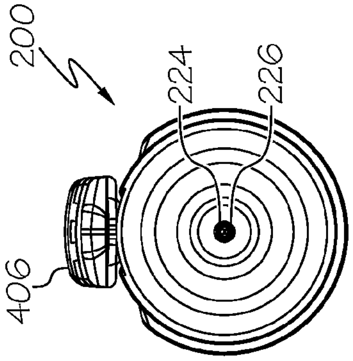
FIG. 6 is a back view of the magnet-assisted suture grasper of FIG. 1.
Figure 5:
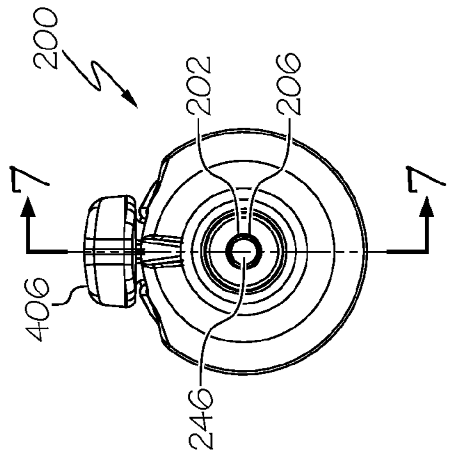
FIG. 5 is a front view of the magnet-assisted suture grasper of FIG. 1.

Our magnet-assisted suture grasper comprising a suture retrieval needle, a retriever body, a grasper member, a grasper magnet, and a spring as disclosed herein addresses the technical difficulty associated with capturing and retrieving sutures under indirect non-stereoscopic visualization, while also providing protection against injury caused by contact with the distal end of the suture retrieval needle relative to a preferred embodiment of our magnet-assisted suture grasper comprising a suture retrieval needle, a retriever body, a grasper wire, a grasper arm, and a grasper magnet as described by us in Applied Medical Technology, Inc.'s international application PCT/US2022/029627, filed May 17, 2022.

Like our magnet-assisted suture grasper described in PCT/US2022/029627, our magnet-assisted suture grasper disclosed herein involves use of two dipole magnets, a grasper magnet of a magnet-assisted suture grasper and a suture magnet of a magnetic suture, to assist with the initial positioning and holding of a magnetic suture while the magnetic suture is captured by a secondary mechanical means of the magnet-assisted suture grasper. The use of the two dipole magnets allows for a self-aligning feature, whereby the attractive forces of the northern and southern poles of the grasper magnet and the suture magnet cause the two magnets to align in a predictable manner, improving aspects of repeatability and reliability of function. Our magnet-assisted suture grasper disclosed herein greatly reduces the need to precisely position a suture passer, as the two magnetic aspects need only be brought near enough to one another that the magnetic fields can interact. The magnetic aspect of the suture is pulled into contact with the grasper magnet. This occurs without need for precise positioning to make contact. The secondary mechanical means then provides a steady-state connection between the magnetic suture and the magnet-assisted suture grasper that serves to hold the suture to the magnet-assisted suture grasper, allowing retrieval of the suture through soft tissue of a patient without needing to rely on magnetic attraction between the grasper magnet and the suture magnetic during the retrieval.

Our magnet-assisted suture grasper disclosed herein also provides protection against injury caused by contact with the distal end of the suture retrieval needle, e.g., a sharp tip of the suture retrieval needle, relative to a preferred embodiment of our magnet-assisted suture grasper described in PCT/US2022/029627 based on including a grasper member comprising a blunt distal end and also including a spring that allows the grasper member to move reversibly into the lumen of the suture retrieval needle upon pushing contact between the enlarged distal terminus and a tissue of a patient or an operator. The grasper member functions as a spring-loaded atraumatic probe in a similar manner to a Veress needle that replaces the trap wire in our previously described device. During operation of the magnet-assisted suture grasper, the grasper member initially is disposed mostly within the lumen of the suture retrieval needle, with the blunt distal end of the probe protruding from the distal end of the suture retrieval needle. Upon pushing contact between the probe and a tissue of a patient, the blunt distal end of the probe acts to push the tissue away from the distal end of the suture retrieval needle, protecting delicate tissue from the distal end of the suture retrieval needle. The spring is configured so that as the magnet-assisted suture grasper is pushed against the tissue, the probe makes contact first, the spring is loaded, and the probe translates proximally into the lumen of the suture retrieval needle. As the spring is further loaded, the probe translates more deeply into the lumen of the needle, exposing the distal end of the suture retrieval needle. Unintentional contact can be ceased before the probe has translated deeply enough to expose the distal end of the suture retrieval needle, thus preventing injury. For intentional contact, the magnet-assisted suture grasper can be pushed further until the distal end of the suture retrieval needle has pierced the tissue. Once the probe is no longer in pushing contact with the tissue, the spring releases, returning the probe to its initial position with the blunt distal end of the probe protruding from the distal end of the suture retrieval needle, once again protecting delicate tissue from the distal end of the suture retrieval needle.

The stiffness of the spring is a tunable characteristic, such that a spring with a higher or lower spring rate may be used, allowing the device to be tailored to provide more protection, or to make advancement easier, depending on the intended application. For most applications, an input force, meaning the force needed to load the spring sufficiently to expose the sharp point of the needle, of 0.25-6.4 N is generally preferred. Values outside of this range may be preferred in some specialized applications. For example, a miniaturized suture grasper intended for ophthalmic microsurgery may require a softer spring, whereas a scaled-up device intended for veterinary surgery on large animals may require a stiffer spring.

The spring-loaded atraumatic probe also serves the same function in suture retention as the trap wire of our previously described device. Specifically, following capture of a magnetic suture within the lumen of the suture retrieval needle, the spring-loaded atraumatic probe occludes the lumen of the suture retrieval needle, thereby preventing the magnetic suture from escaping from the lumen of the suture retrieval needle.

The spring-loaded atraumatic probe can be particularly advantageous for use in magnet-assisted suture graspers in which the distal end of the suture retrieval needle has a sharp tip. This can help prevent injury to a patient for example while the suture retrieval needle is being advanced percutaneously to access a body cavity, such as the abdominal cavity. This also can help prevent injury of an operator during handling of the device, for example by avoiding inadvertent needle sticks.

Our magnet-assisted suture grasper disclosed herein further optionally further comprises a lock mechanism that can be reversibly engaged in a setting that prevents translation of the retriever body within the needle lumen in a first direction but not a second direction when the grasper member is in a first position. The spring can be a part of the lock mechanism.

Our magnet-assisted suture grasper can incorporate an incompressible and reversible mechanical lock that, when engaged, fixes the longitudinal position of the grasper member in at least one direction, and thereby also fixes the position of a magnetic suture being grasped by the grasper member in the same direction. When engaged, the mechanical lock advantageously bears fully any tensile load applied to the magnetic suture in the same direction. The mechanical lock provides for a single equipoised position. Moreover, the spring can advantageously provide a second equipoised position, allowing the magnet-assisted suture grasper to be switched between positions with a momentary energy input, but requiring no additional energy input to maintain either position.

For comparison, conventional suture passers make use of a spring located between a moveable plunger element and a fixed body element. According to designs of the conventional suture passers, depressing the plunger element by the application of external force compresses the spring, causing the suture passer to transition from a closed position to an open position. Upon release of the plunger element, and thus in the absence of external force, the spring exerts a counterforce back upon the plunger, which returns the suture passer from the open position to the closed position. The conventional suture passers lack a mechanical lock, and thus rely solely on the spring to resist tensile loading of the suture in the direction which acts to pull the suture out of the suture passer. The spring thus needs to be stiff enough that the force required to compress the spring to a position where the suture passer opens sufficiently far to release the suture is greater than the expected loads that will be placed on the suture during retrieval. Additionally, since the conventional suture passers provide for only one equipoised position, which is the closed position, the operator must continually apply an external force great enough to compress the spring in order to maintain an open position of the suture passer while retrieving a suture.

With our magnet-assisted suture grasper including the lock mechanism, these loads are born by the mechanical lock rather than a spring. As a result, a lighter spring can be used, which reduces the operational force needed to move our magnet-assisted suture grasper between open and closed positions. This allows our magnet-assisted suture grasper to be slidingly operated with a single finger, which allows for a more precise gripping style better suited to delicate procedures, such as, for example, dissection and mobilization of the spermatic cord structures away from the peritoneum, such as in percutaneous inguinal ring suturing. Moreover, because the mechanical lock provides an equipoised closed position, the spring action can be reversed to also create an equipoised open position. This advantageously allows an operator to manipulate our magnet-assisted suture grasper in an open position without having to hold forcefully against a spring.

An example embodiment of a magnet-assisted suture grasper 200 for grasping a magnetic suture 500 is illustrated in FIGS. 1-17. As shown in FIGS. 1-8, a grasper member 242 of the magnet-assisted suture grasper 200 is in a first position 248 in which a grasper magnet 254 of the magnet-assisted suture grasper 200 is sequestered with a needle lumen 216 of a suture retrieval needle 202 of the magnet-assisted suture grasper 200. As shown in FIGS. 9-17, the grasper member 242 in a second position 250, in which the grasper magnet 254 is exposed from the needle lumen 216, allowing contact between the grasper magnet 254 and a magnetic suture 500 attracted thereto.

With reference to FIGS. 60-63, the magnetic suture 500 to be grasped can comprise a suture magnet 502 and a suture 504 extending from the suture magnet 502. The magnetic suture 500 can be, for example, a magnetic suture as described in U.S. Pub. No. 2021/0059667, which is incorporated herein by reference. Thus, the magnetic suture 500 can further comprise a magnet ferrule 506 with a tapered region 508 in which the suture 504 is provided knotted and secured with an adhesive and a straight region 510 in which the suture magnet 502 is provided.

Figure 17:
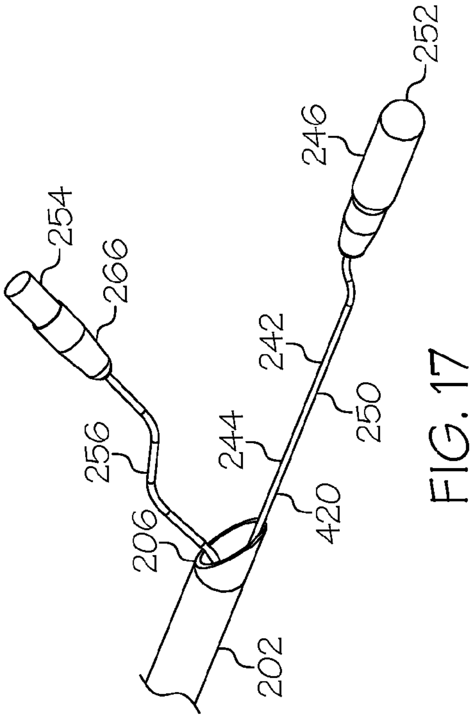
FIG. 17 is a perspective view of a distal portion of the magnet-assisted suture grasper of FIG. 9, in which the grasper member is in the second position.
Figure 18:
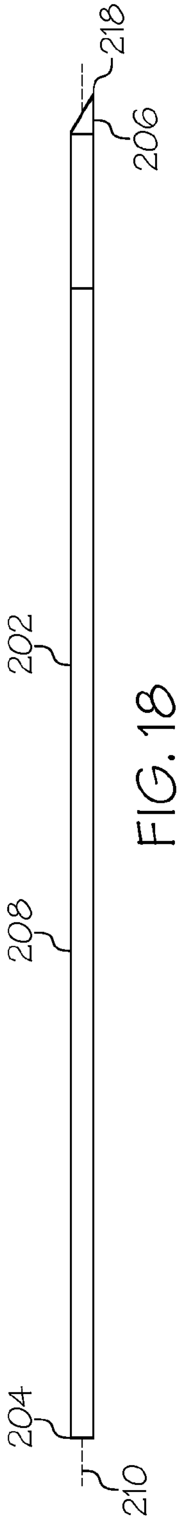
FIG. 18 is a side view of the suture retrieval needle of the magnet-assisted suture grasper of FIG. 1.
Figure 19:
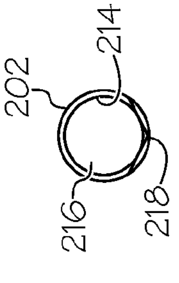
FIG. 19 is a front view of the suture retrieval needle of FIG. 18.
Figure 20:
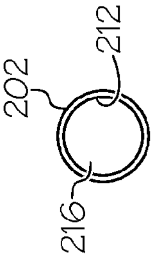
FIG. 20 is a back view of the suture retrieval needle of FIG. 18.

As shown in FIGS. 18-20, with reference to FIGS. 1-17, the magnet-assisted suture grasper 200 comprises a suture retrieval needle 202 comprising a proximal end 204, a distal end 206, and a needle body 208 extending therebetween. The needle body 208 defines a needle body axis 210 between the proximal end 204 and the distal end 206 of the suture retrieval needle 202. The needle body 208 has a proximal hole 211, a distal hole 214, and a needle lumen 216 extending therebetween along the needle body axis 210.

The suture retrieval needle 202 can be, for example, a hypodermic needle. For example, the suture retrieval needle 202 can be an introducer needle designed for introducing guide wires into a vessel, applied here as the suture retrieval needle 202. Also for example, the suture retrieval needle 202 can be a 24-gauge needle, a 21-gauge needle, an 18-gauge needle, a 17-gauge needle, a 16-gauge needle, or a 14 gauge needle.

In some embodiments, the suture retrieval needle 202 is straight. In accordance with these embodiments, the needle body axis 210 thereby is straight. Alternatively, in some embodiments, the suture retrieval needle 202 is curved. In accordance with these embodiments, the needle body axis 210 thereby is curved. In some embodiments, one or more portions of the suture retrieval needle 202 can be straight, and one or more portions can be curved. For example, in some embodiments, the suture retrieval needle 202 includes a curve at or near its distal end 206 but otherwise is straight. In accordance with these embodiments, the needle body axis 210 also includes a curve at or near the distal end 206 of the suture retrieval needle 202, but otherwise is straight.

As shown in FIG. 18, with reference to FIGS. 1-17, in some embodiments, the suture retrieval needle 202 has a sharp tip 218. This can be advantageous for piercing tissue during insertion of the suture retrieval needle 202 into a patient.

Figure 21:
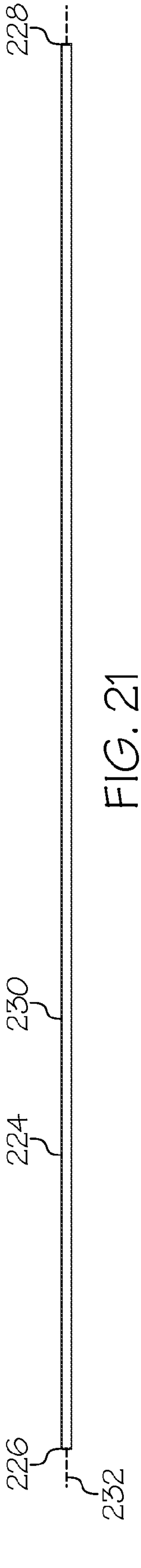
FIG. 21 is a side view of the retriever body of the magnet-assisted suture grasper of FIG. 1.
Figure 22:
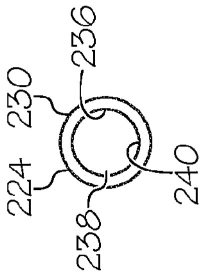
FIG. 22 is a front view of the retriever body of FIG. 21.
Figure 23:
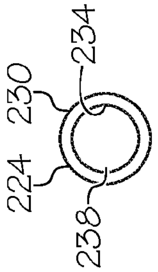
FIG. 23 is a back view of the retriever body of FIG. 21.

As shown in FIGS. 21-23, with reference to FIGS. 1-17, the magnet-assisted suture grasper 200 also comprises a retriever body 224. The retriever body 224 is partially disposed within the needle lumen 216 and translatable therein along the needle body axis 210. The retriever body 224 can be made from a polymer, such as nylon, polyether ether ketone, polycarbonate, or acrylonitrile butadiene styrene, or a metal, such as stainless steel or Nitinol.

In some embodiments, the retriever body 224 comprises a proximal end 226, a distal end 228, and a retriever tube 230 extending therebetween. In these embodiments, the retriever tube 230 defines a retriever tube axis 232 between the proximal end 226 and the distal end 228 of the retriever body 224. Moreover, the retriever tube 230 has a proximal hole 234, a distal hole 236, and a retriever tube lumen 238 extending therebetween along the retriever tube axis 232. In addition, the proximal hole 234 of the retriever tube 230 is in fluid communication with the distal hole 214 of the needle body 208 through the retriever tube lumen 238 and the needle lumen 216.

The retriever tube lumen 238 can be advantageous by allowing recovery of liquids and/or gasses from a surgical site of a patient and/or delivery of contrast agents to the surgical site through the retriever body 224. This broadens the applicability of the magnet-assisted suture grasper 200 for use with interventional techniques that employ fluid exchange to confirm the intracorporeal position of the distal end of the suture retrieval needle 202 of the magnet-assisted suture grasper 200. For example, a need exists within the field of interventional radiology for the ability to confirm the location of cannulas inside the gastric lumens of patients during gastropexy. With the magnet-assisted suture grasper 200 comprising the retriever body 224 comprising the retriever tube lumen 238, following introduction of the suture retrieval needle 202 into a patient, aspiration of a small amount of stomach juice or air can be used to confirm the intraluminal position of the distal end of the suture retrieval needle 202. Alternatively, a small amount of liquid radiographic contrast agent can be injected through the retriever tube lumen 238 of the retriever body 224 into the gastric lumen of the patient, allowing the intraluminal position to be confirmed through radiographic imaging.

Alternatively, in some embodiments, the retriever body 224 comprises a proximal end 226, a distal end 228, a distal hole 236, and a retriever body cavity 240 extending within the retriever body 224 from the distal hole 236 of the retriever body 224.

Figure 24:
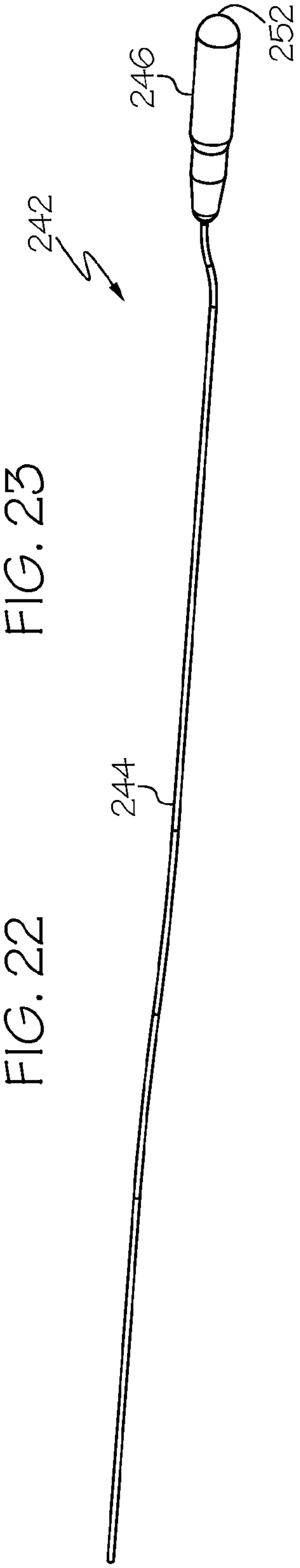
FIG. 24 is a perspective view of the grasper member comprising the elongated proximal-to-intermediate portion and the enlarged distal terminus of the magnet-assisted suture grasper of FIG. 1.

As shown in FIG. 24, with reference to FIGS. 1-17, the magnet-assisted suture grasper 200 also comprises a grasper member 242. The grasper member 242 comprises an elongated proximal-to-intermediate portion 244 and an enlarged distal terminus 246. The grasper member 242 extends distally from the retriever body 224 and is reversibly moveable with respect to the needle lumen 216 between a first position 248 and a second position 250. In some embodiments, the elongated proximal-to-intermediate portion 244 of the grasper member 242 is fixedly disposed within the retriever body 224. In some embodiments, the elongated proximal-to-intermediate portion 244 of the grasper member 242 is integral to the retriever body 224.

As shown in FIG. 24, the enlarged distal terminus 246 of the grasper member 242 comprises a blunt distal end 252. The blunt distal end 252 can be blunt for example based on having a surface that is smooth and/or rounded and/or without any sharp features. The blunt distal end 252 is advantageous for allowing the enlarged distal terminus 246 to serve as an atraumatic probe during use of the magnet-assisted suture grasper 200.

Figure 8:
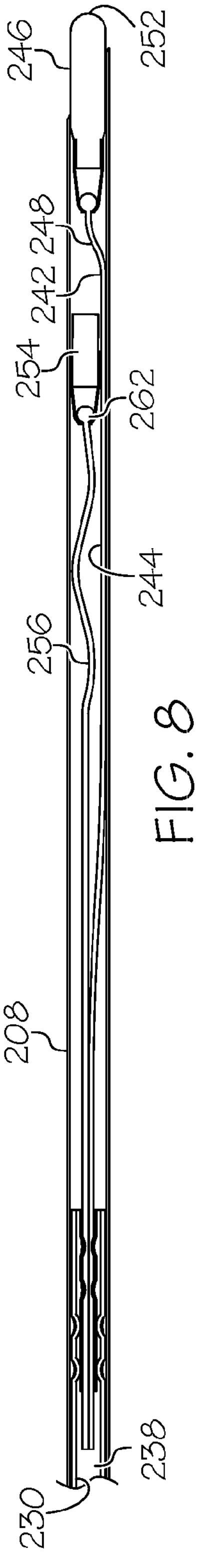
FIG. 8 is an expanded sectional view of the magnet-assisted suture grasper of FIG. 7.
Figure 9:
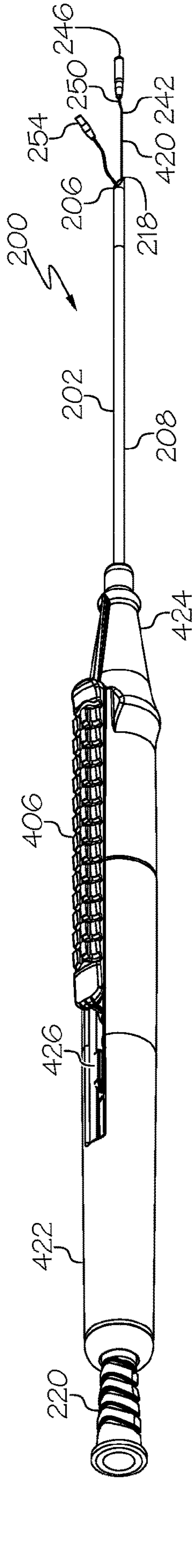
FIG. 9 is a perspective view of the magnet-assisted suture grasper of FIG. 1 in which the advancer assembly of the device is in a fully extended position, the grasper member is in a second position, and the grasper magnet is exposed, allowing contact between the grasper magnet and a magnetic suture attracted thereto.
Figure 10:
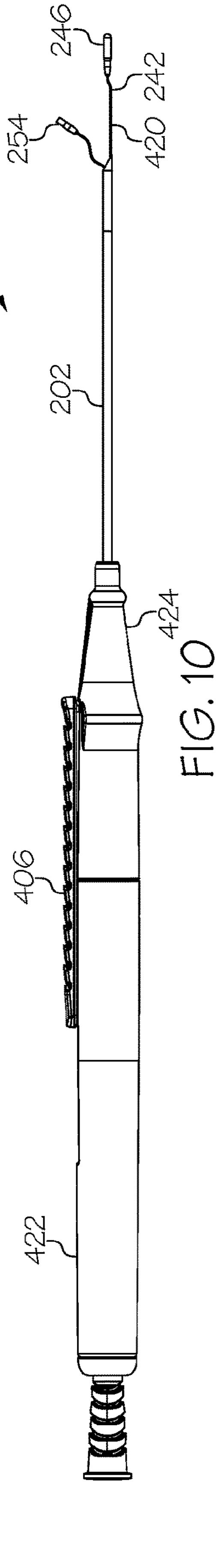
Figure 11:
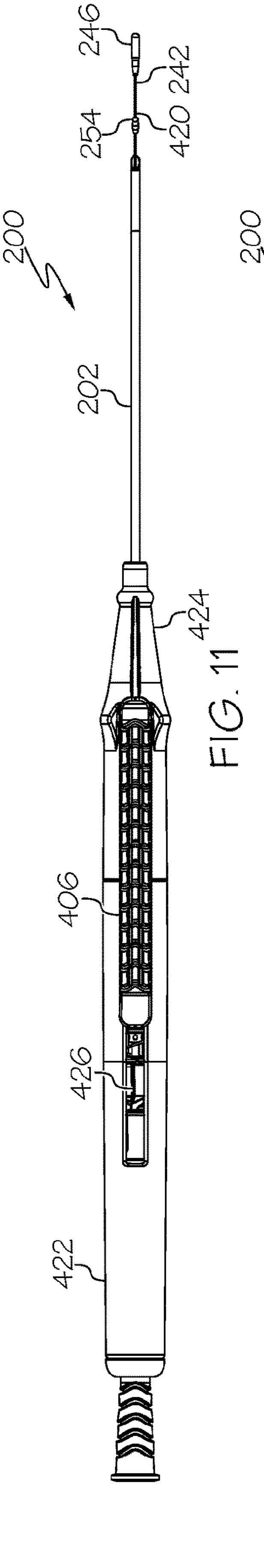
FIG. 11 is a top view of the magnet-assisted suture grasper of FIG. 9.
Figure 12:
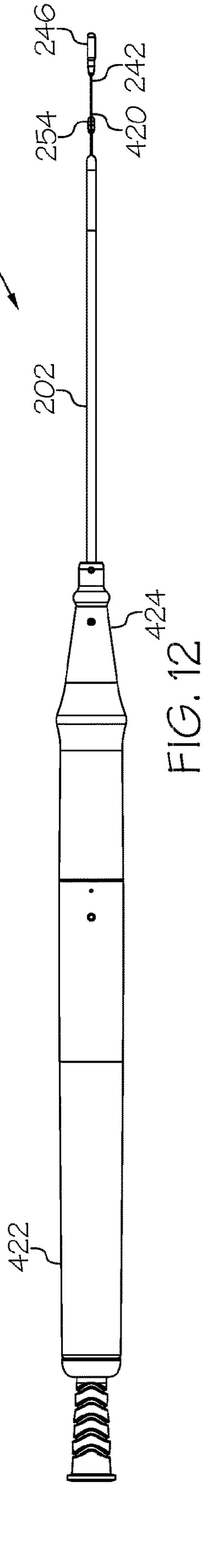
FIG. 12 is a bottom view of the magnet-assisted suture grasper of FIG. 9.
Figure 14:
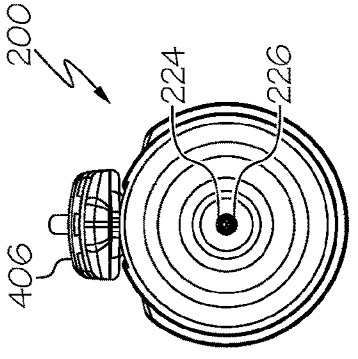
FIG. 14 is a back view of the magnet-assisted suture grasper of FIG. 9.
Figure 13:
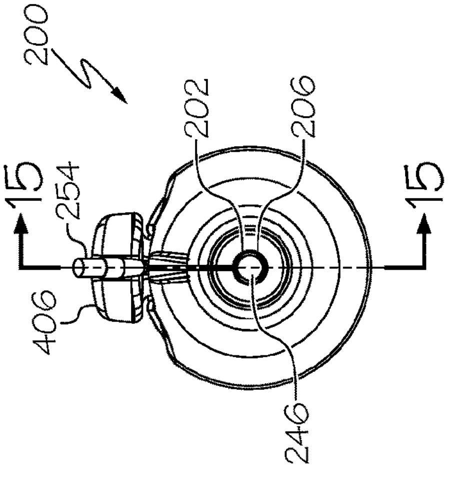
FIG. 13 is a front view of the magnet-assisted suture grasper of FIG. 9.
Figure 15:
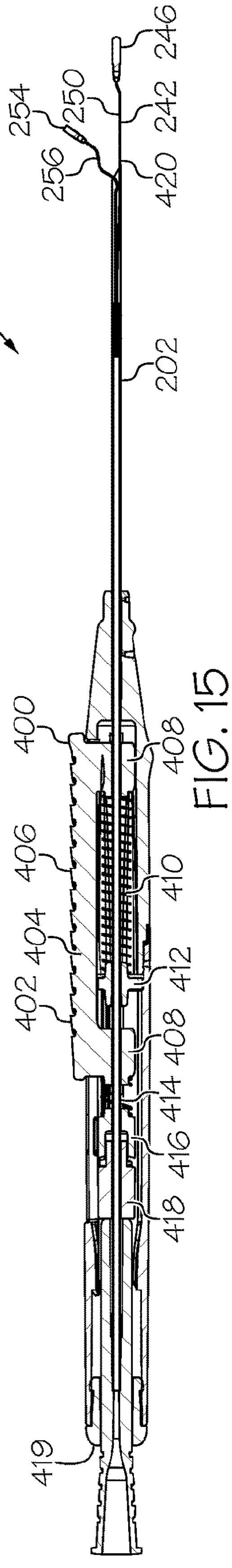
FIG. 15 is a sectional view of the magnet-assisted suture grasper of FIG. 9, viewed along the cutting plane shown in FIG. 13.
Figure 16:
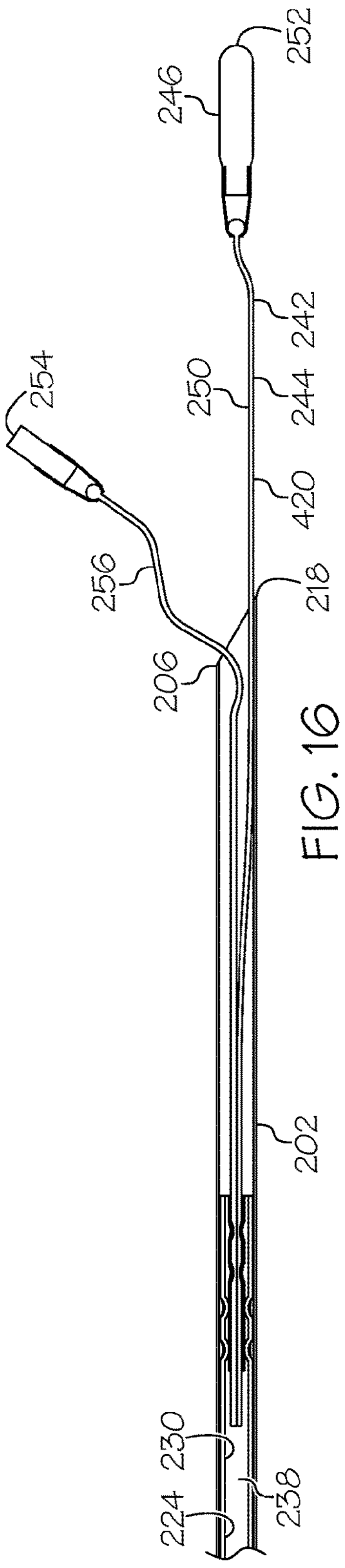
FIG. 16 is an expanded sectional view of the magnet-assisted suture grasper of FIG. 15.

As shown by comparison of FIG. 8 and FIG. 16, the enlarged distal terminus 246 extends partially from the distal hole 214 of the needle body 208 when the grasper member 242 is in the first position 248 and extends entirely beyond the distal hole 214 of the needle body 208 when the grasper member 242 is in the second position 250. Because the enlarged distal terminus 246 extends partially from the distal hole 214 of the needle body 208 when the grasper member 242 is in the first position 248, the enlarged distal terminus 246 prevents inadvertent contact between the distal end 206 of the suture retrieval needle 202 and tissues of patients and operators. Moreover, when a magnetic suture 500 has been captured within the needle lumen 216 of the magnet-assisted suture grasper 200 with the grasper member 242 being in the first position 248, because the enlarged distal terminus 246 extends only partially from the distal hole 214 of the needle body 208 when the grasper member 242 is in the first position 248, the enlarged distal terminus 246 prevents the magnetic suture 500 from being pulled out of the needle lumen 216. Because the enlarged distal terminus 246 extends entirely beyond the distal hole 214 of the needle body 208 when the grasper member 242 is in the second position 250, the grasper magnet 254 can exit the needle lumen 216 of the suture retrieval needle 202 when the grasper member 242 is in the second position 250, as discussed below.

The grasper member 242 can be made from, for example, a polymeric material, a metal with a high proportional limit, such as Nitinol, or a hard metal, such as stainless steel.

The enlarged distal terminus 246 can have an outer diameter that is at least about 50% the inner diameter of the needle lumen 216, for example about 60% to 95%, 70% to 95%, or 80% to 95% the inner diameter of the needle lumen 216.

In some embodiments, the grasper member 242 is more flexible than the needle body 208. This can be advantageous for suture retrieval needles 202 in which one or more portions of the suture retrieval needle 202 are curved, e.g., a suture retrieval needle 202 that includes a curve at or near its distal end 206 but otherwise is straight. Then the grasper member 242 is preferentially made of a polymeric material, or a metal with a high proportional limit, such as Nitinol, to allow the grasper member 242 to elastically deform around the curve of the suture retrieval needle 202.

Figure 25:
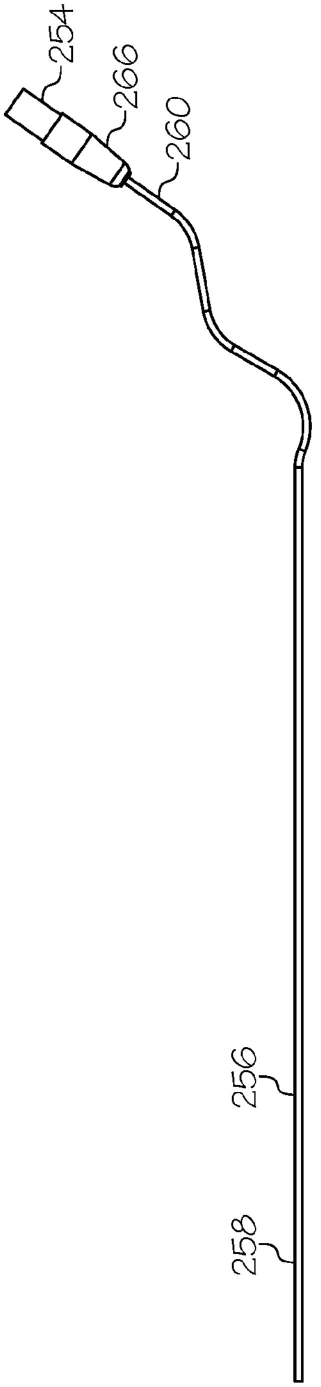
FIG. 25 is a side view of the grasper magnet and magnet wire of the magnet-assisted suture grasper of FIG. 1.

As shown in FIG. 25, with reference to FIGS. 1-17, the magnet-assisted suture grasper 200 also comprises a grasper magnet 254 being disposed adjacent the elongated proximal-to-intermediate portion 244 of the grasper member 242. As shown by comparison of FIG. 8 and FIG. 16, the magnet-assisted suture grasper 200 sequesters the grasper magnet 254 within the needle lumen 216 when the grasper member 242 is in the first position 248 and exposes the grasper magnet 254 from the needle lumen 216 when the grasper member 242 is in the second position 250. The grasper magnet 254 can be, for example, a permanent dipole magnet.

As shown in FIG. 25, with reference to FIGS. 1-17, in some embodiments the magnet-assisted suture grasper 200 further comprises a magnet wire 256 having a proximal portion 258 and a distal portion 260. The proximal portion 258 of the magnet wire 256 is fixedly disposed within the retriever body 224 and the grasper magnet 254 is fixedly attached to the distal portion 260 of the magnet wire 256, either directly, e.g., based on adhesion or other direct attachment, or indirectly, e.g., based on attachment through one or more intermediate parts, such as a ferrule, ring, or sleeve, among other intermediate parts.

In these embodiments, translation of the retriever tube 230 also results in translation of the magnet wire 256, and thus also the grasper magnet 254.

In some of these embodiments, the magnet wire 256 further comprises a magnet wire distal terminus 262 at the distal end of the magnet wire 256, the magnet-assisted suture grasper 200 further comprises a magnet ferrule 266 fixedly attached to the magnet wire distal terminus 262, and the grasper magnet 254 is fixedly attached to the magnet ferrule 266.

The magnet wire 256 can be, for example, a metal wire, such as a Nitinol wire or a stainless steel wire, or a plastic wire, and can be formed, for example, as a solid wire, a stranded wire, or a braided wire, and can have a shape, for example, based on being a shaped wire and/or a stamped wire, and can comprise, for example, one or more wires joined together at one or more common points, for example, by welding, soldering, braiding, crimping, adhesive, or other means.

Considering attachment of the grasper magnet 254 to the magnet wire 256 in more detail, the grasper magnet 254 can be attached to the magnet wire 256, for example, similarly as described in U.S. Pub. No. 2021/0059667 for attachment of a magnet to a suture. This can be accomplished as follows. The grasper magnet 254 can be attached to a magnet ferrule 266, which is attached to a magnet wire 256 having an enlarged magnet wire distal terminus 262. With reference to U.S. Pub. No. 2021/0059667, the enlarged magnet wire distal terminus 262 would replace the knot tied in a suture. A ball end is the preferred shape for the magnet wire distal terminus 262 and a mono-filament with a round cross-section is the preferred shape of the magnet wire 256. However, as long as the magnet wire 256 and the magnet wire distal terminus 262 are sized appropriately, other constructions and final shapes would also be suitable. The magnet wire distal terminus 262 may be formed into any shape, e.g., cubic, cylindrical, pyramidal, organic, etc., and the magnet wire 256 may be of any cross sectional shape, e.g., square, rectangular, cruciform, etc., and may be of mono- or multi-filament construction.

The magnet wire 256 must be sized small enough to fit through the small opening of the magnet ferrule 266, while the magnet wire distal terminus 262 must be sized larger than the small opening of the magnet ferrule 266 and smaller than the large opening of the magnet ferrule 266. The magnet wire distal terminus 262 may be integrated into the magnet wire 256, e.g., the magnet wire distal terminus 262 can be melt formed, coined, bent, etc., or it may be a separate component. If a separate component, it may be attached by mechanical means, e.g., swaged, threaded, interference fit, pinned, etc., by adhesive means, or by other means, e.g., welding, soldering, brazing, etc.

To assemble the grasper magnet 254, the magnet ferrule 266, and the magnet wire 256, the magnet wire 256 is first passed through the magnet ferrule 266 from its distal end to its proximal end, so that the magnet wire distal terminus 262 becomes positioned inside the magnet ferrule 266. The grasper magnet 254 is then installed from the distal end, and attached to the magnet ferrule 266. The grasper magnet 254 can be attached by mechanical means, e.g., swaged, threaded, interference fit, pinned, etc., or adhesive means or other means, e.g., welding, brazing, etc. Once the grasper magnet 254 is attached, the magnet wire distal terminus 262 is permanently captured between the grasper magnet 254 and the magnet ferrule 266, and the sub-assembly is complete.

As shown in FIGS. 16-18, in some embodiments the grasper magnet 254 is displaced radially from the needle body axis 210 when the grasper member 242 is in the second position 250. This can be advantageous by providing an operator of the magnet-assisted suture grasper 200 an additional range of motion to move the grasper magnet 254 within a site of a patient by rotation of the magnet-assisted suture grasper 200 and thus greater versatility in positioning the grasper magnet 254 relative to a magnetic suture 500 in the site.

Figure 26:
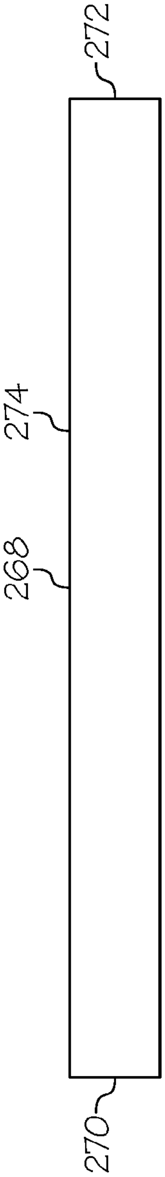
FIG. 26 is a side view of the grasper ferrule of the magnet-assisted suture grasper of FIG. 1.
Figure 28:
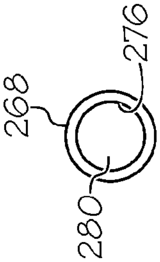
FIG. 28 is a back view of the grasper ferrule of FIG. 26.
Figure 27:
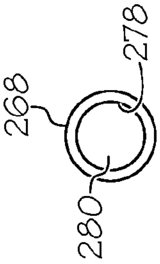
FIG. 27 is a front view of the grasper ferrule of FIG. 26.
Figure 29:
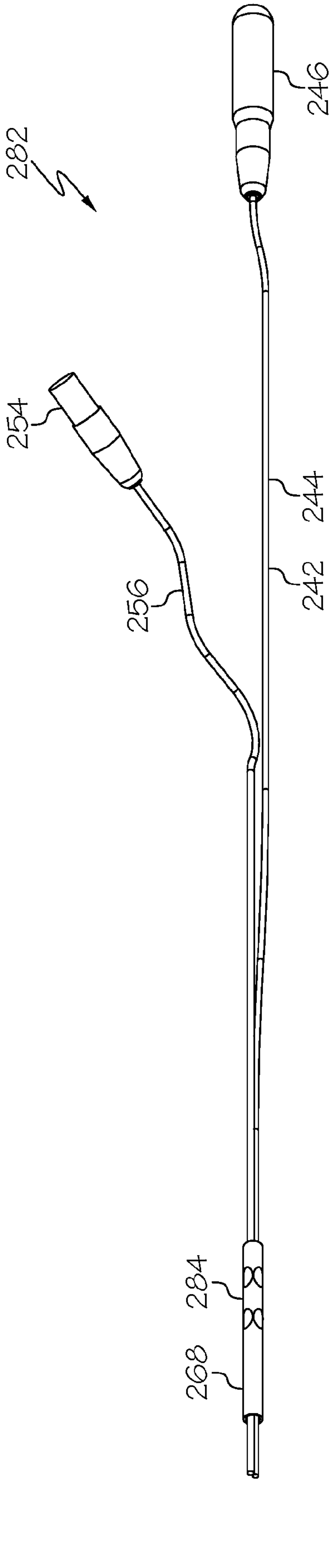
FIG. 29 is a perspective view of the grasper ferrule, the grasper member, the grasper magnet, and the magnet wire of the magnet-assisted suture grasper of FIG. 1, in which the grasper ferrule has been crimped onto the grasper member and the magnet wire.
Figure 30:
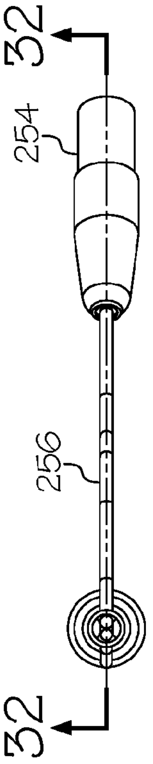
FIG. 30 is a back view of the grasper ferrule, the grasper member, the grasper magnet, and the magnet wire of FIG. 29.
Figure 31:
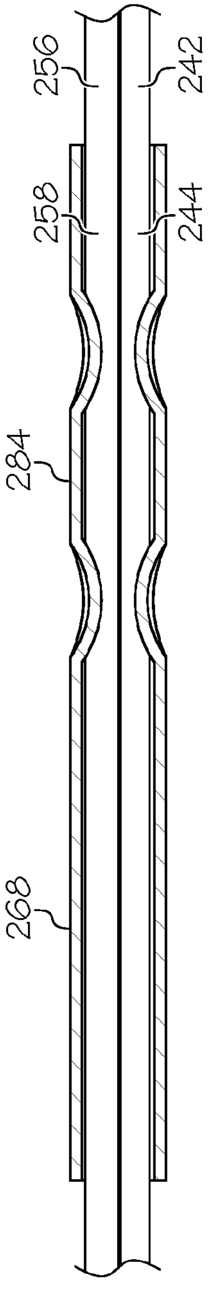
FIG. 31 is an expanded sectional view of the grasper ferrule, the grasper member, and the magnet wire of FIG. 29, viewed along the cutting plane shown in FIG. 30.

As shown in FIGS. 26-28, with reference to FIGS. 29-34, also in some embodiments the magnet-assisted suture grasper 200 further comprises a grasper ferrule 268 comprising a proximal end 270, a distal end 272, and a ferrule body 274 extending therebetween. In these embodiments the ferrule 274 of the grasper ferrule 268 has a proximal hole 276, a distal hole 278, and a ferrule lumen 280 extending therebetween. The grasper ferrule 268 is fixedly disposed within the retriever body 224, e.g., within the retriever tube lumen 238 or the retriever body cavity 240. The magnet wire 256 extends distally from the retriever body 224.

The grasper ferrule 268 can be used to fixedly attach the grasper member 242 and the magnet wire 256 to the retriever tube 230.

In some approaches, a grasper ferrule subassembly 282 including the grasper member 242, the magnet wire 256, and the grasper ferrule 268 can be assembled as follows. The elongated proximal-to-intermediate portion 244 of the grasper member 242 and the proximal portion of the magnet wire 256 are inserted into the ferrule lumen 280 of the grasper ferrule 268 via the distal hole 278 of the grasper ferrule 268, as shown with reference to FIGS. 29-31 The grasper ferrule 268 is crimped onto the elongated proximal-to-intermediate portion 244 of the grasper member 242 and the proximal portion 258 of the magnet wire 256, elastically and plastically deforming the grasper ferrule 268, the elongated proximal-to-intermediate portion 244 of the grasper member 242, and the proximal portion 258 of the magnet wire 256. This creates an inner crimp joint 284.

The inner crimp joint 284 is a permanent mechanical joint. This provides advantages relative to an adhesive joint. The advantages include greater speed and throughput, as a crimp joint takes approximately 10 to 95% less time to complete than a comparable adhesive joint, with timing depending on the adhesive used. Moreover, a crimp joint provides strong attachment immediately upon completion of crimping, whereas an adhesive joint may require special handling until the adhesive cures. The advantages also include greater chemical compatibility. Since a crimp joint is an entirely mechanical joint, it does not rely on intermolecular bonds of an adhesive to keep the parts attached, and thus will not lose strength when exposed to environmental agents that can cause the intermolecular bonds to fail. In addition, regarding metal crimp joints in particular, e.g., for a grasper ferrule 268, a grasper member 242, and a magnet wire 256 that are each made from metals, advantages also include increased stability and shelf life. As polymeric materials age, macroscopic changes in the physical and chemical properties of the polymeric materials occur over time due to molecular-level relaxations of the polymer chains and continued chemical reactions. These changes tend to negatively affect the strength and toughness of an adhesive joint. Metals exhibit far less structural changes than polymers over the same time and temperature ranges. Therefore, a crimp joint such as the one described, which consists entirely of metallic components, with no polymeric interface, will generally be more stable over time and will thus be less-susceptible to age-related degradation.

Figure 32:
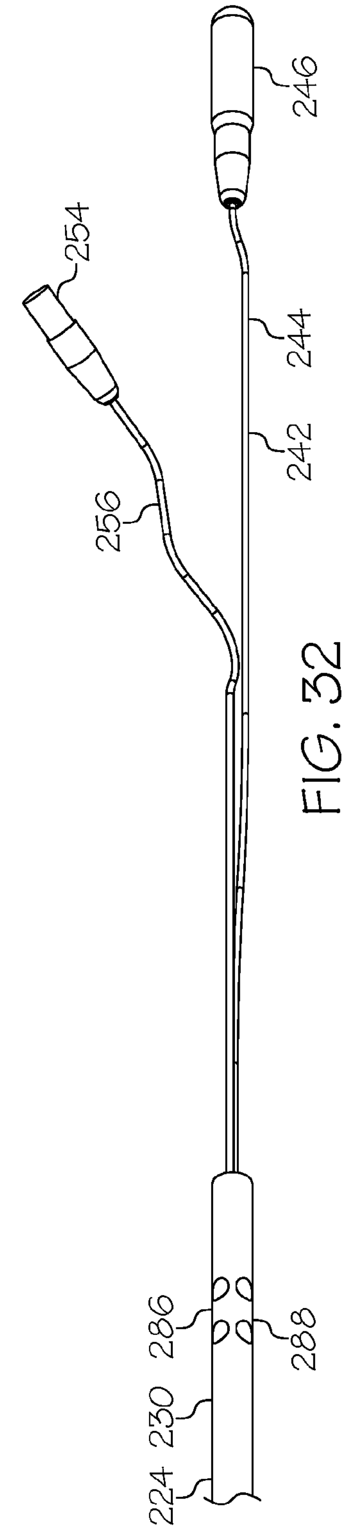
FIG. 32 is a perspective view of the retriever body, the grasper ferrule, the grasper member, the grasper magnet, and the magnet wire of the magnet-assisted suture grasper of FIG. 1, in which the retriever body has been crimped onto the grasper ferrule.
Figure 33:
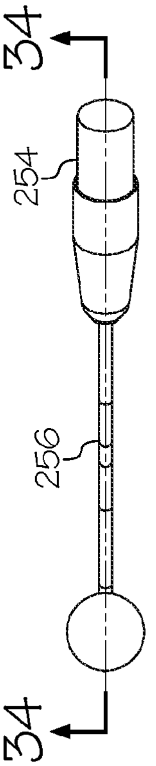
FIG. 33 is a front view of the retriever body, the grasper ferrule, the grasper member, the grasper magnet, and the magnet wire of FIG. 32.
Figure 34:
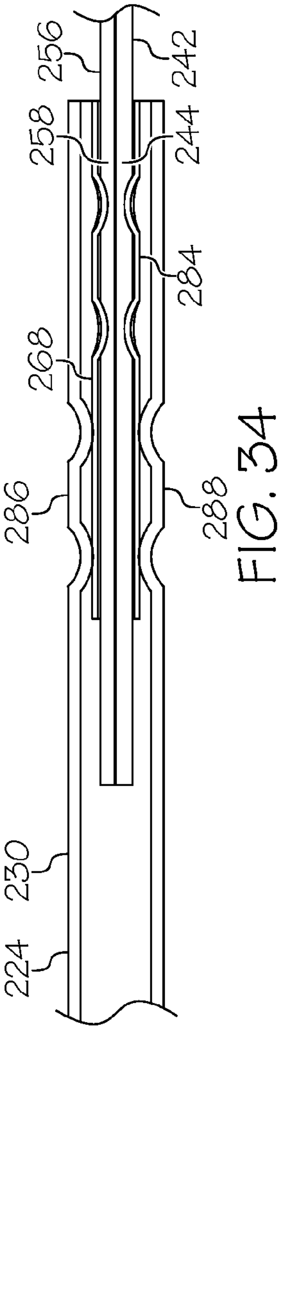
FIG. 34 is an expanded side sectional view of the retriever body, the grasper ferrule, the grasper member, and the magnet wire of FIG. 32, viewed along the cutting plane shown in FIG. 33.

The grasper ferrule subassembly 282 is then inserted into the retriever body 224, e.g., into the retriever tube lumen 238 or the retriever body cavity 240 via the distal hole 236, as shown with reference to FIGS. 32-34. The grasper ferrule subassembly 282 can be inserted such that the grasper ferrule 268 is disposed entirely within the retriever body 224, with the distal end 272 of the grasper ferrule 268 being adjacent the distal hole 236 of the retriever body 224. The retriever body 224 is crimped onto the grasper ferrule 268. This creates an outer crimp joint 286. This permanently joins the grasper member 242, the magnet wire 256, and the grasper ferrule 268 to the retriever body 224, with similar advantages as described above regarding the permanent mechanical joint of the grasper ferrule subassembly 282.

Figure 35:
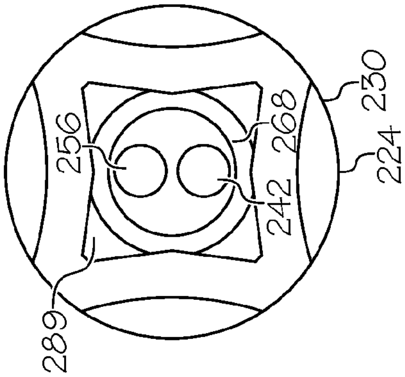
FIG. 35 is cross-sectional view of the retriever body, the grasper ferrule, the grasper member, and the magnet wire of FIG. 32.
Figure 36:
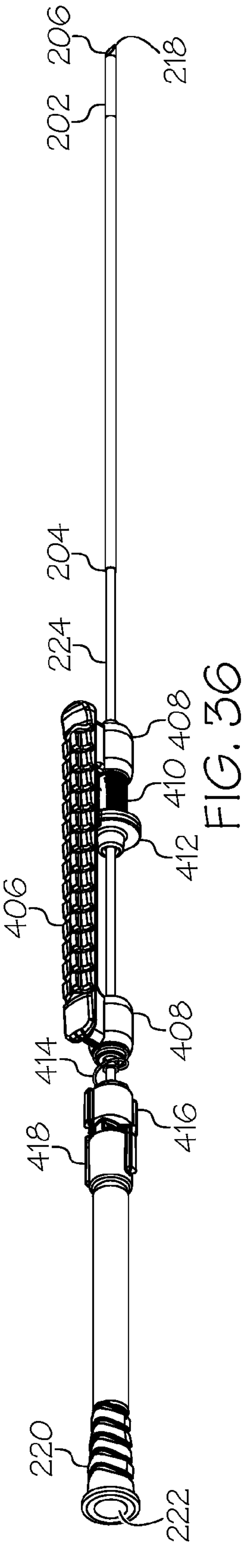
FIG. 36 is a perspective view of an advancer assembly of the magnet-assisted suture grasper of FIG. 1, in which the advancer assembly is in an unlocked fully retracted position.
Figure 37:
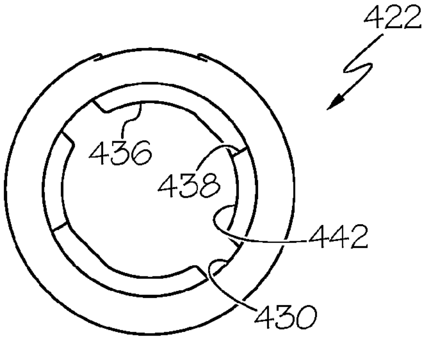
FIG. 37 is a proximal end view of a barrel of the magnet-assisted suture grasper of FIG. 1.
Figure 38:
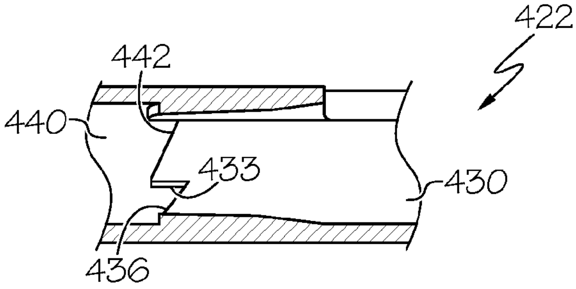
FIG. 38 is a partial longitudinal view of the barrel of FIG. 37.
Figure 39:
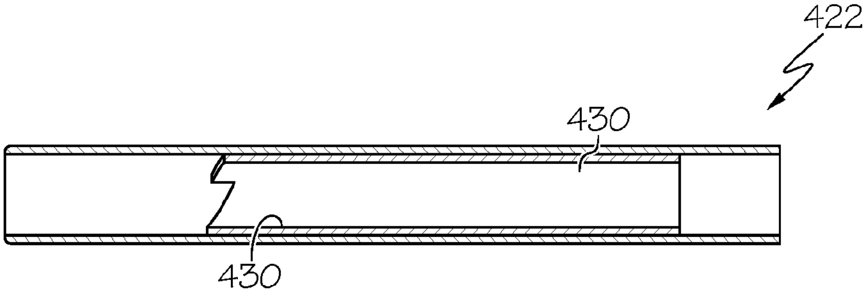
FIG. 39 is a partial sectional view of the barrel of FIG. 37 through guide channels of the barrel.
Figure 40:
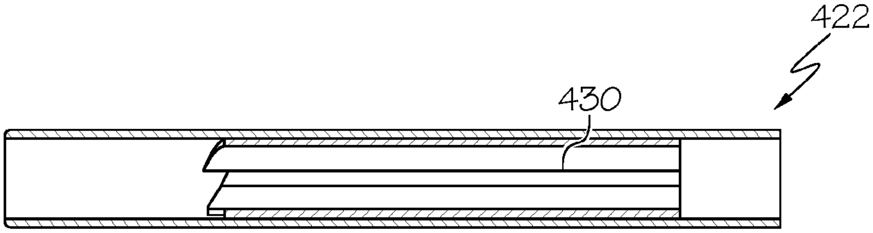
FIG. 40 is a partial sectional view of the barrel of FIG. 37 perpendicular to guide channels of the barrel.
Figure 41:
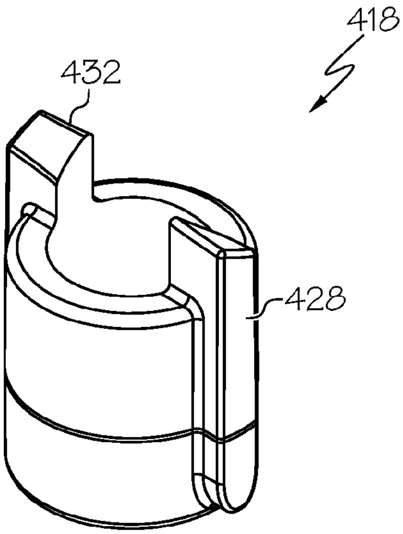
FIG. 41 is a perspective view of a lock cam of the magnet-assisted suture grasper of FIG. 1.
Figure 42:
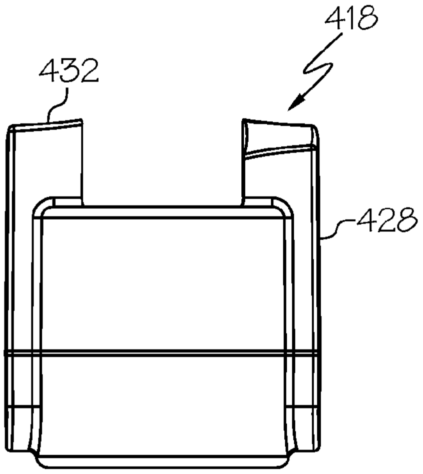
FIG. 42 is a side view of the lock cam of FIG. 41.
Figure 43:
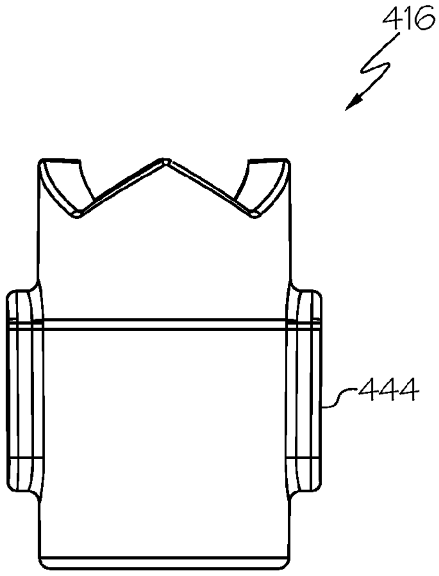
FIG. 43 is a side view of a drive cam of the magnet-assisted suture grasper of FIG. 1.
Figure 44:
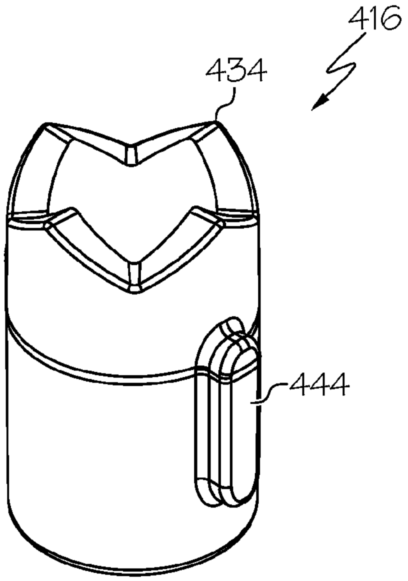
FIG. 44 is a perspective view of the drive cam of FIG. 43.
Figure 45:
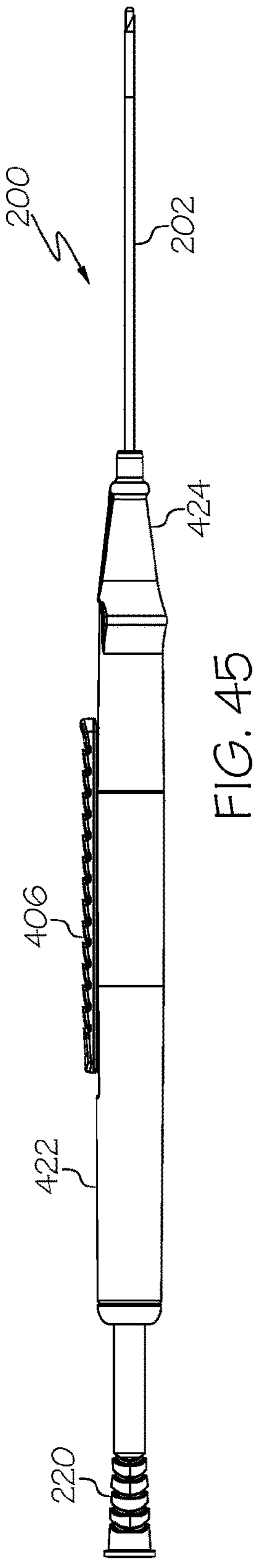
FIG. 45 is a side view of the magnet-assisted suture grasper of FIG. 1, in which the advancer assembly is in a locked partially retracted position and the grasper member is in the first position.
Figure 46:
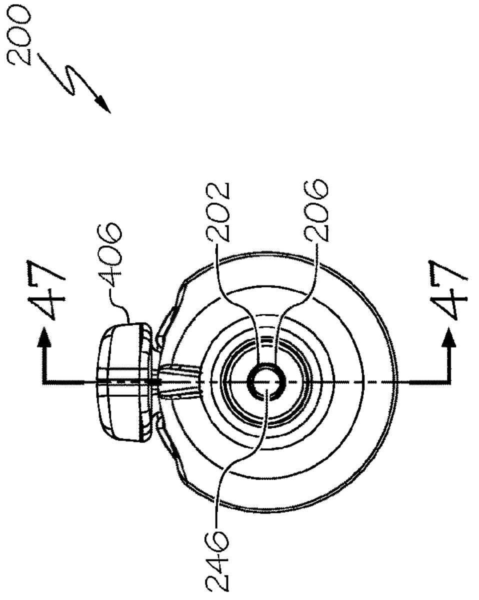
FIG. 46 is a front view of the magnet-assisted suture grasper of FIG. 45.
Figure 47:
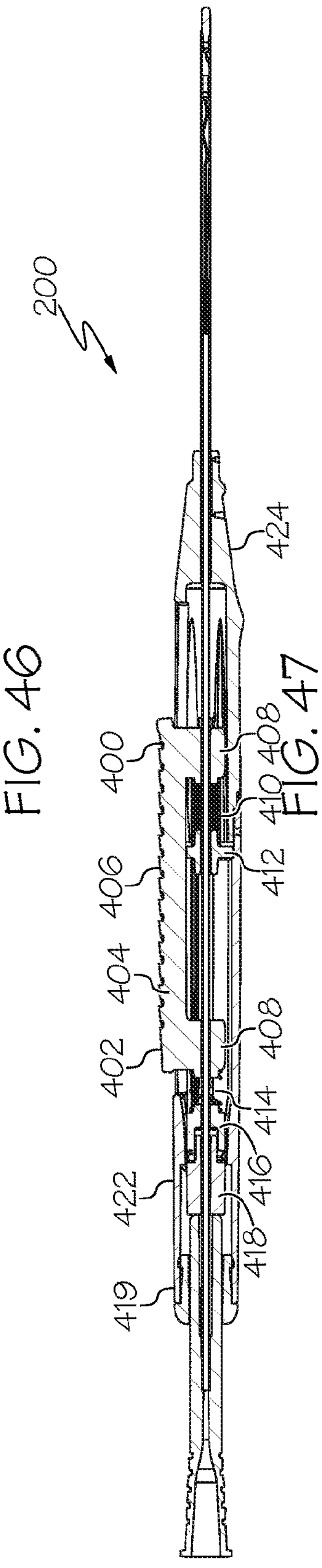
FIG. 47 is a side sectional view of the magnet-assisted suture grasper of FIG. 45, viewed along the cutting plane shown in FIG. 46.
Figure 48:
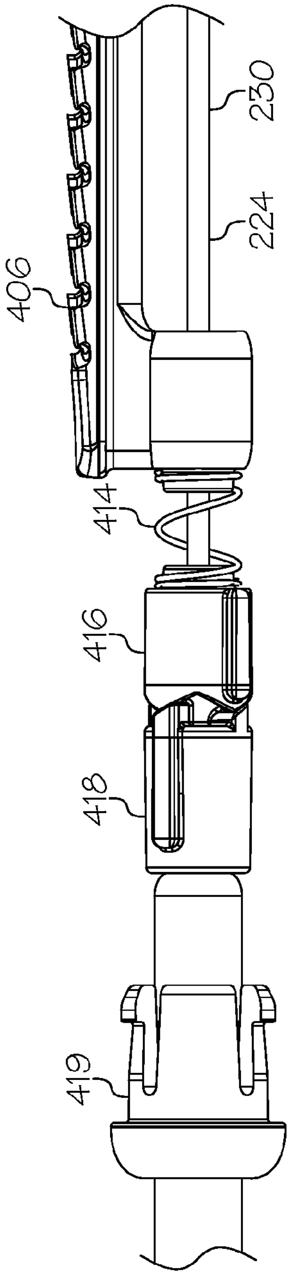
FIG. 48 is a side view of a lock cam, a drive cam, a cam spring, a carrier, a luer, a cap bushing, and the retriever body of the magnet-assisted suture grasper of FIG. 45.
Figure 49:
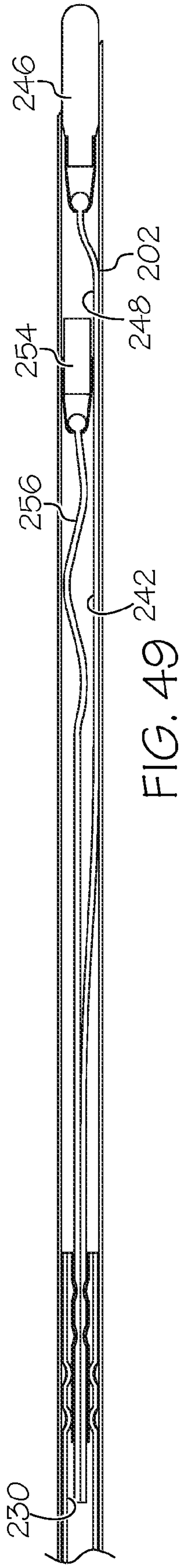
FIG. 49 is an expanded side sectional view of the suture retrieval needle, the retriever body, the grasper ferrule, the grasper member, the grasper magnet, and the magnet wire of the magnet-assisted suture grasper of FIG. 45, viewed along the cutting plane shown in FIG. 46.
Figure 50:
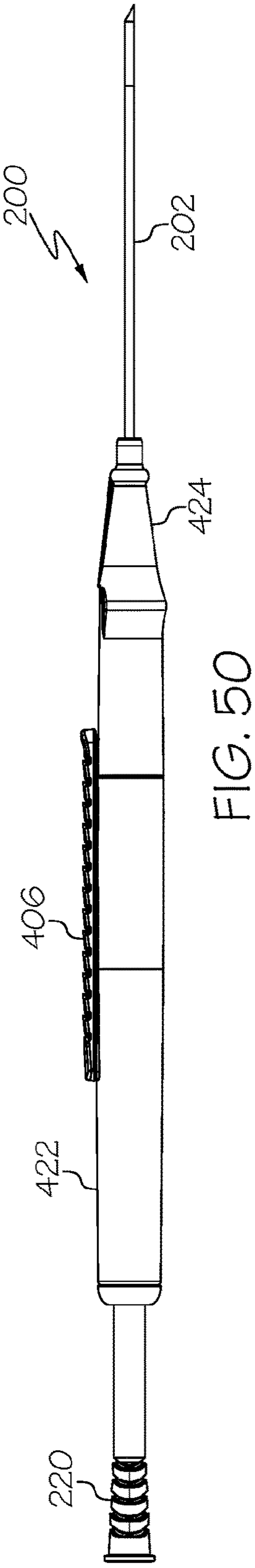
FIG. 50 is a side view of the magnet-assisted suture grasper of FIG. 1, in which the advancer assembly is in an unlocked fully retracted position.
Figure 51:
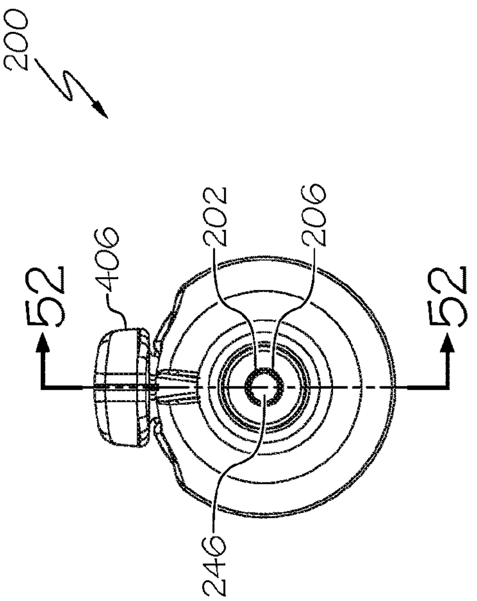
FIG. 51 is a front view of the magnet-assisted suture grasper of FIG. 50.
Figure 52:
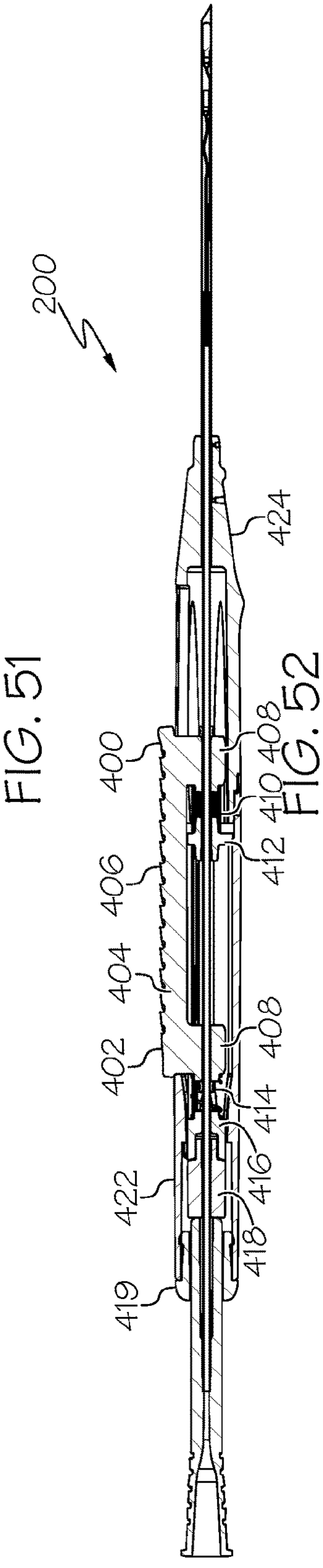
FIG. 52 is a side sectional view of the magnet-assisted suture grasper of FIG. 50, viewed along the cutting plane shown in FIG. 51.
Figure 53:
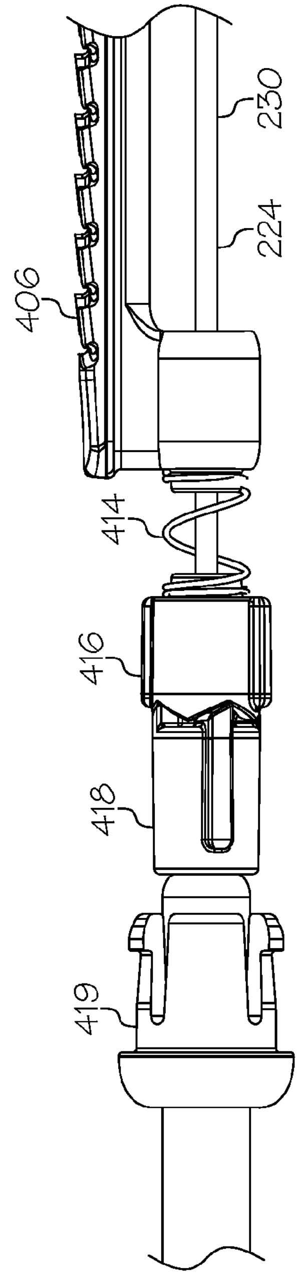
FIG. 53 is a side view of a lock cam, a drive cam, a cam spring, a carrier, a luer, a cap bushing, and the retriever body of the magnet-assisted suture grasper of FIG. 50.
Figure 54:
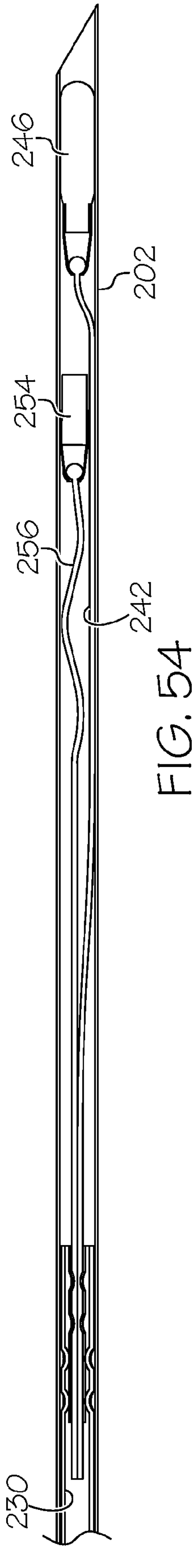
FIG. 54 is an expanded side sectional view of the suture retrieval needle, the retriever body, the grasper ferrule, the grasper member, the grasper magnet, and the magnet wire of the magnet-assisted suture grasper of FIG. 50, viewed along the cutting plane shown in FIG. 51.
Figure 55:
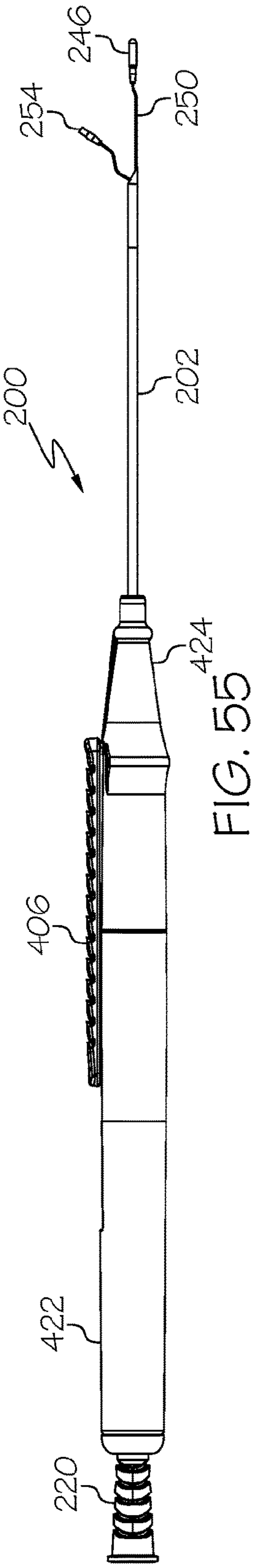
FIG. 55 is a side view of the magnet-assisted suture grasper of FIG. 1, in which the advancer assembly is in a locked extended position, the grasper member is in the second position, and the grasper magnet is exposed from the suture retrieval needle.
Figure 56:
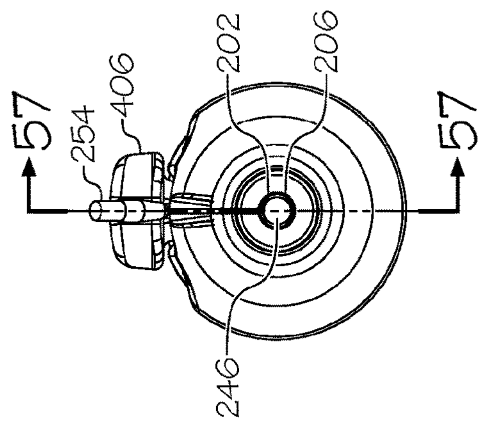
FIG. 56 is a front view of the magnet-assisted suture grasper of FIG. 55.
Figure 57:
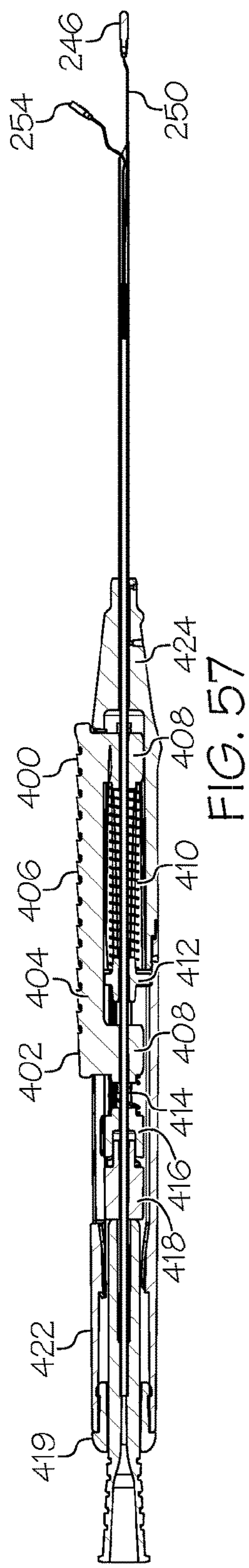
FIG. 57 is a side sectional view of the magnet-assisted suture grasper of FIG. 55, viewed along the cutting plane shown in FIG. 56.
Figure 58:
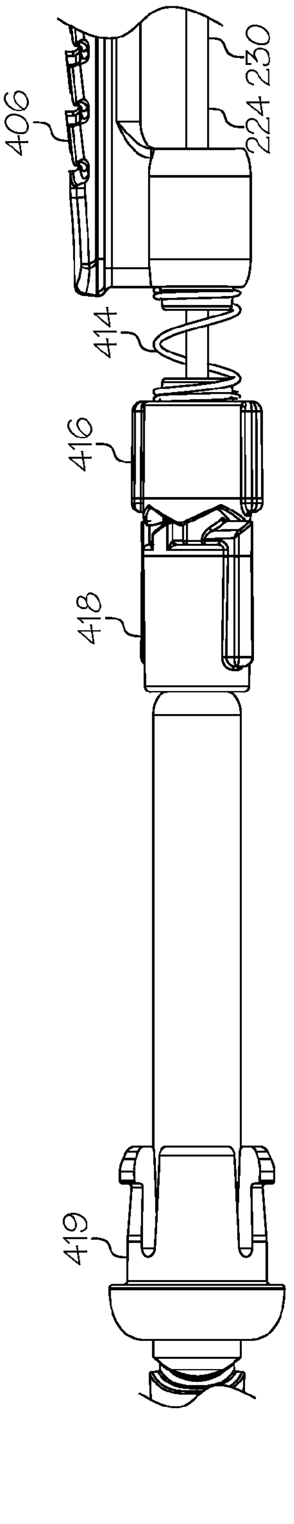
FIG. 58 is a side view of a lock cam, a drive cam, a cam spring, a carrier, a luer, a cap bushing, and the retriever body of the magnet-assisted suture grasper of FIG. 55.

The outer crimp joint 286 can be made with an interrupted crimping pattern 288, as shown in FIG. 32. This can be accomplished by use of a crimp tool including one or more distinct segments, also termed teeth, with gaps therebetween. The resulting crimp joint includes gaps between locally yielded areas of the grasper ferrule 268 and the retriever body 224 that provide paths 289 to allow liquids and gasses to flow through the crimp joint, as shown in FIG. 35.

In other approaches, the inner crimp joint 284 may be omitted when the outer crimp joint 286 is made with a depth of crimp sufficient to deform the grasper ferrule 268 deeply enough to capture the grasper member 242 and the magnet wire 256. This allows for assembly of the relevant parts in a single step, followed by crimping of the retriever body 224 onto the grasper ferrule 268 to join all relevant parts by the outer crimp joint 286.

Also in other approaches, the grasper ferrule 268, the elongated proximal-to-intermediate portion 244 of the grasper member 242, and the proximal portion 258 of the magnet wire 256 is inserted into the retriever body 224, e.g., into the retriever tube lumen 238 or the retriever body cavity 240 via the distal hole 236 with the elongated proximal-to-intermediate portion 244 of the grasper member 242 and the proximal portion 258 of the magnet wire 256 being disposed adjacent the grasper ferrule 268 and not within the ferrule lumen 280 of the grasper ferrule 268. The retriever body 224 is then crimped onto the grasper ferrule 268, the elongated proximal-to-intermediate portion 244 of the grasper member 242, and the proximal portion 258 of the magnet wire 256 to join the parts by the outer crimp joint 286, again omitting the inner crimp joint 284. In these approaches, the grasper ferrule 268 is included to help control the depth of the crimp. This can provide advantages in terms of maintaining a relatively larger open cross-sectional area within the outer crimp joint 286.

Also in other approaches, a swaged joint or an uninterrupted crimp may allow for a heavier depth of crimp, with less undesirable deformation, i.e. off-axis deflection, than can be achieved with an interrupted crimp. The benefit of a heavier depth of crimp is that it generally provides for a stronger joint.

By applying one or more grooves or projections to the inner diameter of the retriever tube lumen 238 or retriever body cavity 240 or outer diameter of the grasper ferrule 268, a flow path can be created through the swaged joint or the uninterrupted crimp.

Also in other approaches, the grasper ferrule subassembly 282 can be made by creating an inner crimp joint 284 as described above, the grasper ferrule subassembly 282 can be inserted into the retriever body 224 also as described above, and then the grasper ferrule 268 can be fixedly attached to the retriever tube 230 by approaches other than crimping, such as welding.

Thus, in some embodiments, the grasper ferrule 268 has been crimped onto the grasper member 242 and the magnet wire 256 with the elongated proximal-to-intermediate portion 244 of the grasper member 242 and the proximal portion 258 of the magnet wire 256 being disposed within the ferrule lumen 280 of the grasper ferrule 268; and the retriever body 230 has been crimped onto the grasper ferrule 268 with the grasper ferrule 268, the elongated proximal-to-intermediate portion 244 of the grasper member 242, and the proximal portion 258 of the magnet wire 256 being disposed within the retriever body 224.

Also in some embodiments, the retriever body 224 has been crimped onto the grasper ferrule 268, the elongated proximal-to-intermediate portion 244 of the grasper member 242, and the proximal portion 258 of the magnet wire 256, with the grasper ferrule 268, the elongated proximal-to-intermediate portion 244 of the grasper member 242, and the proximal portion 258 of the magnet wire 256 being disposed within the retriever body 224, and with the elongated proximal-to-intermediate portion 244 of the grasper member 242 and the proximal portion 258 of the magnet wire 256 being disposed adjacent the grasper ferrule 268 and not within the ferrule lumen 280 of the grasper ferrule 268.

Also in some embodiments, the grasper magnet 254 is fixedly attached to the elongated proximal-to-intermediate portion 244 of the grasper member 242, either directly or indirectly. In these embodiments, translation of the grasper member 242 also results in translation of the magnet wire 256, and thus also the grasper magnet 254.

Figure 7:
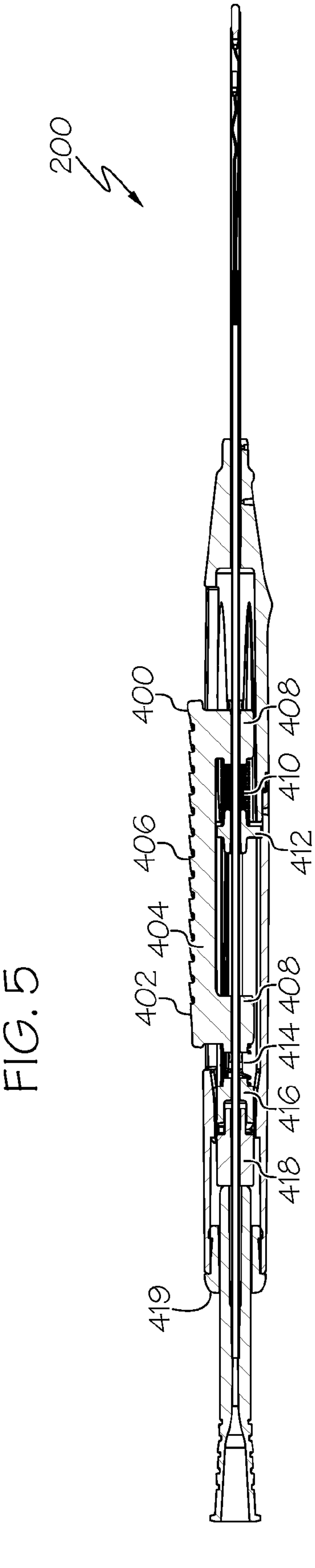
FIG. 7 is a side sectional view of the magnet-assisted suture grasper of FIG. 1, viewed along the cutting plane shown in FIG. 5.

As shown in FIG. 7, with reference to FIGS. 64-67, the magnet-assisted suture grasper 200 also comprises a spring 410 that allows the grasper member 242 to move reversibly further in a second direction as described below from the first position 248 upon pushing contact in the second direction at the enlarged distal terminus 246 of the grasper member 242 and that returns the grasper member 242 to the first position 248 upon cessation of the pushing contact. This is discussed in detail below.

As shown in FIG. 8 and FIG. 16, the enlarged distal terminus 246 of the grasper member 242 extends further distally than the grasper magnet 254. This means that when the grasper member 242 is in the first position 248 that the enlarged distal terminus 246 of the grasper member 242 extends further distally within the needle lumen 216 than does any portion of the grasper magnet 254. This also means that when the grasper member 242 is in the second position 250 that the enlarged distal terminus 246 of the grasper member 242 extends further distally from the suture retrieval needle 202 than does any portion of the grasper magnet 254. This also means that when the grasper member 242 is in the second position 250 that the grasper magnet 254 is closer to the distal end 206 of the suture retrieval needle 202 than is the enlarged distal terminus 246 of the grasper member 242.

With reference to FIG. 8, FIG. 16, and FIGS. 60-63, translation of the retriever body 224 within the needle lumen 216 in a first direction along the needle body axis 210 causes the grasper member 242 to move from the first position 248 to the second position 250, thereby exposing the grasper magnet 254 and allowing contact between the grasper magnet 254 and a magnetic suture 500 attracted thereto. The translation of the retriever body 224 results in translation of the grasper member 242. The translation of the retriever body 224 in the first direction can be translation of the retriever body 224 within the needle lumen 216 in a direction from the proximal end 204 of the suture retrieval needle 202 toward the distal end 206 of the suture retrieval needle 202. When the grasper member 242 is in the first position 248 the grasper magnet 254 can be disposed entirely inside the needle lumen 216, and thus sequestered within the needle lumen 216. In accordance with these embodiments, such translation of the retriever body 224 within the needle lumen 216 in the first direction can move the grasper magnet 254 from inside the needle lumen 216 to outside the needle lumen 216, thus exposing the grasper magnet 254.

The grasper member 242 is made to be sufficiently stiff so that translation of the retriever body 224 within the needle lumen 216 in the first direction moves the grasper member 242 from inside the needle lumen 216 to outside the needle lumen 216, thus exposing the grasper magnet 254.

Translation of the retriever body 224 within the needle lumen 216 in a second direction opposite the first direction along the needle body axis 210 causes the grasper member 242 to move from the second position 250 to the first position 248, thereby sequestering the grasper magnet 254 and grasping the magnetic suture 500 within the needle lumen 216. The translation of the retriever body 224 in the second direction can be translation of the retriever body 224 within the needle lumen 216 in a direction from the distal end 206 of suture retrieval needle 202 toward the proximal end 204 of the suture retrieval needle 202. Such translation of the retriever body 224 within the needle lumen 216 in the second direction can move the grasper magnet 254 from outside the needle lumen 216 to inside the needle lumen 216, thus sequestering the grasper magnet 254 again and grasping the magnetic suture 500 within the needle lumen 216.

This can be accomplished as follows. Because the grasper magnet 254 is closer to the distal end 206 of the suture retrieval needle 202 than is the enlarged distal terminus 246 of the grasper member 242 while the grasper member 242 is in the second position 250, when a suture magnet 502 of a magnetic suture 500 contacts the grasper magnet 254 and the retriever body 224 is translated in the second direction to the first position 248, the grasper magnet 254 and the suture magnet 502 of the magnetic suture 500 enter the needle lumen 216 before the enlarged distal terminus 246 of the grasper member 242 does. Once the enlarged distal terminus 246 of the grasper member 242 has followed the suture magnet 502 into the needle lumen 216, the suture magnet 502 cannot exit the needle lumen 216 while the enlarged distal terminus 246 of the grasper member 242 remains in the needle lumen 216. The grasper member 242 blocks exit of the suture magnet 502, thereby mechanically capturing the magnetic suture 500. The suture magnet 502 of the magnetic suture 500 thus can be grasped by the grasper member 242 as the magnet-assisted suture grasper 200 is used to pull the magnetic suture 500 through soft tissue of a patient. The grasper member 242 is sufficiently strong to resist the frictional drag that results from pulling the magnetic suture 500 through the soft tissue.

As noted above, the grasper member 242 comprises an elongated proximal-to-intermediate portion 244 and an enlarged distal terminus 246. Also as noted, the grasper magnet 254 is disposed adjacent the elongated proximal-to-intermediate portion 244 of the grasper member 242. The grasper member 242 has a length and orientation sufficient to allow the suture magnet 502 of a magnetic suture 500 to fit between the grasper magnet 254 and the enlarged distal terminus 246 of the grasper member 242 when the grasper member 242 is in the second position 250, so that the suture magnet 502 of the magnetic suture 500 can contact the grasper magnet 254 for magnetic attraction, and when the grasper member 242 has been returned to the first position 248, so that the suture magnet 502 of the magnetic suture 500 can fit within the needle lumen 216 along with the grasper magnet 254 and the grasper member 242 for mechanical capture. The elongated proximal-to-intermediate portion 244 of the grasper member 242 adjacent to which the grasper magnet 254 is disposed can be any portion of the grasper member 242 distal to the retriever body 224 and proximal to the enlarged distal terminus 246 of the grasper member 242, so long as sufficient space is provided for a suture magnet 502 to fit between the grasper magnet 254 and the enlarged distal terminus 246 of the grasper member 242.

In some embodiments, translation of the retriever body 224 within the needle lumen 216 is limited to a straight path as the translation of the retriever body 224 causes the grasper member 242 to move between the first position 248 and the second position 250. As noted above, in some embodiments, the suture retrieval needle 202 includes a curve at or near its distal end 206 but otherwise is straight. Limiting translation of the retriever body 224 within the needle lumen 216 to a straight path as the translation of the retriever body 224 causes the grasper member 242 to move between the first position 248 and the second position 250 can be advantageous because it allows use of a retriever body 224 that is made of a rigid material, such as stainless steel, while also allowing use of a suture retrieval needle 202 that includes a curve at or near its distal end 206 but otherwise is straight. In accordance with these embodiments, the grasper member 242 and the magnet wire 256 can be made to sufficient lengths and with sufficient flexibilities to pass through the needle lumen 216 at the curve of the suture retrieval needle 202 without the retriever body 224 needing to do so.

Figure 60:
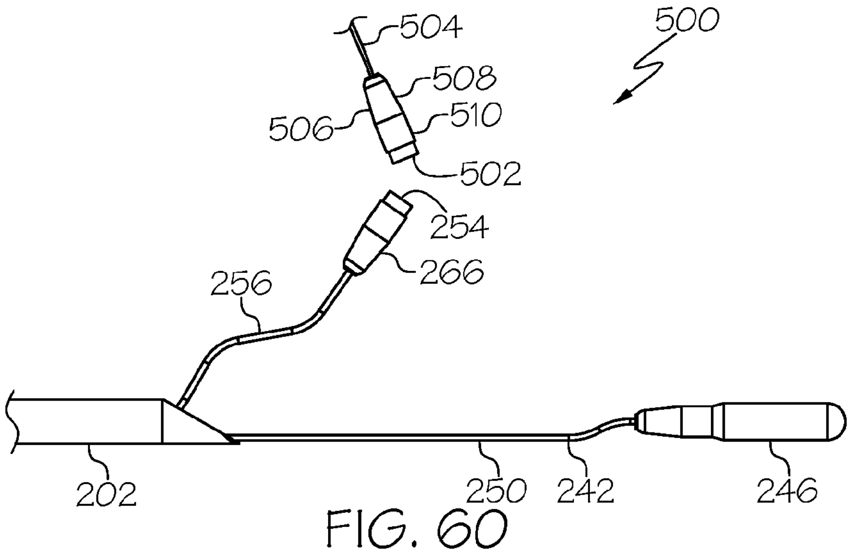
FIG. 60 is a side view of a distal portion of the magnet-assisted suture grasper of FIG. 1, in which the advancer assembly is in the locked extended position, the grasper member is in the second position exposing the grasper magnet from the suture retrieval needle, and the grasper magnet is attracting a magnetic suture.

Considering the grasper member 242 in more detail, as shown in FIG. 24 and FIG. 60, in some embodiments the elongated proximal-to-intermediate portion 244 of the grasper member 242 comprises a grasper wire 292 having a proximal end 294 and a distal end 296. In these embodiments, the grasper wire 292 is fixedly disposed within the retriever body 224 and extends distally therefrom. The enlarged distal terminus 246 extends distally from the distal end 296 of the grasper wire 292 and is reversibly moveable between the first position 248 and the second position 250. The grasper magnet 254 is disposed adjacent the grasper wire 292.

The grasper wire 292 is preferentially made from Nitinol with an austenitizing temperature below room temperature, so as to take advantage of the pseudo-elastic nature of the material for recovery of large elastic strains. Other metals, such as stainless steel, or polymeric materials, such as nylon or polyester, also can be used. The wire cross-section is preferentially round, but other cross-sections would work as well, such as square, rectangular, triangular, or obround.

The enlarged distal terminus 246 also can be made of these metals or polymeric materials.

In some embodiments, the enlarged distal terminus 246 can be attached to the grasper wire 292 based on direct adhesion or through one, two, or more intermediate parts, such as a ferrule, a ring, or a sleeve, among other intermediate parts.

Alternatively, the enlarged distal terminus 246 can be integral to the grasper wire 292. By this it is meant that the enlarged distal terminus 246 and the grasper wire 292 can be adjacent portions of a single segment of wire from which the grasper wire 292 and the enlarged distal terminus 246 have been formed.

The grasper member 242 comprising the grasper wire 292 and the enlarged distal terminus 246 can be provided in various configurations.

Figure 68:
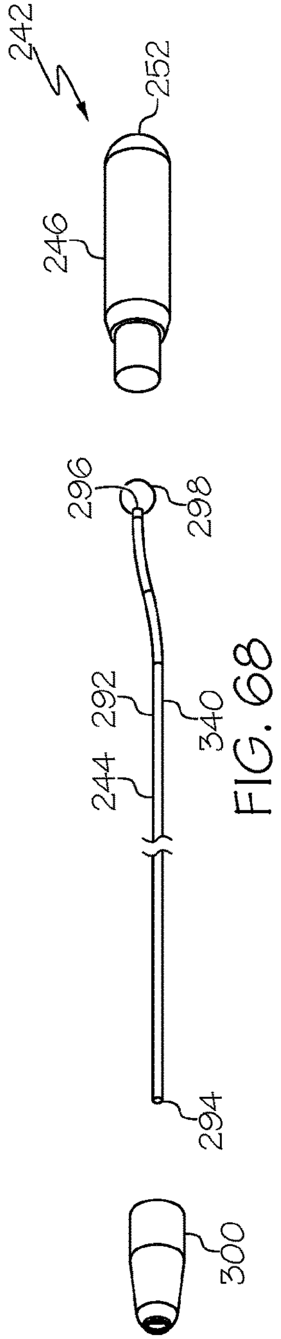
FIG. 68 is an exploded side view of a first example embodiment of the grasper member of the magnet-assisted suture grasper of FIG. 1, in which the elongated proximal-to-intermediate portion of the grasper member comprises a grasper wire comprising a grasper wire proximal end, a grasper wire distal terminus, and a grasper wire body therebetween, and the enlarged distal terminus of the grasper member comprises a grasper probe, and the grasper member further comprises an intermediary ferrule. The grasper probe can be joined to the grasper wire at the grasper wire distal terminus using the intermediary ferrule.
Figure 70:
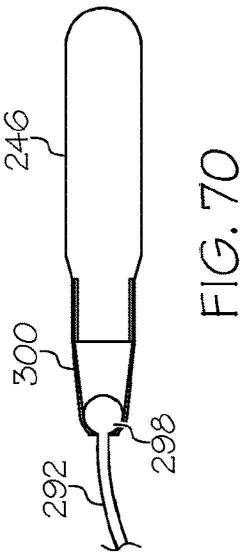
FIG. 70 is an expanded side sectional view of the first example embodiment of the grasper member of the magnet-assisted suture grasper of FIG. 68, viewed along the cutting plane shown in FIG. 69.
Figure 69:
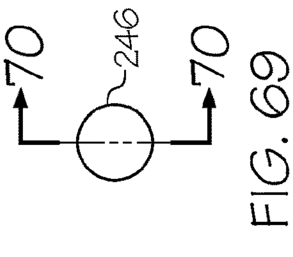
FIG. 69 is a front view of the first example embodiment of the grasper member of the magnet-assisted suture grasper of FIG. 68.
Figure 71:
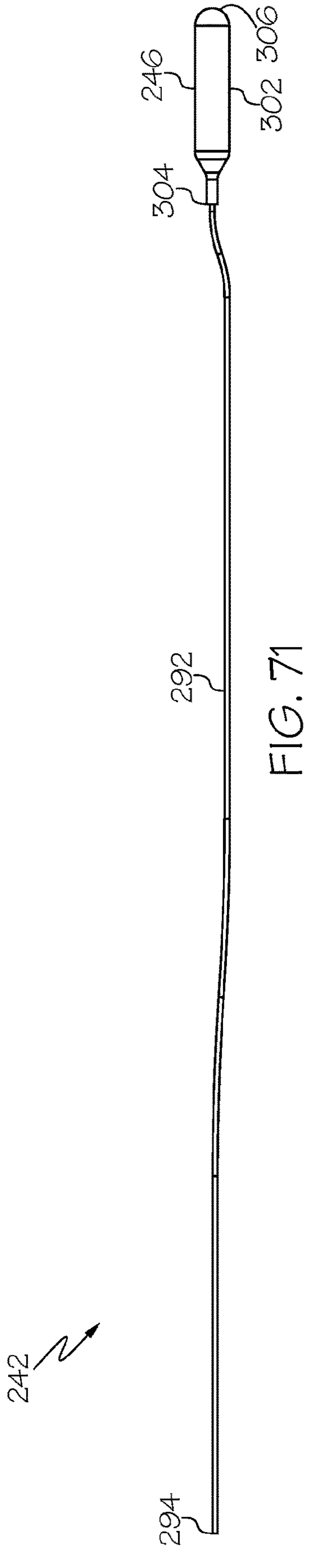
FIG. 71 is side view of a second example embodiment of the grasper member of the magnet-assisted suture grasper of FIG. 1, in which the elongated proximal-to-intermediate portion of the grasper member comprises a grasper wire comprising a grasper wire proximal end, a grasper wire distal terminus, and a grasper wire body therebetween, and the enlarged distal terminus of the grasper member comprises a combined ferrule-grasper probe having a proximal opening, a proximal tapered ferrule portion, a distal probe portion, and an intermediate slot adjacent the proximal tapered portion. The proximal opening and the intermediate slot are in fluid communication within the combined ferrule-grasper probe. The combined ferrule-grasper probe can be joined to the grasper wire at the grasper wire distal terminus by feeding the grasper wire proximal end and grasper wire body through the intermediate slot and the proximal opening of the combined ferrule-grasper probe until the grasper wire distal terminus is seated in the proximal tapered ferrule portion within the combined ferrule-grasper probe.
Figure 72:
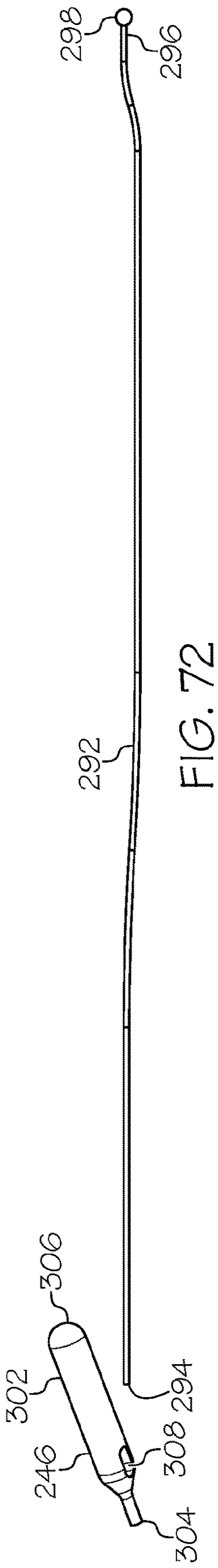
FIG. 72 is a perspective view of the grasper wire and the enlarged distal terminus of the second example embodiment of the grasper member of FIG. 71.
Figure 73:
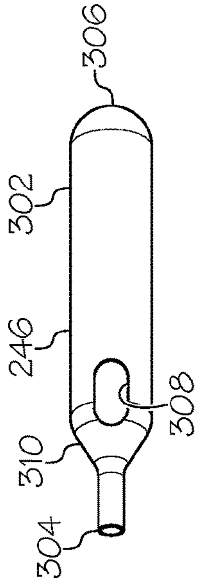
FIG. 73 is a bottom view of the enlarged distal terminus of the second example embodiment of the grasper member of FIG. 71.
Figure 74:
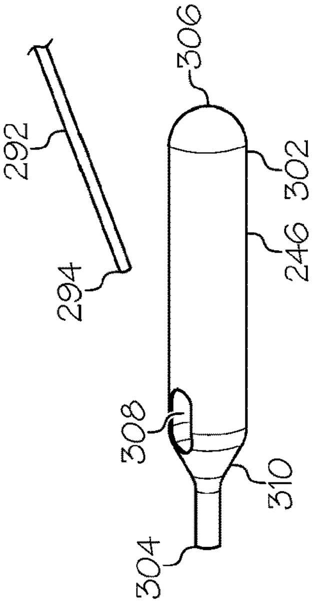
FIG. 74 is a perspective view of the proximal end of the grasper wire and the enlarged distal terminus of the second example embodiment of the grasper member of FIG. 71.
Figure 76:
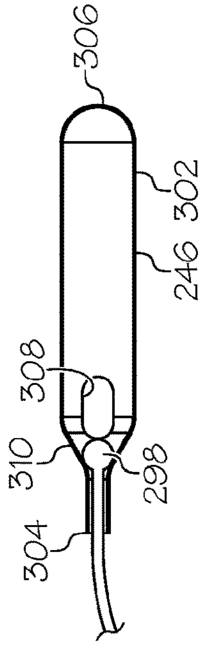
FIG. 76 is a side sectional view of the second example embodiment of the grasper member of FIG. 71, in which the grasper wire distal terminus of the grasper wire is seated in the tapered portion of the combined ferrule-grasper probe, viewed along the cutting plane shown in FIG. 75.
Figure 75:
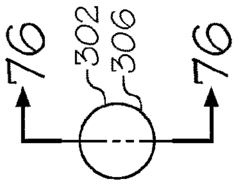
FIG. 75 is a front view of the second example embodiment of the grasper member of FIG. 71, in which the grasper wire distal terminus of the grasper wire is seated in the tapered portion of the combined ferrule-grasper probe.

One exemplary grasper member configuration is a tapered-ferrule grasper member configuration, as shown in FIGS. 68-70. In accordance with the tapered-ferrule grasper member configuration, the enlarged distal terminus 246 is joined to the grasper wire 292 by use of a tapered ferrule 300 similar to the magnet ferrule 266 as described herein. The enlarged distal terminus 246 can be secured to the tapered ferrule 300 by using adhesive, or by brazing, soldering, or crimping, among other approaches.

Another exemplary grasper member configuration is an extended-ferrule grasper member configuration, as shown in FIGS. 71-76. In this configuration, the enlarged distal terminus 246 and a ferrule are combined to form an extended ferrule 302. The extended ferrule 302 comprises a proximal end 304 sized to fit over the distal end 296 of the grasper wire 292 and a distal end 306 size to occlude the distal hole 214 of the needle body 208 of the suture retrieval needle 202. The distal end 306 of the extended ferrule 302 may be fully closed, as shown, partially closed, or fully open. The extended ferrule 302 can be made in a variety of shapes so long as the shape will be atraumatic to tissue under an applied load of around 0.25-6.4 N. The distal end 306 may be made atraumatic by providing a closed or semi-closed blunt end, as shown, or by softening the inside and outside edges of an open cylindrical end, for example by electropolishing, tumbling, blasting, or chamfering. In accordance with this configuration, the grasper wire 292 can include a grasper wire head 298 at the distal end 296 of the grasper wire 292. The grasper wire head 298 can have an outer diameter greater than an inner diameter of the proximal end 304 of the extended ferrule 302. If the distal end 306 of the extended ferrule 302 is partially or fully open, then the grasper wire 292 may be fed through the open end similarly as for assembly of the grasper magnet 254 and the magnet wire 256. If the distal end 306 of the extended ferrule 302 is made fully or partially closed, then an extended ferrule hole 308 is provided through which the grasper wire 292 can be fed. In either case, the extended ferrule 302 is pulled over the grasper wire 292 until the grasper wire head 298 is seated against a tapered portion 310 inside the extended ferrule 302 at the proximal end 304 of the extended ferrule 302. Adhesive is then applied through the extended ferrule hole 308 to permanently bond the extended ferrule 302 to the grasper wire 292 and fix the relative position of the two components. Alternatively, the extended ferrule 302 may be crimped, welded, brazed, or soldered to the grasper wire.

Figure 77:
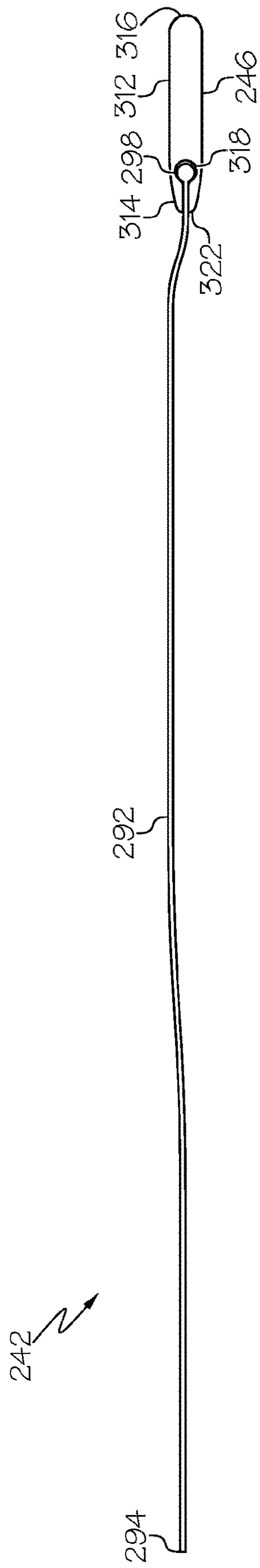
FIG. 77 is side view of a third example embodiment of the grasper member of the magnet-assisted suture grasper of FIG. 1, in which the elongated proximal-to-intermediate portion of the grasper member comprises a grasper wire comprising a grasper wire proximal end, a grasper wire distal terminus, and a grasper wire body therebetween, and the enlarged distal terminus of the grasper member comprises a self-retaining grasper probe having a proximal end, a proximal tapered portion, a distal probe portion, a pocket adjacent the proximal tapered portion, and a proximal slot extending from the proximal end to the pocket and forming a C-shaped channel with an undercut. The self-retaining grasper probe can be joined to the grasper wire at the grasper wire distal terminus by pressing the grasper wire distal terminus into the pocket and pressing the grasper wire body into the C-shaped channel of the slot.
Figure 78:
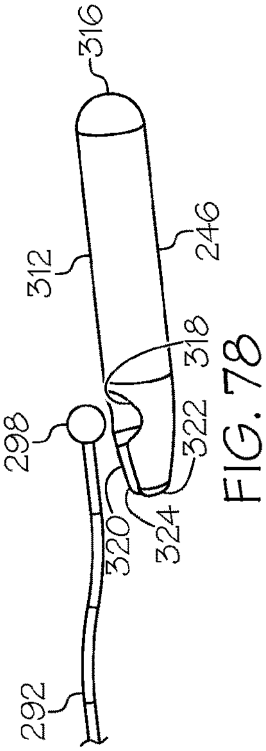
FIG. 78 is a perspective view of the distal end of the grasper wire including the grasper wire distal terminus and the enlarged distal terminus of the third example embodiment of the grasper member of FIG. 77.
Figure 79:
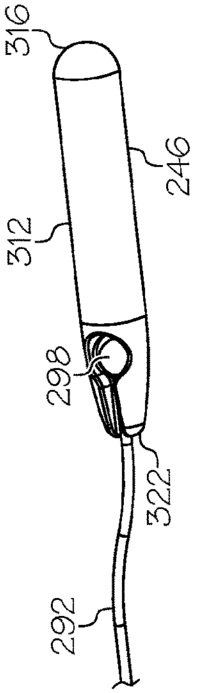
FIG. 79 is a perspective view of the distal end of the grasper wire including the grasper wire distal terminus and the enlarged distal terminus of the third example embodiment of the grasper member of FIG. 77, in which the grasper wire distal terminus of the grasper wire is seated in the pocket of the self-retaining grasper probe and the grasper wire body is seated in the C-shaped channel of the slot of the self-retaining grasper probe of the enlarged distal terminus.

Another exemplary grasper member configuration is a self-retaining-ferrule grasper member configuration. In this configuration, the enlarged distal terminus 246 and a ferrule again are combined, this time to form a self-retaining ferrule 312, as shown in FIGS. 77-79. The self-retaining ferrule 312 has a tapered proximal end 314 and a solid round distal end 316. The self-retaining ferrule 312 also has a pocket 318 located near the tapered proximal end 314 into which a grasper wire head 298 fits. The self-retaining ferrule 312 also has a slot 320 extending from a proximal end 322 of the self-retaining ferrule 312 to the pocket 318, forming a channel 324. The channel 324 can be C-shaped. The channel 324 is formed with an undercut, such that a portion of the channel 324 is narrower than an outer diameter of the grasper wire 292. The undercut makes the channel 324 self-retaining with respect to the grasper wire 292. As the grasper wire 292 is pressed through a narrow portion of the channel 324, the material surrounding the channel 324 is elastically deformed. Once the grasper wire 292 is past the narrow portion of the channel 324, the elastically strained material returns to its normal shape, and the grasper wire 292 is thus captured. The self-retaining ferrule 312 can be made using additive manufacturing processes, such as 3D printing, injection molding, etc., or subtractive manufacturing processes, such as machining, grinding, etc. The self-retaining nature allows the self-retaining ferrule 312 to be assembled without any additional processing steps or materials, and thus with no crimp, weld, or adhesive.

Figure 80:
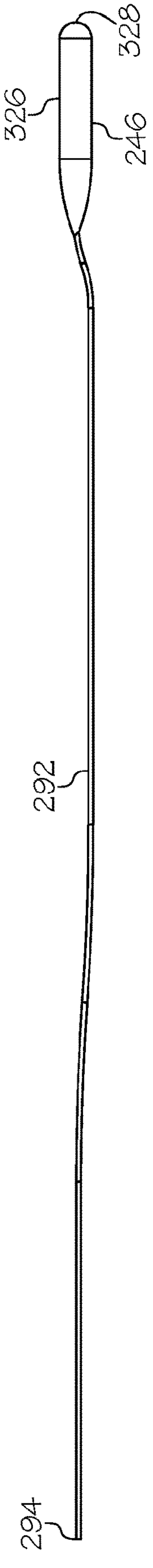
FIG. 80 is side view of a fourth example embodiment of the grasper member of the magnet-assisted suture grasper of FIG. 1, in which the elongated proximal-to-intermediate portion of the grasper member comprises a grasper wire comprising a grasper wire proximal end, a grasper wire distal terminus, and a grasper wire body therebetween, and the enlarged distal terminus of the grasper member comprises an overmolded grasper probe. The overmolded grasper probe can be joined to the grasper wire at the grasper wire distal terminus by an overmolding process.
Figure 82:
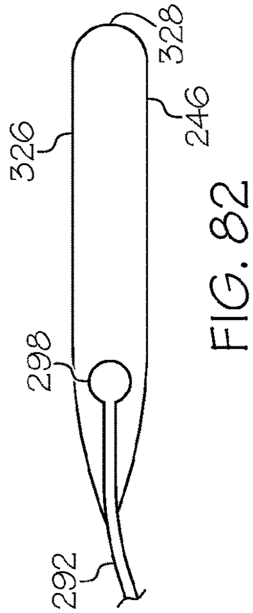
FIG. 82 is a side sectional view of the enlarged distal terminus of the fourth example embodiment of the grasper member of FIG. 80, viewed along the cutting plane shown in FIG. 81.
Figure 81:
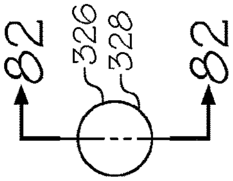
FIG. 81 is a front view of the fourth example embodiment of the grasper member of FIG. 80.
Figure 83:
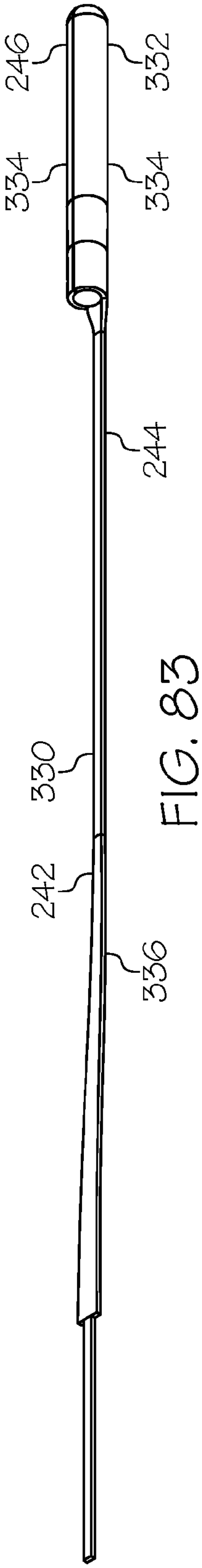
FIG. 83 is a perspective view of a fifth embodiment of the grasper member of the magnet-assisted suture grasper of FIG. 1, in which the grasper member is formed from a flat wire having a rectangular cross-section. The elongated proximal-to-intermediate portion of the grasper member has a major axis that is straight and a cross-sectional profile that is flat along the major axis. The enlarged distal terminus of the grasper member comprises a grasper probe formed by folding opposing first and second portions of the flat wire inwardly toward each other.
Figure 84:
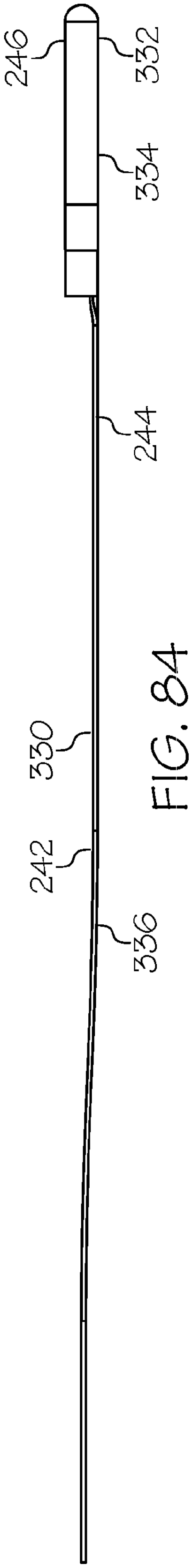
FIG. 84 is a side view of the fifth example embodiment of the grasper member of FIG. 83.
Figure 85:
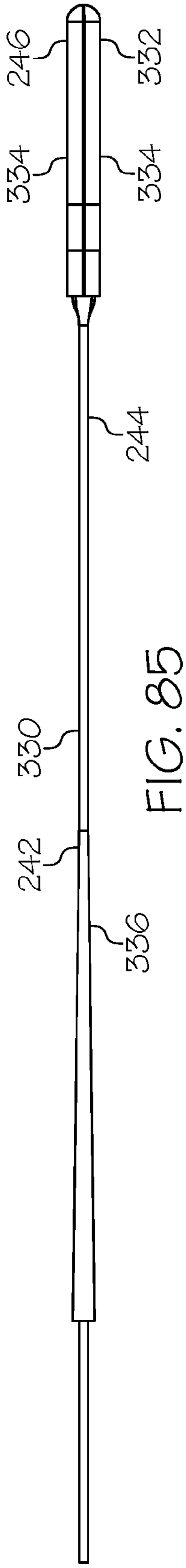
FIG. 85 is a top view of the fifth example embodiment of the grasper member of FIG. 83.
Figure 86:
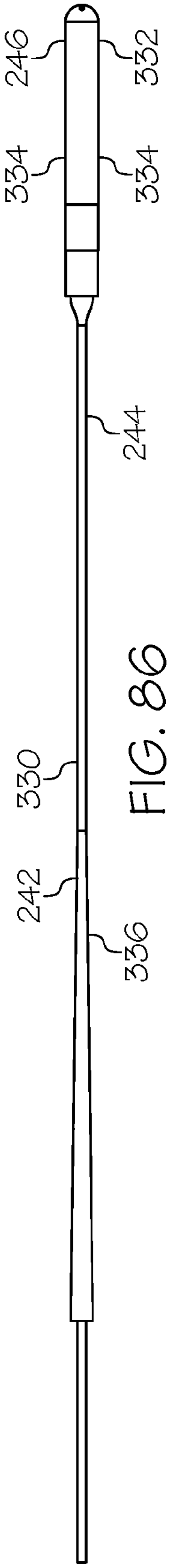
FIG. 86 is a bottom view of the fifth example embodiment of the grasper member of FIG. 83.
Figure 87:
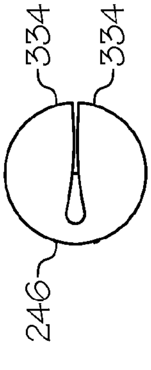
FIG. 87 is a front view of the fifth example embodiment of the grasper member of FIG. 83.
Figure 88:
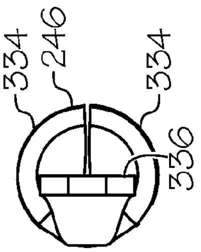
FIG. 88 is a back view of the fifth example embodiment of the grasper member of FIG. 83.
Figure 89:
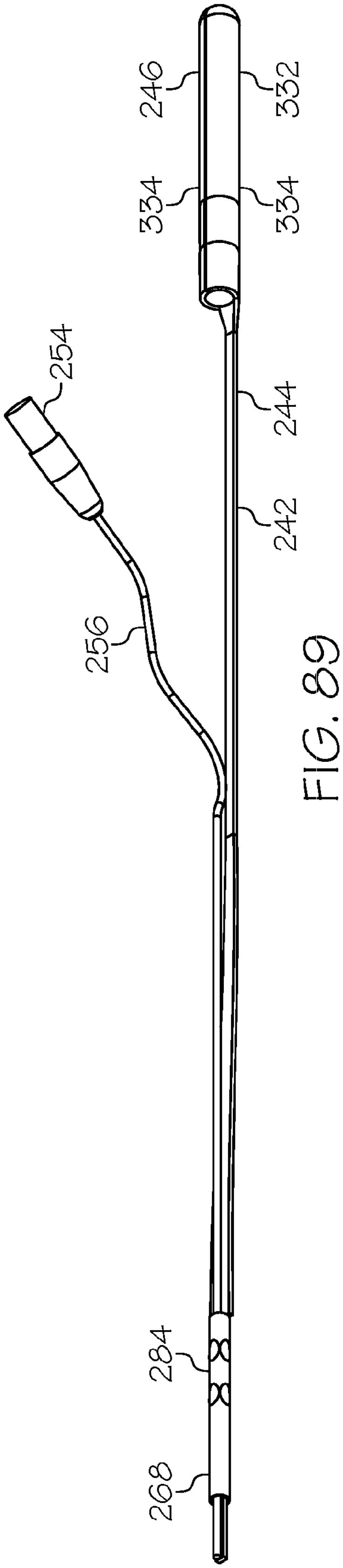
FIG. 89 is a perspective view of the fifth example embodiment of the grasper member of FIG. 83, and the grasper ferrule, the grasper magnet, and the magnet wire of the magnet-assisted suture grasper of FIG. 1, in which the grasper ferrule has been crimped onto the grasper member and the magnet wire.
Figure 90:
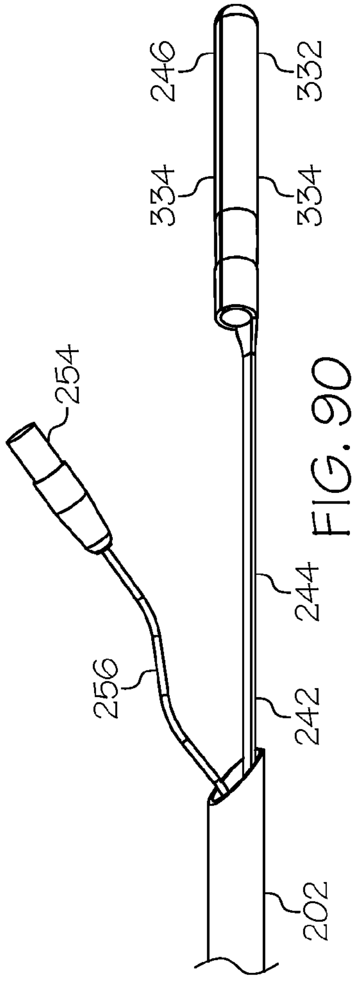
FIG. 90 is a perspective view of the fifth example embodiment of the grasper member of FIG. 83, and the suture retrieval needle, the grasper magnet, and the magnet wire of the magnet-assisted suture grasper of FIG. 1, in which the grasper member is in the second position exposing the grasper magnet from the suture retrieval needle.
Figure 91:
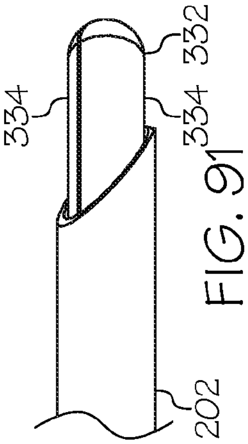
FIG. 91 is a perspective view of the fifth example embodiment of the grasper member of FIG. 83, and the suture retrieval needle of the magnet-assisted suture grasper of FIG. 1, in which the grasper member is in the first position sequestering the grasper magnet within the needle lumen.
Figure 92:
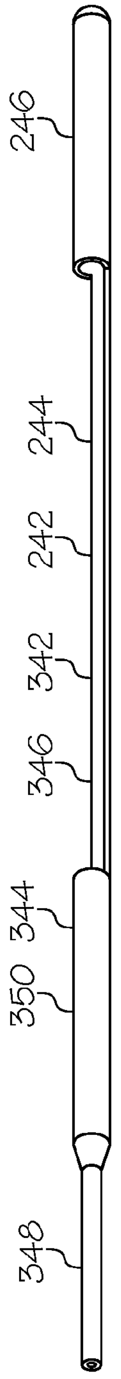
FIG. 92 is a perspective view of a sixth example embodiment of the grasper member of the magnet-assisted suture grasper of FIG. 1, in which the grasper member is formed from a cut tube, in which the elongated proximal-to-intermediate portion of the grasper member comprises a proximal cylindrical portion and an intermediate semicylindrical portion, and the enlarged distal terminus comprises a distal cylindrical portion.
Figure 93:
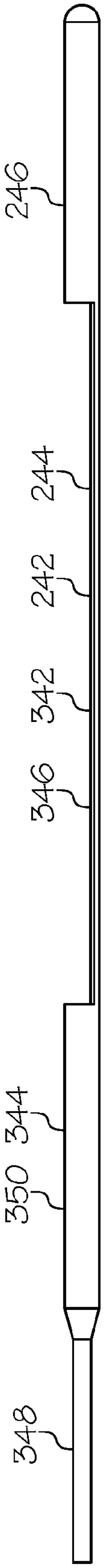
FIG. 93 is a side view of the sixth example embodiment of the grasper member of FIG. 92.
Figure 94:
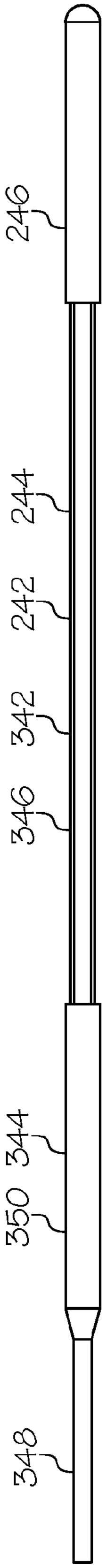
FIG. 94 is a top view of the sixth example embodiment of the grasper member of FIG. 92.
Figure 95:
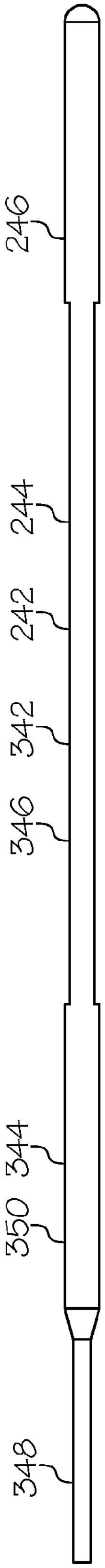
FIG. 95 is a bottom view of the sixth example embodiment of the grasper member of FIG. 92.
Figure 96:
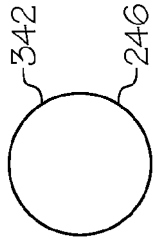
FIG. 96 is a front view of the sixth example embodiment of the grasper member of FIG. 92.
Figure 97:
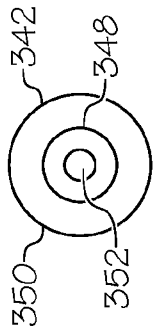
FIG. 97 is a back view of the sixth example embodiment of the grasper member of FIG. 92.
Figure 98:
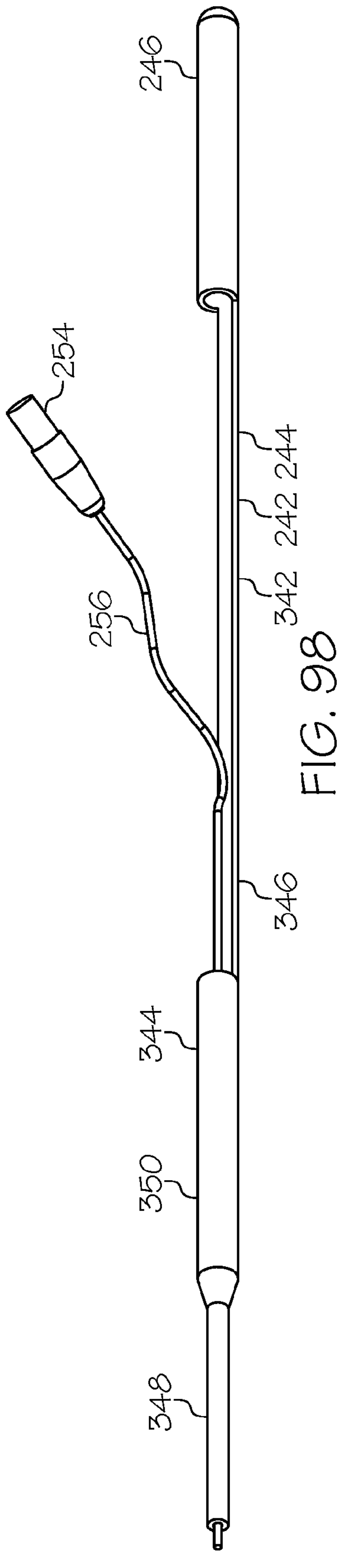
FIG. 98 is a perspective view of the sixth example embodiment of the grasper member of FIG. 92 and the grasper magnet and the magnet wire of the magnet-assisted suture grasper of FIG. 1, in which the proximal cylindrical portion of the elongated proximal-to-intermediate portion of the grasper member has been crimped onto the magnet wire.
Figure 99:
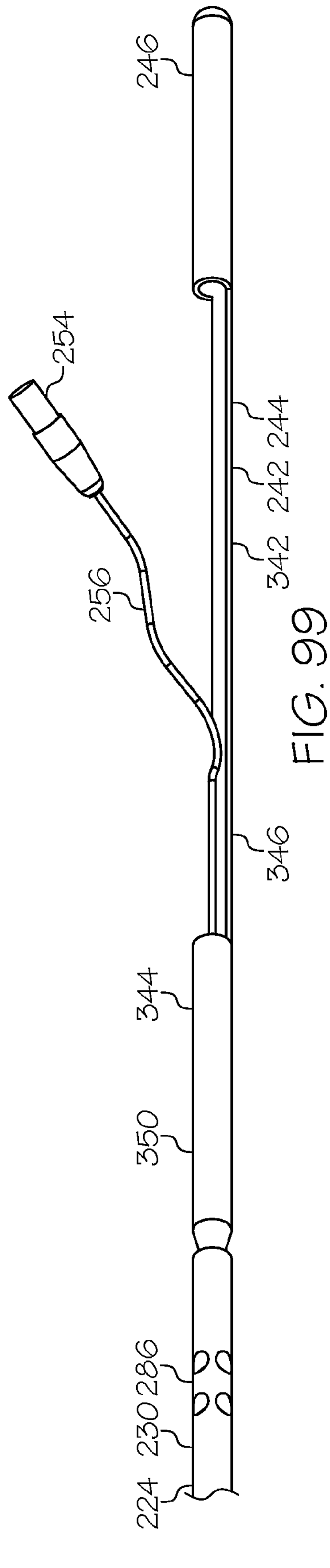
FIG. 99 shows a perspective view of the sixth example embodiment of the grasper member of FIG. 92 and the retriever body, the grasper magnet, and the magnet wire of the magnet-assisted suture grasper of FIG. 1, in which the retriever body has been crimped onto the proximal cylindrical portion of the elongated proximal-to-intermediate portion of the grasper member.
Figure 100:
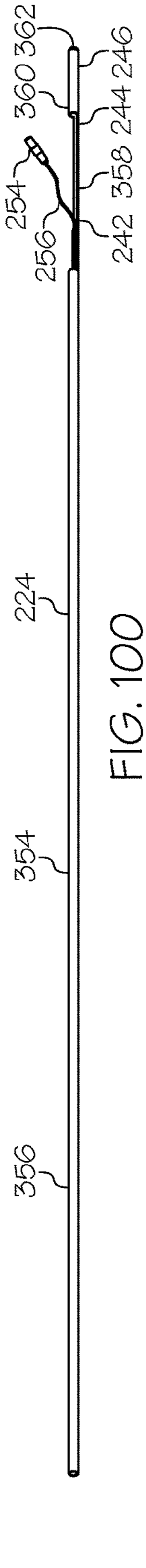
FIG. 100 is a perspective view of an example embodiment of a retriever body and a grasper member of the magnet-assisted suture grasper of FIG. 1, in which the retriever body and the grasper member are formed from a cut tube, and the grasper member is integral to the retriever body. Also shown are the grasper magnet and the magnet wire of the magnet-assisted suture grasper of FIG. 1. In this embodiment, a grasper ferrule (not shown in this view) is crimped onto the magnet wire, and the retriever body is crimped onto the grasper ferrule.
Figure 101:
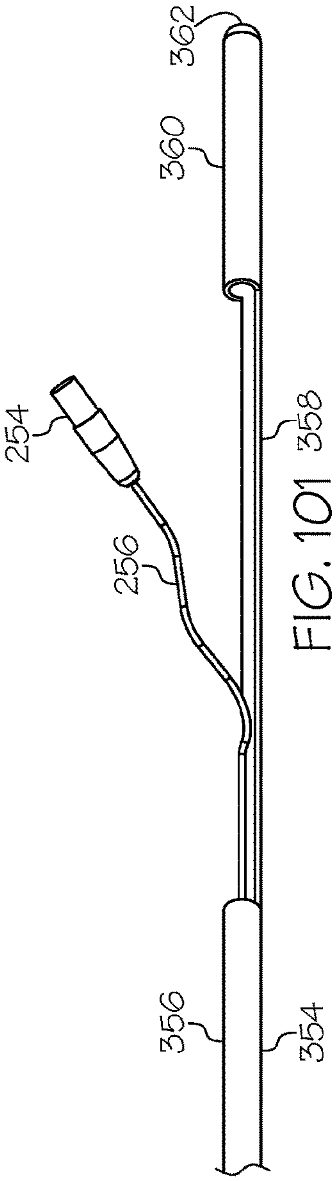
FIG. 101 is an expanded perspective view of the example embodiment of the retriever body and the grasper member of FIG. 100.
Figure 102:
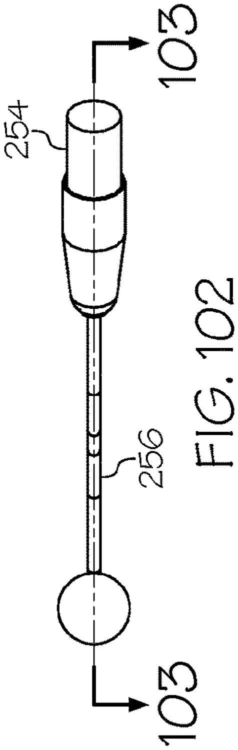
FIG. 102 is a front view of the example embodiment of the retriever body and the grasper member of FIG. 100.
Figure 103:
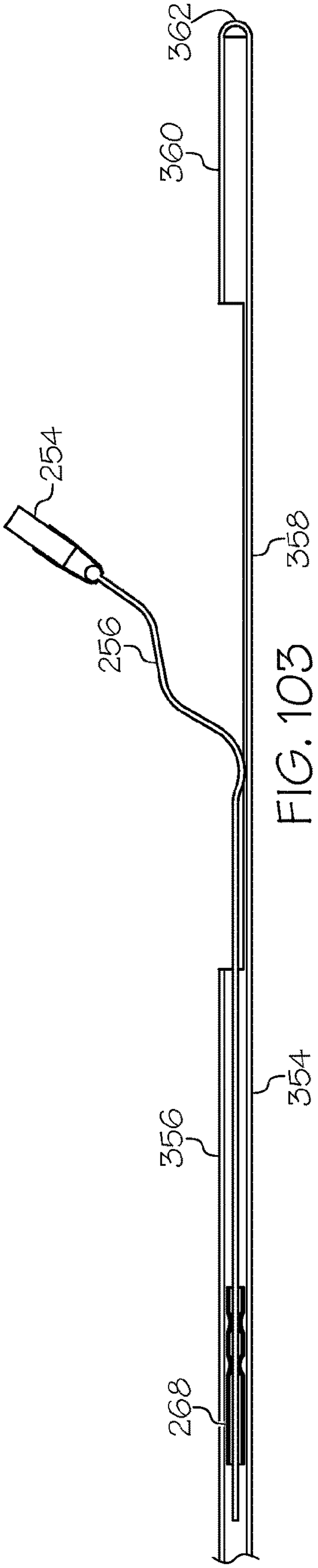
FIG. 103 is a side sectional view of the example embodiment of the retriever body and the grasper member of FIG. 100, here showing the grasper ferrule crimped onto the magnet wire and disposed within the retriever body, viewed along the cutting plane shown in FIG. 102.
Figure 104:
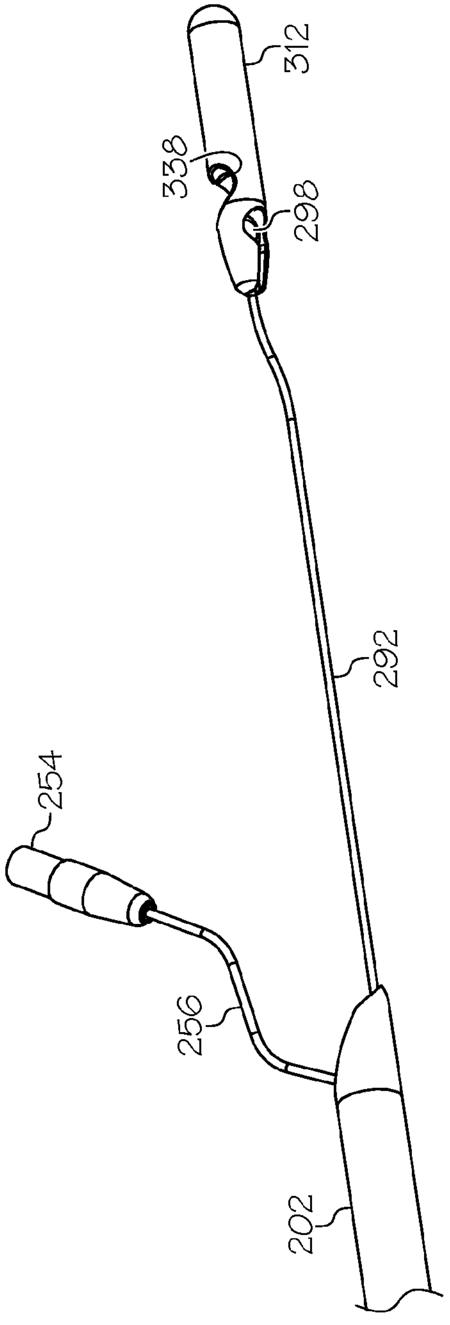
FIG. 104 is a perspective view of an alternative embodiment of the third example embodiment of the grasper member of FIG. 77, in which the self-retaining grasper probe includes a hook. The suture retrieval needle, the grasper magnet, and the magnet wire of the magnet-assisted suture grasper of FIG. 1 are also shown. The grasper member is in the second position exposing the grasper magnet from the suture retrieval needle.
Figure 105:
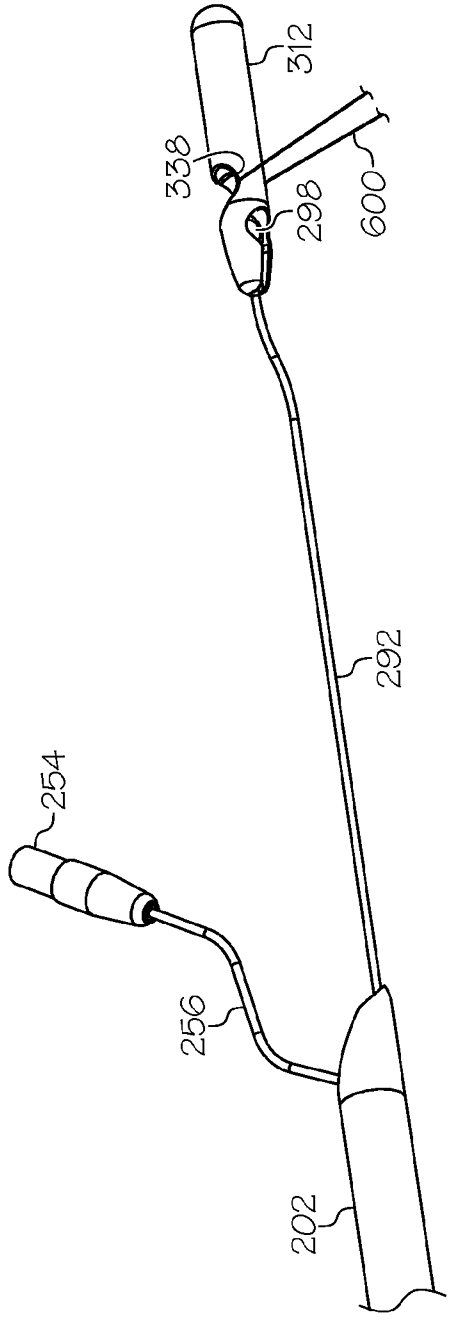
FIG. 105 is a perspective view of the alternative embodiment of the third example embodiment of the grasper member of FIG. 104, in which a suture has been captured on the hook of the self-retaining grasper probe. The suture retrieval needle, the grasper magnet, and the magnet wire of the magnet-assisted suture grasper of FIG. 1 are also shown. The grasper member is in the second position exposing the grasper magnet from the suture retrieval needle.
Figure 106:
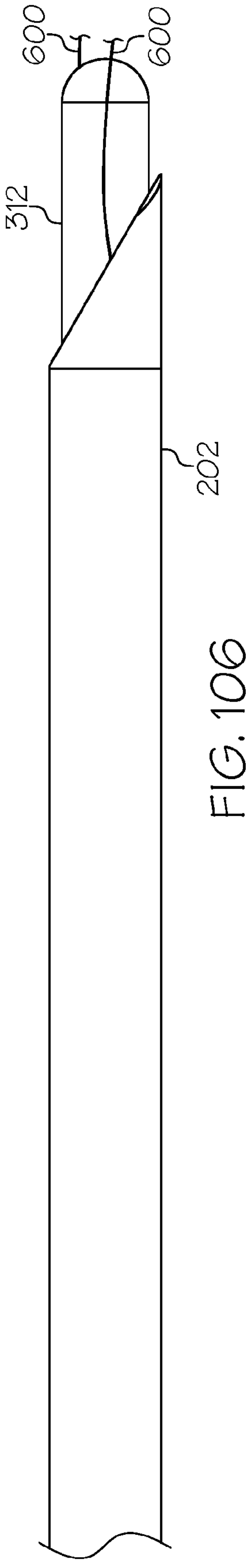
FIG. 106 is a side view of the alternative embodiment of the third example embodiment of the grasper member of FIG. 104. The suture retrieval needle is also shown. The grasper member is in the first position sequestering the grasper magnet and grasping the magnetic suture within the needle lumen.
Figure 107:
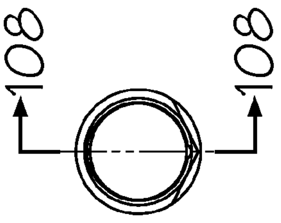
FIG. 107 is a front view of the alternative embodiment of the third example embodiment of the grasper member and the suture retrieval needle of FIG. 106.
Figure 108:
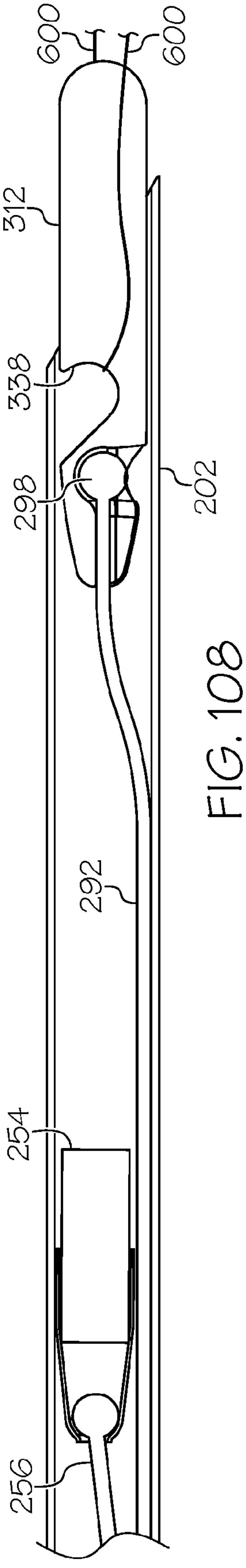
FIG. 108 is a side sectional view of the alternative embodiment of the third example embodiment of the grasper member and the suture retrieval needle of FIG. 106, also including the suture captured on the hook of the self-retaining grasper probe, viewed along the cutting plane shown in FIG. 107.

Another exemplary grasper member configuration is an over-molded-ferrule grasper member configuration, as shown in FIGS. 80-82. In this configuration, the enlarged distal terminus 246 and a ferrule again are combined, this time to form an over-molded ferrule 326. The over-molded ferrule has a distal end 328 that solid. The over-molded ferrule 326 can be made using an insert molding process, whereby a grasper wire head 298 and adjacent portion of a grasper wire 292 are placed into an empty cavity of an injection molding tool, and a polymeric or metal injection molding process is used to form the over-molded ferrule 326 directly onto the grasper wire 292. The grasper wire 292 is thereby permanently attached to the over-molded ferrule 326, and the assembly is completed in one step, with no further assembly or subsequent processing steps required.

Another exemplary grasper member configuration is a flat-wire grasper member configuration, as shown in FIGS. 83-91. In this configuration, the grasper wire 292 and the enlarged distal terminus 246 are formed from a single piece of flat wire 330 having a rectangular cross-section. The enlarged distal terminus 246 thus is integral to the grasper wire 292. The enlarged distal terminus 246 is formed from the flat wire 330 by folding a distal portion 332 of the flat wire 330 inwardly to form opposing first and second portions 334. This can be done using common metal forming techniques, such as stamping or coining. The grasper wire 292 corresponds to a remaining flat portion 336 of the flat wire 330. Because the enlarged distal terminus 246 is integral to the grasper wire 292, no assembly required.

Another exemplary grasper member configuration is an enlarged-distal-terminus-with-hook grasper member configuration, as shown in FIGS. 104-108. In any of the embodiments described above, a hook 338 may be incorporated into the enlarged distal terminus 246. The hook 338 can allow capture of a non-magnetic suture 600.

Accordingly, in some of these embodiments, the enlarged distal terminus 246 is reversibly moveable between the first position 248 and the second position 250 based on translation of the enlarged distal terminus 246 from partially inside of the needle lumen 216 to entirely outside of the needle lumen 216 through the distal hole 214 of the needle body 208. In these embodiments, the enlarged distal terminus 246 has a size sufficiently small to allow contact between the grasper magnet 254 and a suture magnet 502 of a magnetic suture 500 attracted thereto when the enlarged distal terminus 246 is in the second position 250 and to allow a suture 504 of the magnetic suture 500 to pass when the enlarged distal terminus 246 is in the first position 248. Also, the enlarged distal terminus 246 has a size sufficiently large to block the suture magnet 502 of the magnetic suture 500 from exiting the needle lumen 216 through the distal hole 214 of the needle body 208 when the enlarged distal terminus 246 is in the first position 248. In these embodiments, the enlarged distal terminus 246 prevents the magnetic suture 500 from being pulled out of the needle lumen 216 when the grasper member 242 is in the first position 248.

Also in some of these embodiments, the grasper wire 292 is formed from a round wire 340, and the enlarged distal terminus 246 is fixedly attached to the grasper wire 292.

Also in some of these embodiments, the grasper wire 292 and the enlarged distal terminus 246 are formed from a flat wire 330 having a rectangular cross-section. In these embodiments, the enlarged distal terminus 246 comprises opposing first and second portions 334 of the flat wire 330 that have been folded inwardly toward each other, thereby forming the enlarged distal terminus 246. In these embodiments, the enlarged distal terminus 246 is integral to the grasper wire 292.

Also in some of these embodiments, the enlarged distal terminus 246 comprises a hook 338. The hook 338 can allow capture of a non-magnetic suture 600.

Also in some of these embodiments, the enlarged distal terminus 246 fills 50% or more of an area of the distal hole 214 of the needle body 208 when the enlarged distal terminus 246 is in the first position 248.

Again considering the grasper member 242 in more detail, in some embodiments the elongated proximal-to-intermediate portion 244 and the enlarged distal terminus 246 are formed from a cut tube 342, as shown in FIGS. 92-99. In these embodiments, the elongated proximal-to-intermediate portion 244 comprises a proximal cylindrical portion 344 and an intermediate semi-cylindrical portion 346. The enlarged distal terminus 246 comprises a distal cylindrical portion. The proximal cylindrical portion 344 is fixedly attached to the retriever tube 230 and extends distally therefrom. The grasper magnet 254 is disposed adjacent the intermediate semi-cylindrical portion 344.

The grasper member 242 in which the elongated proximal-to-intermediate portion 244 and the enlarged distal terminus 246 are formed from a cut tube 342 can be provided in various configurations.

One exemplary grasper member configuration is a reduced-diameter-end cut tube configuration, as shown in FIGS. 92-99. In this configuration, the proximal cylindrical portion 344 has a proximal part 348 and a distal part 350, each having an outer diameter. The outer diameter of the proximal part 348 is smaller than the outer diameter of the distal part 350. The reduced-diameter-end cut tube configuration can be used with a retriever body 224 including a retriever tube lumen 238 or a retriever body cavity 240. The proximal part 348 of the proximal cylindrical portion 344 is used in place of a grasper ferrule 268 for fixedly attaching the magnet wire 256 to the grasper member 242 and attaching the grasper member 242 and the magnet wire 256 to the retriever body 224. The proximal part 348 includes a lumen 352 into which the magnet wire 256 fits. The proximal part 348 is sized to fit within a retriever tube lumen 238 or a retriever body cavity 240. For assembly, the magnet wire 256 is inserted into the lumen 352 of the proximal part 348. The proximal part 348 is crimped onto the magnet wire 256 to permanently join the magnet wire 256 to the grasper member 242. The proximal part 348 is then inserted into the retriever tube lumen 238 or the retriever body cavity 240. The retriever body 224 is then crimped onto the proximal part 348 to permanently join the grasper member 242 and the magnet wire 256 to the retriever body 224. Alternatively, the joints may be made by welding, brazing, adhesive, or other approaches.

The grasper member 242 in which the elongated proximal-to-intermediate portion 244 and the enlarged distal terminus 246 are formed from a cut tube 342 also can be provided in other configurations.

A hook 338 may be incorporated into the enlarged distal terminus 246 of these embodiments too, again to allow capture of a non-magnetic suture 600.

The resulting grasper member 242 in which the elongated proximal-to-intermediate portion 244 and the enlarged distal terminus 246 are formed from a cut tube 342 can then be used similarly as the grasper member 242 comprising the grasper wire 292 and the enlarged distal terminus 246 as described above.

Accordingly, in some of these embodiments, the enlarged distal terminus 246 is reversibly moveable between the first position 248 and the second position 250 based on translation of the enlarged distal terminus 246 from partially inside of the needle lumen 216 to entirely outside of the needle lumen 216 through the distal hole 214 of the needle body 208. In these embodiments, the enlarged distal terminus 246 has a size sufficiently small to allow contact between the grasper magnet 254 and a suture magnet 502 of a magnetic suture 500 attracted thereto when the enlarged distal terminus 246 is in the second position 250 and to allow a suture 504 of the magnetic suture 500 to pass when the enlarged distal terminus 246 is in the first position 248. Also, the enlarged distal terminus 246 has a size sufficiently large to block the suture magnet 502 of the magnetic suture 500 from exiting the needle lumen 216 through the distal hole 214 of the needle body 208 when the enlarged distal terminus 246 is in the first position 248.

In some examples of these embodiments, the enlarged distal terminus 246 comprises a hook 338.

Also in some examples of these embodiments, the enlarged distal terminus 246 fills 50% or more of an area of the distal hole 214 of the needle body 208 when the enlarged distal terminus 246 is in the first position 248.

Again considering the grasper member 242 in more detail, in some embodiments the grasper member 242 is integral to the retriever body 224. In these embodiments, the retriever body 224 and the elongated proximal-to-intermediate portion 244 and the enlarged distal terminus 246 of the grasper member 242 are formed from a cut tube 354, as shown in FIGS. 100-103. In these embodiments, the retriever body 224 comprises a proximal cylindrical portion 356, the elongated proximal-to-intermediate portion 244 comprises an intermediate semi-cylindrical portion 358, and the enlarged distal terminus 246 comprises a distal cylindrical portion 360. The grasper magnet 254 is disposed adjacent the intermediate semi-cylindrical portion 358.

The grasper member 242 in which the retriever body 224 and the elongated proximal-to-intermediate portion 244 and the enlarged distal terminus 246 of the grasper member 242 are formed from a cut tube 354 can be provided in various configurations.

An exemplary configuration of the grasper member 242 is a rounded-distal-end single piece tube configuration, as shown in FIGS. 100-103. In this configuration, the retriever body 224 includes a retriever tube lumen 238 or a retriever body cavity 240 into which the magnet wire 256 fits. The enlarged distal terminus 246 has a rounded end 362. For assembly, the magnet wire 256 is inserted into the retriever tube lumen 238 or the retriever body cavity 240. Then the retriever body 224 is crimped onto the magnet wire 256. Alternatively, if the percent reduction of the crimp joint proves to be too high, then a grasper ferrule 268 may be used to reduce the depth of the crimp required to join the magnet wire 256 to the retriever body 224. In this case, the magnet wire 256 is inserted into the grasper ferrule 268, both are inserted into the retriever tube lumen 238 or retriever body cavity 240, and then the retriever body 224 is crimped onto the grasper ferrule 268 and the magnet wire 256. Optionally, the grasper ferrule 268 can be crimped onto the magnet wire 256 before both are inserted into the retriever tube lumen 238 or the retriever body cavity 240. Alternatively, the joint(s) may be made by welding, brazing, adhesive, or other approaches.

The grasper member 242 in which the retriever body 224 and the elongated proximal-to-intermediate portion 244 and the enlarged distal terminus 246 of the grasper member 242 are formed from a cut tube 354 also can be provided in other configurations.

A hook 338 may be incorporated into the enlarged distal terminus 246 of these embodiments too. Again, the hook can allow capture of a non-magnetic suture 600.

The resulting grasper member 242 in which the retriever body 224 and the elongated proximal-to-intermediate portion 244 and the enlarged distal terminus 246 of the grasper member 242 are formed from a cut tube 354 can then be used similarly as the grasper member 242 comprising the grasper wire 292 and the enlarged distal terminus 246 as described above.

Accordingly, in some of these embodiments, the enlarged distal terminus 246 is reversibly moveable between the first position 248 and the second position 250 based on translation of the enlarged distal terminus 246 from partially inside of the needle lumen 216 to entirely outside of the needle lumen 216 through the distal hole 214 of the needle body 208. In these embodiments, the enlarged distal terminus 246 has a size sufficiently small to allow contact between the grasper magnet 254 and a suture magnet 502 of a magnetic suture 500 attracted thereto when the enlarged distal terminus 246 is in the second position 250 and to allow a suture 504 of the magnetic suture 500 to pass when the enlarged distal terminus 246 is in the first position 248. Also, the enlarged distal terminus 246 has a size sufficiently large to block the suture magnet 502 of the magnetic suture 500 from exiting the needle lumen 216 through the distal hole 214 of the needle body 208 when the enlarged distal terminus 246 is in the first position 248.

In some examples of these embodiments, the enlarged distal terminus 246 comprises a hook 338.

Also in some examples of these embodiments, the enlarged distal terminus 246 fills 50% or more of an area of the distal hole 214 of the needle body 208 when the enlarged distal terminus 246 is in the first position 248.

In some embodiments, the magnet-assisted suture grasper 200 further comprises a proximal hub 220. The proximal hub 220 is located at a proximal end of the magnet-assisted suture grasper 200. The proximal hub 220 can be rigidly fixed to the retriever tube 224. The proximal hub 220 can have an open lumen 222.

As shown in FIGS. 1-17, in some embodiments, the magnet-assisted suture grasper 200 also comprises a lock mechanism 400 that can be reversibly engaged in a setting that prevents translation of the retriever body 224 within the needle lumen 216 in the first direction but not the second direction when the grasper member 242 is in the first position 248, wherein the spring 410 is a part of the lock mechanism 400. The lock mechanism 400 can be advantageous for bearing fully a tensile load applied to a magnetic suture 500 in the same direction.

In some of these embodiments, maintaining the lock mechanism 400 in the setting does not require energy input.

In some of these embodiments, the setting that prevents translation of the retriever body 224 within the needle lumen 216 in the first direction but not the second direction when the grasper member 242 is in the first position 248 is a first setting; and the lock mechanism 400 can be reversibly engaged in a second setting that prevents translation of the retriever body 224 within the needle lumen 216 in the first direction but not the second direction when the grasper member 242 is in the second position 250. In some examples of these embodiments, maintaining the lock mechanism 400 in the first setting or the second setting does not require energy input, i.e., no energy input is required to maintain the lock mechanism 400 in either the first setting or the second setting.

A magnet-assisted suture grasper 200 comprising such a lock mechanism 400, a retriever tube 230, and a tapered-ferrule grasper member 242 is shown in FIGS. 1-17, with reference to FIGS. 36-44. The magnet-assisted suture grasper 200 comprises an advancer assembly 402 comprising the retriever tube 224, an advancer frame 404 including proximal and distal guide bushings 408, an advancer pad 406, a return spring 410, a spring keeper 412, a cam spring 414, a drive cam 416, a lock cam 418, a cap bushing 419, a proximal hub 220, and an end effector 420 comprising the tapered-ferrule grasper member 242 and the magnet wire 256 with the magnet attached. In accordance with these examples, the end effector 420 is rigidly fixed to the retriever tube 230. The retriever tube 224 passes through the proximal and distal guide bushings 408 of the advancer frame 404, the spring keeper 412, the drive cam 416, and the lock cam 418, terminating within the body of the proximal hub 220. The proximal hub 220 and the advancer frame 404 are rigidly fixed to the retriever tube 224, and the advancer pad 406 is rigidly fixed to the advancer frame 404. The spring keeper 412 is not fixed within the advancer assembly 402, but is laterally constrained by a barrel 422 and nose cone 424, such that the spring keeper 412 has a longitudinal position that is fixed relative to these components. The entire advancer assembly 402 slides within the inner channel of the barrel 422 and nose cone 424, such that the return spring 410 compresses between the distal guide bushing 408 of the advancer frame 404 and the spring keeper 412 during this motion. The proximal and distal guide bushings 408 of the advancer frame 404 keep the components aligned axially and moving smoothly during sliding of the advancer assembly 402. The cap bushing 419 also assists in keeping the components axially aligned.

The magnet-assisted suture grasper 200 comprising the lock mechanism 400, the retriever tube 230, and the tapered-ferrule grasper member 242 can be operated as follows.

Initially, the advancer assembly 402 of the magnet-assisted suture grasper 200 is in a locked partially retracted position and the tapered-ferrule grasper member 242 is in the first position 248, as shown in FIGS. 45-49. The enlarged distal terminus 246 of the tapered-ferrule grasper member 242 extends partially from the distal hole 214 of the needle body 208. The tapered-ferrule grasper member 242 otherwise is disposed within the needle lumen 216 of the suture retrieval needle 202. The system is in a state of equilibrium, such that no external force is required to maintain this position.

To begin operation, the operator briefly pulls the advancer assembly 402 back with sufficient force to compress the return spring 410, until the advancer frame 404 engages the maximal boundary of a travel slot 426, to put the advancer assembly 402 in an unlocked fully retracted position, as shown in FIGS. 50-54. During this movement, the lock cam 418 engages the drive cam 416, and the lock cam teeth 432 are rotated into a valley in the crown of the drive cam 416. A continual application of external force, e.g., as applied by the operator, sufficient to overcome the elastic strain that has been loaded into the return spring 410, is required to maintain the advancer assembly 402 in this position.

To continue operation, the operator releases the advancer assembly 402 from this position. The return spring 410 then pushes the advancer assembly 402 forward, and the lock cam teeth 432 engage the channel ramps 442 in the barrel

422. The channel ramps 442 guide the teeth 432 and guide lugs 428 of the lock cam 418 into the linear guide channels 430.

The return spring 410 continues to push the advancer assembly 402 forward until the advancer frame 404 engages the minimum boundary of the travel slot 426, pushing the end effector 420 out of the cannula, as shown in FIGS. 55-59.

At this point, the advancer assembly 402 is in a locked extended position and the tapered ferrule grasper member 242 is in the second position 250. The system is in a state of equilibrium in this position, where no external force is required to maintain this position.

To continue operation, the operator pulls the advancer assembly 402 back, again with sufficient force to compress the return spring 410, to the unlocked fully retracted position, as shown in FIGS. 50-54. This pulls the end effector 420 into the needle lumen 216 and pushes the lock cam 418 into a relieved space 440 proximal to the locking features of the barrel 422. With the guide lugs 428 of the lock cam 418 now freed from the rotational constraint imposed by linear guide channels 430 of the barrel 422, the force exerted by the (preloaded) cam spring 414 is translated into a rotational movement of the lock cam 418 by way of mating lock cam teeth 432 and drive cam teeth 434 between the lock cam 418 and drive cam 416. Rotation of the lock cam 418 is halted when crests of the lock cam teeth 432 become nested in valleys between drive cam teeth 434. At this point, the advancer assembly 402 is again in the unlocked fully retracted position. Again, a continual application of external force sufficient to overcome the elastic strain that has been loaded into the return spring 410 is required to maintain the advancer assembly 402 in this position.

To continue operation, the operator releases the advancer assembly 402, which, in the absence of any external force, is pushed forward by the return spring 410, which had been compressed in the previous position. As the advancer assembly 402 moves forward, the lock cam teeth 432 slide along the lock ramps 436 of the barrel 422, resulting in simultaneous linear and rotational translation of the lock cam 418. This continues until the lock cam teeth 432 meet the lock stops 438 in the barrel 422, at which point the advancer assembly 402 becomes mechanically locked against any further movement in this direction. At this point, the advancer assembly 402 has returned to the locked partially retracted position and the tapered-ferrule grasper member 242 has returned to the first position 248, as shown in FIGS. 45-49. Again, the system is in a state of equilibrium in this position, such that no external force is required to maintain this position.

Figure 59:
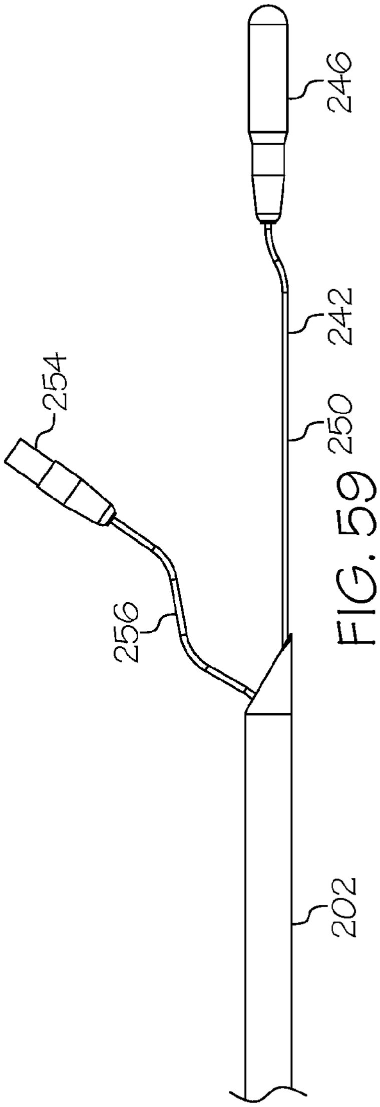
FIG. 59 is a side view of a distal portion of the magnet-assisted suture grasper of FIG. 55.
Figure 61:
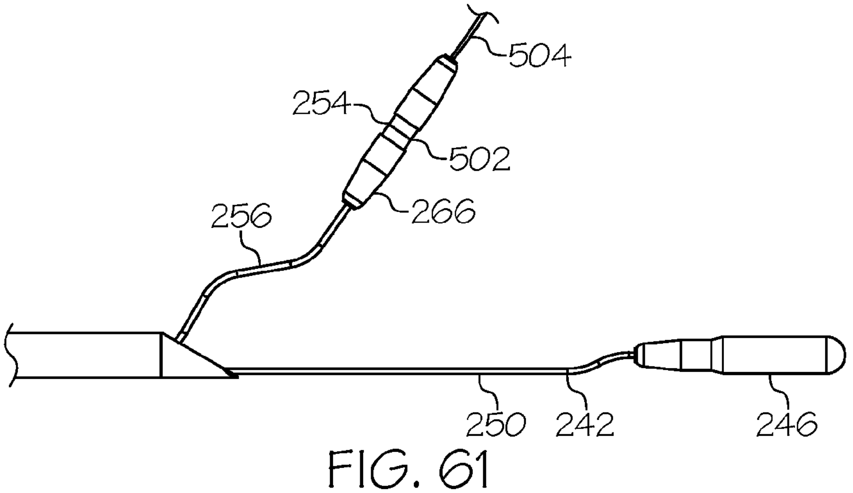
FIG. 61 is a side view of the distal portion of the magnet-assisted suture grasper of FIG. 60, in which the grasper magnet is attracting a magnetic suture and in contact with the magnetic suture.

The magnet-assisted suture grasper 200 comprising the lock mechanism 400, the retriever tube 230, and the tapered-ferrule grasper member 242 relies on magnetic attraction to establish a steady-state connection between the magnet-assisted suture grasper 200 and a magnetic suture 500 when in the locked extended position. With reference to FIGS. 59-61, the operator moves the advancer assembly 402 forward such that the advancer assembly 402 is in the locked extended position and the tapered-ferrule grasper member 242 is in the second position 250. The tapered-ferrule grasper member 242 and the grasper magnet 254 are brought near the suture magnet 502 of the magnetic suture 500. The tapered-ferrule grasper member 242 and the grasper magnet 254 do not need to be precisely aligned with the suture magnet 502, but only brought near so that the magnetic fields of the grasper magnet 254 and the suture magnet 502 may interact, allowing the magnetic moments to pull the southern pole of the suture magnet 502 into contact with the northern pole of the grasper magnet 254, thereby establishing a steady-state connection between the magnet-assisted suture grasper 200 and a magnetic suture 500.

Figure 62:
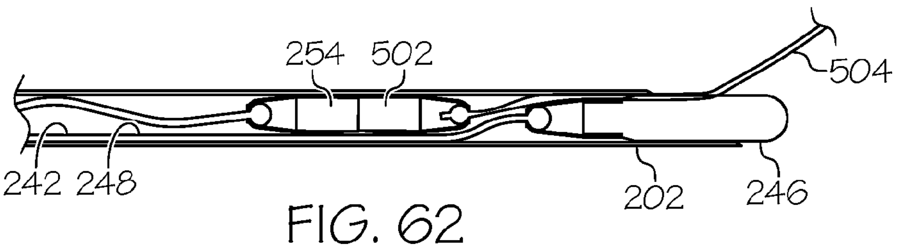
FIG. 62 is a side sectional view of a distal portion of the magnet-assisted suture grasper of FIG. 60, in which the advancer assembly is in the locked partially retracted position, the grasper member is in the first position, the grasper member is sequestering the grasper magnet within the suture retrieval needle, and the grasper magnet is attracting a magnetic suture and in contact with the magnetic suture, such that the magnetic suture has been captured within the needle lumen of the suture retrieval needle of the magnet-assisted suture grasper.

With reference to FIG. 62, the magnet-assisted suture grasper 200 can then accomplish mechanical capture of the magnetic suture 500 by moving from the locked extended position to unlocked fully retracted position as follows. After initial attraction, the operator briefly pulls the advancer assembly 402 back, returning the advancer assembly 402 to the unlocked fully retracted position. The steady-state connection between grasper magnet 254 and the suture magnet 502 allows the grasper magnet 254 to tow the magnetic suture 500 into the needle lumen 216. The length of the tapered-ferrule grasper member 242 is designed such that the enlarged distal terminus 246 at the end of the tapered-ferrule grasper member 242 maintains a distal position relative to the suture magnet 502 inside the needle lumen 216. This allows the enlarged distal terminus 246 to act as a plug, creating a physical blockage inside the needle lumen 216 by which the suture magnet 502 of the magnetic suture 500 cannot pass.

Figure 63:
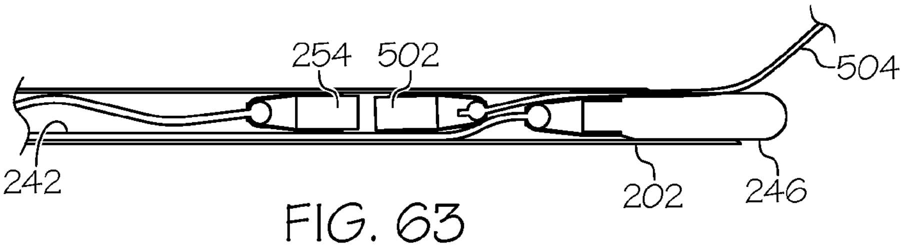
FIG. 63 is a side sectional view of a distal portion of the magnet-assisted suture grasper of FIG. 60, in which the advancer assembly is in the locked partially retracted position, the grasper member is in the first position, and the enlarged distal terminus of the grasper member is grasping the magnetic suture, such that the magnetic suture remains captured within the needle lumen of the suture retrieval needle of the magnet-assisted suture grasper.

With reference to FIG. 63, the magnet-assisted suture grasper 200 can then accomplish mechanical retention of the magnetic suture 500 in the locked partially retracted position as follows. The operator releases the advancer assembly 402, which is pushed forward by the return spring 410, moving the advancer assembly 402 from the unlocked fully retracted position, which is energetically unfavorable, to the locked partially retracted position, which is equipoised. The tapered-ferrule grasper member 242 is then in the first position 248. While the advancer assembly 402 remains in the locked partially retracted position, when the magnetic suture 500 is tensely loaded with a force that exceeds the attractive strength between the grasper magnet 254 and the suture magnet 502, the suture magnet 502 will be pulled away from grasper magnet 254, but will be stopped from exiting the needle lumen 216 by the tapered-ferrule grasper member 242. The tensile load applied to the magnetic suture 500 is thereby borne by the tapered-ferrule grasper member 242, which is translated through the tapered-ferrule grasper member 242 into the retriever tube 230 by way of a rigid joint between these two elements, and into the lock cam 418 by way of the proximal hub 220, which is also rigidly joined to the retriever tube 230. As the lock cam 418 is fixedly engaged with mechanical locking features of the barrel 422, this load is ultimately born by the interface between the lock cam 418 and the barrel 422. The ability of the device to resist tensile loading of the magnetic suture 500 is therefore limited by the tensile strength of these individual elements and the joints between them, as well as the shear strength of the lock cam teeth 432 and the lock stops 438 of the barrel 422. The material selections and cross-sectional areas of these elements ultimately define a much higher capacity for load bearing than that of the 3-0 suture this system is designed to work with, so that the suture itself becomes the limiting factor in the system. This is preferable to having another part of the system fail before the magnetic suture 500 because the surgeon is not artificially limited as to the amount of tension that can be applied by way of the magnetic suture 500. Another reason this is preferable is that when the system is overloaded and the magnetic suture 500 breaks, the suture magnet 502 of the magnetic suture 500 remains captured within the needle lumen 216, allowing for safe retrieval and disposal.

The magnet-assisted suture grasper 200 also is designed so that the retriever tube 230 runs centrally through all components. The retriever tube 230 is designed with an open retriever tube lumen 238 that runs the length of the retriever tube 230. The proximal hub 220 at the proximal end of the device is structured with an open lumen 222 that runs the entire length of the proximal hub 220. At the distal end, the needle body 208 is also lumenally patent. When assembled, the retriever tube lumen 238 opens to the open lumen 222 of the proximal hub 220 at the proximal end, and the needle lumen 216 of the needle body 208 at the distal end, creating a lumenal path that extends from end to end through the entire device.

Considering the lock mechanism 400 as shown in more detail, this lock mechanism 400 is formed between three components, the lock cam 418, the drive cam 416, and the barrel 422. The guide lugs 428 of the lock cam 418 and the guide lugs 444 of the drive cam 416 extend from the outer surface of their respective lock cam 418 and drive cam 416 and are disposed 180° apart. The barrel 422 features two guide channels 430, which are relieved into the inner surface and are also disposed 180° apart. When assembled, the guide lugs 428 of the lock cam 418 and the guide lugs 444 of the drive cam 416 fit into and slide within the guide channels 430. The lock cam 418 and drive cam 416 are assembled over the retriever tube 230, distal to the proximal hub 220 and proximal to the advancer frame 404. The cam spring 414 is placed between the advancer frame 404 and the drive cam 416. The cam spring 414 is pre-compressed during assembly so that it exerts a continual force upon the drive cam 416, acting to push the drive cam 416 towards the lock cam 418. The drive cam 416 features a crown of radially disposed V-shaped teeth 434. The lock cam 418 features right-triangle shaped teeth 432 with a matching ramp angle to that of the drive cam teeth 434. The barrel 422 features right angle teeth relieved into the inner surface of the barrel 422, proximal to the guide channels 430, also with ramp angles matching the lock and drive cams 416. The width of the lock cam teeth 432 is wider than the teeth 434 of the drive cam 416, so that the lock cam teeth 432 extend beyond the outer diameter of the drive cam teeth 434. The arrangement of teeth 432 on the lock cam 418 is such that when the lugs 428 of the lock cam 418 and the lugs 444 of the drive cam 416 are aligned, the apexes of the lock cam teeth 432 are slightly aft of the apexes of the nearest drive cam teeth 434. The arrangement of the barrel teeth is such that with the lock cam teeth 432 nested in the valley between drive cam teeth 434, the apexes of the lock cam teeth 432 sit slightly aft to the apex of the barrel teeth 434.

Operationally, the guide lugs 444 of the drive cam 416 remain within the guide channel 430 along all points of linear travel by the sliding assembly. As such, the drive cam 416 is always constrained against rotation about the neutral axis. The lock cam 418 is constrained in the same manner while the guide lugs 428 are positioned within the guide channel 430, but the lock cam 418 fully enters the relieved space 440 created by the barrel teeth 434 at the maximal extent of travel, i.e. the unlocked fully retracted position, which frees the guide lugs 428 of the lock cam 418 from guide channel 430, allowing the lock cam 418 to rotate about the neutral axis. When the guide lugs 428 of the lock cam 418 are freed from the constraints of the guide channel 430, the force exerted by the cam spring 414 drives the drive cam 416 towards the lock cam 418. The ramp angle of the mating lock cam teeth 432 and drive cam teeth 434 causes the lock cam 418 to slide along the drive cam tooth 434 towards the valley between drive cam teeth 434. As the drive cam 416 is rotationally constrained, but the lock cam 418 is not, this movement results in a counter-clockwise rotation of the lock cam 418 (approximately 45°). From this position, the sliding components of the assembly are moved back in the opposite direction, toward the locked extended position, which causes the lock cam teeth 432 to make contact with the lock ramps 436 of the barrel 422. Sliding contact of the lock cam teeth 432 with the lock ramps 436 causes a further counterclockwise rotation of the lock cam 418, until the teeth 432 make contact with the lock stops 438 (approximately 45°). This is the locked position. In this position, further movement from the unlocked fully retracted position to locked extended position is not possible. The lock is released by the sliding of the moving assembly back to unlocked fully retracted position, which drives the lock cam teeth 432 beyond the extends of the lock stops 438, at which point the lock cam 418 is rotationally driven further clockwise by the drive cam teeth 434. From this position, the sliding assembly can be driven to locked extended position. As the lock cam 418 advances linearly towards the locked extended position, the lock cam teeth 432 contact the channel ramps 442 in the barrel 422, and the sliding contact results in further counterclockwise rotation of the lock cam 418. At the lower apex of the channel ramps 442 are the guide channels 430, so that as the lock cam teeth 432 slide along the channel ramps 442 the guide lugs 428 are guided into the guide channels 430, allowing the entire sliding assembly to move towards the fully extended position. The rotational nature of this cycle is such that one lock/unlock cycle results in 180° translation of the lock cam 418, and two complete lock/unlock cycles returns the components to their original position (360° rotation). This allows for the lock/unlock cycle to be repeated indefinitely.

As will be appreciated, other lock mechanisms 400 can also be used with the magnet-assisted suture grasper 200. For example, the lock mechanism 400 can be a bolt-action lock mechanism in which a simple lever is moved within a J-shaped channel. An off-axis move into the short leg of the J-shaped channel secures the arm against the tensile force applied by the return spring. Another off-axis move repositions the lever into the long leg of the J-shaped channel to return to the original position. The lock mechanism 400 also can be a side button lock mechanism in which a U-shaped flat spring floats within a moving member, and a spring action of the U-shaped flat spring causes the spring to engage with a lip in the moving member to lock the device in an extended position. The U-shaped spring protrudes from the side of the device, forming a button. Pressing the button disengages the U-shaped spring from the lip, allowing a return spring to return the device to a retracted position. The lock mechanism 400 also can be a crossing-path lock mechanism, including a metal pin fixed in a floating carriage. The carriage is longitudinally fixed, but freely rotates, which allows the pin to follow grooves cut in a medial member. The grooves create a crossing path that locks and unlocks the device as the medial member is slidingly translated. The lock mechanism 400 also can be a twist lock mechanism featuring a medial sleeve with a helical cut. When the sleeve is rotated, the helical surface acts upon a rotationally fixed cam follower to create linear motion. The lock mechanism 400 also can be a detent mechanism. Other suitable lock mechanisms 400 also can be used.

As noted above, the enlarged distal terminus 246 of the grasper member 242 comprises a blunt distal end 252, extends partially from the distal hole 214 of the needle body 208 when the grasper member 242 is in the first position 248, and extends entirely beyond the distal hole 214 of the needle body 208 when the grasper member 242 is in the second position 250. Also as noted, the spring 410 allows the grasper member 242 to move reversibly further in the second direction from the first position 248 upon pushing contact in the second direction at the enlarged distal terminus 246 of the grasper member 242 and returns the grasper member 242 to the first position 248 upon cessation of the pushing contact. The grasper member 242 thus can function as an atraumatic probe in a similar manner to a Veress needle.

The enlarged distal terminus 246 operates between three primary positions, (1) "tip protected," (2) "tip exposed," and (3) "grasper extended."

Figure 64:
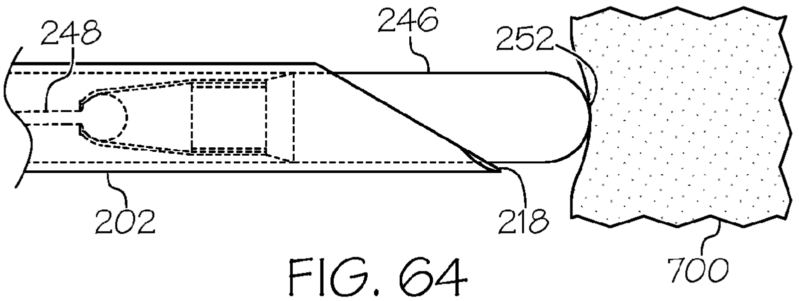
FIG. 64 is a side view of a distal portion of the magnet-assisted suture grasper of FIG. 60, in which the advancer assembly is in the locked partially retracted position, the grasper member is in the first position, and the enlarged distal terminus of the grasper member is in contact with a tissue of a patient. While the advancer assembly is in the locked partially retracted position, the grasper member, including the enlarged distal terminus, cannot be advanced distally from the suture retrieval needle, but can be pushed proximally into the suture retrieval needle by the tissue.

The magnet-assisted suture grasper 200 is in the tip protected position when the grasper member 242 is in the first position 248. For the magnet-assisted suture grasper 200 comprising the lock mechanism 400, the retriever tube 230, and the tapered-ferrule grasper member 242 described above, this corresponds to the locked partially retracted position, as shown in FIGS. 45-49. In this position the spring 410 is partially compressed. The blunt distal end 252 of the enlarged distal terminus 246 extends from the distal end of the suture retrieval needle 202, protecting tissue from the distal end of the suture retrieval needle 202, as shown in FIG. 64. The spring 410 is configured so that as the magnet-assisted suture grasper 200 is pushed against a tissue 700, the enlarged distal terminus 246 makes contact first, the spring 410 is compressed further, and the enlarged distal terminus 246 translates proximally into the needle lumen 216 of the suture retrieval needle 202. Unintentional contact can be ceased before the enlarged distal terminus 246 has translated deeply enough to expose the distal end 206 of the suture retrieval needle 202, thus preventing injury. Upon ceasing unintentional contact, the spring 410 releases, returning the enlarged distal terminus 246 to the tip-protected position.

Figure 65:
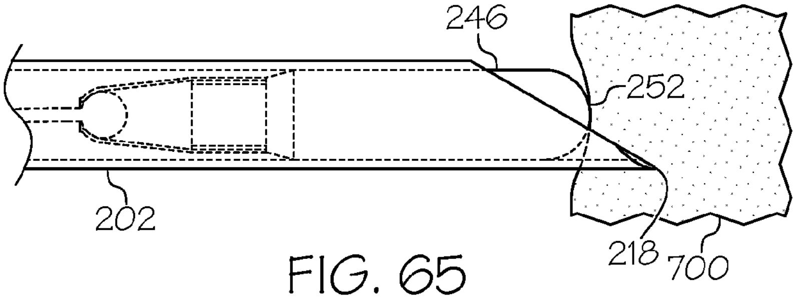
FIG. 65 is a side view of a distal portion of the magnet-assisted suture grasper of FIG. 64. As the suture retrieval needle is initially advanced into the tissue, the grasper member, including the enlarged distal terminus, is pushed proximally into the suture retrieval needle by the tissue.
Figure 66:
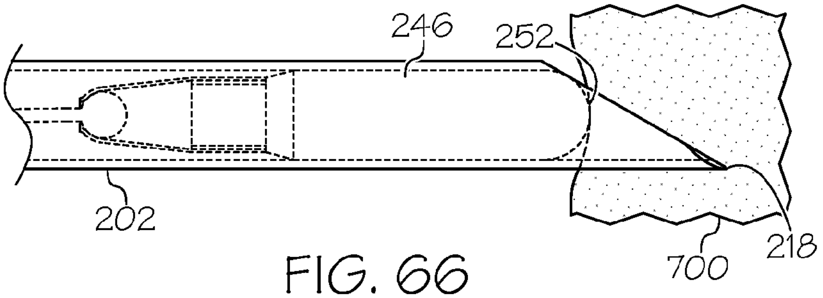
FIG. 66 is a side view of a distal portion of the magnet-assisted suture grasper of FIG. 64. As the suture retrieval needle is advanced further into the tissue, the grasper member, including the enlarged distal terminus, is pushed proximally further into the suture retrieval needle by the tissue.
Figure 67:
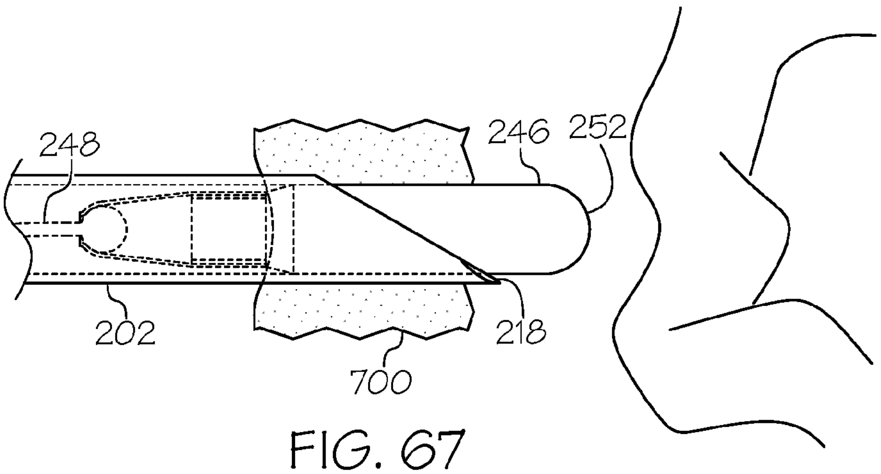
FIG. 67 is a side view of a distal portion of the magnet-assisted suture grasper of FIG. 64. Once the suture retrieval needle has passed entirely through the tissue, the grasper member, including the enlarged distal terminus, advances distally from the suture retrieval needle and returns to the first position.

For intentional contact, the magnet-assisted suture grasper 200 can be pushed further until the distal end 206 of the suture retrieval needle 202 has pierced the tissue 700, as shown in FIGS. 65-67. This transitions the enlarged distal terminus 246 to the tip-exposed position, as shown in FIG. 65 and FIG. 66. As the spring 410 is further compressed, the enlarged distal terminus 246 translates more deeply into the needle lumen 216 of the suture retrieval needle 202, exposing the distal end 206 of the suture retrieval needle 202. Once the enlarged distal terminus 246 is no longer in pushing contact with the tissue 700, the spring 410 releases, returning the enlarged distal terminus 246 to the tip-protected position, with the blunt distal end 252 of the enlarged distal terminus 246 again protruding from the distal end 206 of the suture retrieval needle 202, as shown in FIG. 67.

The magnet-assisted suture grasper 200 is in the grasper-extended position when the grasper member 242 is in the second position 250. For the magnet-assisted suture grasper 200 comprising the lock mechanism 400, the retriever tube 230, and the tapered-ferrule grasper member 242 described above, this corresponds to the locked extended position, as shown in FIGS. 55-59. As discussed above, translation of the grasper member 242 from the first position 248 to the second position 250 exposes the grasper magnet 254 and allows contact between the grasper magnet 254 and a magnetic suture 500 attracted thereto.

In some embodiments, the spring 410 of the magnet-assisted suture grasper 200 is not part of a lock mechanism 400. As noted above, the grasper member 242 functions as a spring-loaded atraumatic probe in a similar manner to a Veress needle. The spring 410 can be configured within the magnet-assisted suture grasper 200 similarly to the configuration of a spring of a Veress needle, without need for the spring 410 to be part of a lock mechanism 400, and without need for the magnet-assisted suture grasper 200 to include a lock mechanism 400.

In some embodiments, the magnet-assisted suture grasper 200 can be made further comprising a stabilizer tube (not shown). In accordance with these embodiments, the retriever body 224 passes through a lumen of the stabilizer tube, and is rigidly fixed to the stabilizer tube.

A system for passing a magnetic suture 500 also is disclosed. The system comprises the magnet-assisted suture grasper 200. The system also comprises a magnetic suture 500 comprising a suture magnet 502 and a suture 504 extending from the suture magnet 502.

The magnet-assisted suture grasper disclosed herein can be used for passing a magnetic suture that includes a suture magnet at an end of the suture. Such a magnetic suture can be made, for example, as described in U.S. Pub. No. 2021/0059667. The magnet-assisted suture grasper disclosed herein also can be used for passing a magnetic suture that is magnetic based on including a magnetic metal within the suture.

The magnet-assisted suture grasper disclosed herein may be useful in procedures including, among others: (1) Inguinal hernia repair through high ligation of the patent processus vaginalis as described above; (2) Laparoscopic port closure (typical suture size 2-0 and larger); (3) Microsurgery (typical suture size 7-0 and smaller); (4) General surgery (typical suture size 2-0 to 0); and (5) Orthopedic surgery (typical suture size 0 and larger).

The magnet-assisted suture grasper also may be modified for use in ultrasound-guided surgical techniques. The magnet-assisted suture grasper would be modified by making the distal end of the suture retrieval needle echogenic. This could be done, for example, by applying an echogenic treatment at the distal tip of the suture retrieval needle. The modified magnet-assisted suture grasper would then be used with a hypodermic needle for introducing a suture wherein the hypodermic needle also is echogenic at its distal end. Optionally the magnets of the magnet-assisted suture grasper and the magnetic suture and/or the magnet ferrules that attach the magnets to the wire of the magnet-assisted suture grasper and to the suture also may be made echogenic, for example by applying an echogenic treatment to the magnets and/or the magnet ferrules.

Use of the modified magnet-assisted suture grasper in ultrasound-guided surgical techniques could result in reductions in operative time and complexity by eliminating the need for suction equipment. Suction equipment currently is needed to pass the suture through the needle.

The modified magnet-assisted suture grasper also may allow an alternative technique whereby the suture is dropped off and retrieved from inside the abdominal cavity. This would allow the repair to be completed entirely through a single needle-access point, which would provide improved cosmesis, and could result in less post-operative pain. Under the current laparoscopic approach (termed the PEAR/PIRS technique), the needle is introduced through the skin and directed medial around the defect, exiting inferior to the defect through the peritoneum into the abdominal cavity. Drop-off and retrieval of the suture occurs in this space inside the abdominal cavity. This is not currently possible under ultrasonic guidance because the suture is not echogenic, so the surgeon would have to retrieve the suture from inside the abdominal cavity completely blind. This would be nearly impossible with the current state of suture passer technology (i.e., snares, graspers, etc.). In contrast, the modified magnet-assisted suture grasper may allow this to work, especially if the needle points and ferrules are echogenic.

The magnet-assisted suture grasper described herein could be integrated as end-of-arm tooling for robot-assisted surgery or into the end of an endoscope for direct manipulation of a suture with the endoscope.

While this invention has been described in conjunction with the specific embodiments outlined above, it is evident that many alternatives, modifications and variations will be apparent to those skilled in the art. Accordingly, the preferred embodiments of the invention as set forth above are intended to be illustrative, not limiting. Various changes may be made without departing from the spirit and scope of the invention.

CLAUSES

1. A magnet-assisted suture grasper for grasping a magnetic suture comprising:
(a) a suture retrieval needle comprising a proximal end, a distal end, and a needle body extending therebetween, the needle body defining a needle body axis between the proximal and distal ends of the suture retrieval needle, the needle body having a proximal hole, a distal hole, and a needle lumen extending therebetween along the needle body axis;
(b) a retriever body partially disposed within the needle lumen and translatable therein along the needle body axis;
(c) a grasper member comprising an elongated proximal-to-intermediate portion and an enlarged distal terminus, the grasper member extending distally from the retriever body and being reversibly moveable with respect to the needle lumen between a first position and a second position, the enlarged distal terminus of the grasper member comprising a blunt distal end and extending partially from the distal hole of the needle body when the grasper member is in the first position and extending entirely beyond the distal hole of the needle body when the grasper member is in the second position;
(d) a grasper magnet being disposed adjacent the elongated proximal-to-intermediate portion of the grasper member, the magnet-assisted suture grasper sequestering the grasper magnet within the needle lumen when the grasper member is in the first position and exposing the grasper magnet from the needle lumen when the grasper member is in the second position; and
(e) a spring, wherein:
the enlarged distal terminus of the grasper member extends further distally than the grasper magnet;
translation of the retriever body within the needle lumen in a first direction along the needle body axis causes the grasper member to move from the first position to the second position, thereby exposing the grasper magnet and allowing contact between the grasper magnet and a magnetic suture attracted thereto;
translation of the retriever body within the needle lumen in a second direction opposite the first direction along the needle body axis causes the grasper member to move from the second position to the first position, thereby sequestering the grasper magnet and grasping the magnetic suture within the needle lumen; and
the spring allows the grasper member to move reversibly further in the second direction from the first position upon pushing contact in the second direction at the enlarged distal terminus of the grasper member and returns the grasper member to the first position upon cessation of the pushing contact.
2. The magnet-assisted suture grasper according to clause 1, wherein the suture retrieval needle is a hypodermic needle.
3. The magnet-assisted suture grasper according to clause 1 or clause 2, wherein the suture retrieval needle is straight, the needle body axis thereby being straight.
4. The magnet-assisted suture grasper according to clause 1 or clause 2, wherein the suture retrieval needle is curved, the needle body axis thereby being curved.
5. The magnet-assisted suture grasper according to any one of clauses 1 to 4, wherein the suture retrieval needle has a sharp tip.
6. The magnet-assisted suture grasper according to any one of clauses 1 to 5, wherein magnet-assisted suture grasper further comprises a proximal hub.
7. The magnet-assisted suture grasper according to any one of clauses 1 to 6, wherein:
the retriever body comprises a proximal end, a distal end, and a retriever tube extending therebetween;
the retriever tube defines a retriever tube axis between the proximal and distal ends of the retriever body;
the retriever tube has a proximal hole, a distal hole, and a retriever tube lumen extending therebetween along the retriever tube axis; and
the proximal hole of the retriever tube is in fluid communication with the distal hole of the needle body through the retriever tube lumen and the needle lumen.
8. The magnet-assisted suture grasper according to any one of clauses 1 to 6, wherein the retriever body comprises a proximal end, a distal end, a distal hole, and a retriever tube cavity extending within the retriever tube from the distal hole of the retriever tube.
9. The magnet-assisted suture grasper according to any one of clauses 1 to 8, wherein translation of the retriever body within the needle lumen is limited to a straight path as the translation of the retriever body causes the grasper member to move between the first and second positions.
10. The magnet-assisted suture grasper according to any one of clauses 1 to 9, wherein the grasper member is more flexible than the needle body.
11. The magnet-assisted suture grasper according to any one of clauses 1 to 10, wherein:
the elongated proximal-to-intermediate portion of the grasper member comprises a grasper wire having a proximal end and a distal end;
the grasper wire is fixedly disposed within the retriever body and extends distally therefrom;
the enlarged distal terminus extends distally from the distal end of the grasper wire and is reversibly moveable between the first position and the second position; and
the grasper magnet is disposed adjacent the grasper wire.
12. The magnet-assisted suture grasper according to clause 11, wherein:
the enlarged distal terminus is reversibly moveable between the first position and the second position based on translation of the enlarged distal terminus from partially inside of the needle lumen to entirely outside of the needle lumen through the distal hole of the needle body; and
the enlarged distal terminus has a size sufficiently small to allow contact between the grasper magnet and a suture magnet of a magnetic suture attracted thereto when the enlarged distal terminus is in the second position and to allow a suture of the magnetic suture to pass when the enlarged distal terminus is in the first position, and sufficiently large to block the suture magnet of the magnetic suture from exiting the needle lumen through the distal hole of the needle body when the enlarged distal terminus is in the first position.

13. The magnet-assisted suture grasper according to clause 11 or clause 12, wherein:

the grasper wire is formed from a round wire; and the enlarged distal terminus is fixedly attached to the grasper wire.

14. The magnet-assisted suture grasper according to clause 11 or clause 12, wherein:

the grasper wire and the enlarged distal terminus are formed from a flat wire having a rectangular cross-section;

the enlarged distal terminus comprises opposing first and second portions of the flat wire that have been folded inwardly toward each other, thereby forming the enlarged distal terminus; and the enlarged distal terminus is integral to the grasper wire.

15. The magnet-assisted suture grasper according to any one of clauses 11 to 14, wherein the enlarged distal terminus comprises a hook.

16. The magnet-assisted suture grasper according to any one of clauses 11 to 15, wherein the enlarged distal terminus fills 50% or more of an area of the distal hole of the needle body when the enlarged distal terminus is in the first position.

17. The magnet-assisted suture grasper according to any one of clauses 1 to 10, wherein:

the elongated proximal-to-intermediate portion and the enlarged distal terminus are formed from a cut tube;

the elongated proximal-to-intermediate portion comprises a proximal cylindrical portion and an intermediate semi-cylindrical portion;

the enlarged distal terminus comprises a distal cylindrical portion;

the proximal cylindrical portion is fixedly attached to the retriever tube and extends distally therefrom; and the grasper magnet is disposed adjacent the intermediate semi-cylindrical portion.

18. The magnet-assisted suture grasper according to clause 17, wherein:

the enlarged distal terminus is reversibly moveable between the first position and the second position based on translation of the enlarged distal terminus from partially inside of the needle lumen to entirely outside of the needle lumen through the distal hole of the needle body; and the enlarged distal terminus has a size sufficiently small to allow contact between the grasper magnet and a suture magnet of a magnetic suture attracted thereto when the enlarged distal terminus is in the second position and to allow a suture of the magnetic suture to pass when the enlarged distal terminus is in the first position, and sufficiently large to block the suture magnet of the magnetic suture from exiting the needle lumen through the distal hole of the needle body when the enlarged distal terminus is in the first position.

19. The magnet-assisted suture grasper according to clause 17 or clause 18, wherein the enlarged distal terminus comprises a hook.

20. The magnet-assisted suture grasper according to any one of clauses 17 to 19, wherein the enlarged distal terminus fills 50% or more of an area of the distal hole of the needle body when the enlarged distal terminus is in the first position.

21. The magnet-assisted suture grasper according to any one of clauses 1 to 10, wherein:

the grasper member is integral to the retriever body;

the retriever body and the elongated proximal-to-intermediate portion and the enlarged distal terminus of the grasper member are formed from a cut tube;

the retriever body comprises a proximal cylindrical portion, the elongated proximal-to-intermediate portion comprises an intermediate semi-cylindrical portion, and the enlarged distal terminus comprises a distal cylindrical portion; and the grasper magnet is disposed adjacent the intermediate semi-cylindrical portion.

22. The magnet-assisted suture grasper according to clause 21, wherein:

the enlarged distal terminus is reversibly moveable between the first position and the second position based on translation of the enlarged distal terminus from partially inside of the needle lumen to entirely outside of the needle lumen through the distal hole of the needle body; and the enlarged distal terminus has a size sufficiently small to allow contact between the grasper magnet and a suture magnet of a magnetic suture attracted thereto when the enlarged distal terminus is in the second position and to allow a suture of the magnetic suture to pass when the enlarged distal terminus is in the first position, and sufficiently large to block the suture magnet of the magnetic suture from exiting the needle lumen through the distal hole of the needle body when the enlarged distal terminus is in the first position.

23. The magnet-assisted suture grasper according to clause 21 or clause 22, wherein the enlarged distal terminus comprises a hook.

24. The magnet-assisted suture grasper according to any one of clause 21 to 23, wherein the enlarged distal terminus fills 50% or more of an area of the distal hole of the needle body when the enlarged distal terminus is in the first position.

25. The magnet-assisted suture grasper according to any one of clauses 1 to 24, further comprising a magnet wire having a proximal portion and a distal portion, wherein the proximal portion of the magnet wire is fixedly disposed within the retriever body and the grasper magnet is fixedly attached to the distal portion of the magnet wire, either directly or indirectly.

26. The magnet-assisted suture grasper according to clause 25, further comprising a grasper ferrule comprising a proximal end, a distal end, and a ferrule body extending therebetween, the ferrule body having a proximal hole, a distal hole, and a ferrule lumen extending therebetween, wherein:

the grasper ferrule is fixedly disposed within the retriever body; and the magnet wire extends distally from the retriever body.

27. The magnet-assisted suture grasper according to clause 26, wherein:

the grasper ferrule has been crimped onto the grasper member and the magnet wire with the elongated proximal-to-intermediate portion of the grasper member and the proximal portion of the magnet wire being disposed within the ferrule lumen of the grasper ferrule; and the retriever body has been crimped onto the grasper ferrule with the grasper ferrule, the elongated proximal-to-intermediate portion of the grasper member, and the proximal portion of the magnet wire being disposed within the retriever body.

28. The magnet-assisted suture grasper according to clause 26, wherein the retriever body has been crimped onto the grasper ferrule, the elongated proximal-to-intermediate portion of the grasper member, and the proximal portion of the magnet wire, with the grasper ferrule, the elongated proximal-to-intermediate portion of the grasper member, and the proximal portion of the magnet wire being disposed within the retriever body, and with the elongated proximal-to-intermediate portion of the grasper member and the proximal portion of the magnet wire being disposed adjacent the grasper ferrule and not within the ferrule lumen of the grasper ferrule.

29. The magnet-assisted suture grasper according to any one of clauses 25 to 29, wherein the magnet wire further comprises a magnet wire distal terminus at the distal end of the magnet wire, the magnet-assisted suture grasper further comprises a magnet ferrule fixedly attached to the magnet wire distal terminus, and the grasper magnet is fixedly attached to the magnet ferrule.

30. The magnet-assisted suture grasper according to any one of clauses 1 to 29, further comprising a lock mechanism that can be reversibly engaged in a setting that prevents translation of the retriever body within the needle lumen in the first direction but not the second direction when the grasper member is in the first position, wherein the spring is a part of the lock mechanism.

31. The magnet-assisted suture grasper according to clause 30, wherein maintaining the lock mechanism in the setting does not require energy input.

32. The magnet-assisted suture grasper according to clause 30 or clause 31, wherein:

the setting that prevents translation of the retriever body within the needle lumen in the first direction but not the second direction when the grasper member is in the first position is a first setting; and the lock mechanism can be reversibly engaged in a second setting that prevents translation of the retriever body within the needle lumen in the first direction but not the second direction when the grasper member is in the second position.

33. The magnet-assisted suture grasper according to clause 32, wherein maintaining the lock mechanism in the first setting or the second setting does not require energy input.

34. A system for passing a magnetic suture comprising:

the magnet-assisted suture grasper of any one of clauses 1 to 33; and a magnetic suture comprising a suture magnet and a suture extending from the suture magnet.

What is claimed is:

1. A magnet-assisted suture grasper for grasping a magnetic suture comprising:

(a) a suture retrieval needle comprising a proximal end, a distal end, and a needle body extending therebetween, the needle body defining a needle body axis between the proximal and distal ends of the suture retrieval needle, the needle body having a proximal hole, a distal hole, and a needle lumen extending therebetween along the needle body axis;

(b) a retriever body partially disposed within the needle lumen and translatable therein along the needle body axis;

(c) a grasper member comprising an elongated proximal-to-intermediate portion and an enlarged distal terminus, the grasper member extending distally from the retriever body and being reversibly moveable with respect to the needle lumen between a first position and a second position, the enlarged distal terminus of the grasper member comprising a blunt distal end and extending partially from the distal hole of the needle body when the grasper member is in the first position and extending entirely beyond the distal hole of the needle body when the grasper member is in the second position;

(d) a grasper magnet being disposed adjacent the elongated proximal-to-intermediate portion of the grasper member, the magnet-assisted suture grasper sequestering the grasper magnet within the needle lumen when the grasper member is in the first position and exposing the grasper magnet from the needle lumen when the grasper member is in the second position; and (e) a spring, wherein:

the enlarged distal terminus of the grasper member extends further distally than the grasper magnet;

translation of the retriever body within the needle lumen in a first direction along the needle body axis causes the grasper member to move from the first position to the second position, thereby exposing the grasper magnet and allowing contact between the grasper magnet and a magnetic suture attracted thereto;

translation of the retriever body within the needle lumen in a second direction opposite the first direction along the needle body axis causes the grasper member to move from the second position to the first position, thereby sequestering the grasper magnet and grasping the magnetic suture within the needle lumen; and the spring allows the grasper member to move reversibly further in the second direction from the first position upon pushing contact in the second direction at the enlarged distal terminus of the grasper member and returns the grasper member to the first position upon cessation of the pushing contact.

2. The magnet-assisted suture grasper according to claim 1, wherein the suture retrieval needle is straight, the needle body axis thereby being straight.

3. The magnet-assisted suture grasper according to claim 1, wherein the suture retrieval needle is curved, the needle body axis thereby being curved.

4. The magnet-assisted suture grasper according to claim 1, wherein the suture retrieval needle has a sharp tip.

5. The magnet-assisted suture grasper according to claim 1, wherein magnet-assisted suture grasper further comprises a proximal hub.

6. The magnet-assisted suture grasper according to claim 1, wherein:

the retriever body comprises a proximal end, a distal end, and a retriever tube extending therebetween;

the retriever tube defines a retriever tube axis between the proximal and distal ends of the retriever body;

the retriever tube has a proximal hole, a distal hole, and a retriever tube lumen extending therebetween along the retriever tube axis; and the proximal hole of the retriever tube is in fluid communication with the distal hole of the needle body through the retriever tube lumen and the needle lumen.

7. The magnet-assisted suture grasper according to claim 1, wherein the retriever body comprises a proximal end, a distal end, a distal hole, and a retriever body cavity extending within the retriever body from the distal hole of the retriever body.

8. The magnet-assisted suture grasper according to claim 1, wherein translation of the retriever body within the needle lumen is limited to a straight path as the translation of the retriever body causes the grasper member to move between the first and second positions.

9. The magnet-assisted suture grasper according to claim 1, wherein the grasper member is more flexible than the needle body.

10. The magnet-assisted suture grasper according to claim 1, wherein:

the elongated proximal-to-intermediate portion of the grasper member comprises a grasper wire having a proximal end and a distal end;

the grasper wire is fixedly disposed within the retriever body and extends distally therefrom;

the enlarged distal terminus extends distally from the distal end of the grasper wire and is reversibly moveable between the first position and the second position; and the grasper magnet is disposed adjacent the grasper wire.

11. The magnet-assisted suture grasper according to claim 10, wherein:

the enlarged distal terminus is reversibly moveable between the first position and the second position based on translation of the enlarged distal terminus from partially inside of the needle lumen to entirely outside of the needle lumen through the distal hole of the needle body; and the enlarged distal terminus has a size sufficiently small to allow contact between the grasper magnet and a suture magnet of a magnetic suture attracted thereto when the enlarged distal terminus is in the second position and to allow a suture of the magnetic suture to pass when the enlarged distal terminus is in the first position, and sufficiently large to block the suture magnet of the magnetic suture from exiting the needle lumen through the distal hole of the needle body when the enlarged distal terminus is in the first position.

12. The magnet-assisted suture grasper according to claim 10, wherein:

the grasper wire is formed from a round wire; and the enlarged distal terminus is fixedly attached to the grasper wire.

13. The magnet-assisted suture grasper according to claim 10, wherein:

the grasper wire and the enlarged distal terminus are formed from a flat wire having a rectangular cross-section;

the enlarged distal terminus comprises opposing first and second portions of the flat wire that have been folded inwardly toward each other, thereby forming the enlarged distal terminus; and the enlarged distal terminus is integral to the grasper wire.

14. The magnet-assisted suture grasper according to claim 10, wherein the enlarged distal terminus comprises a hook.

15. The magnet-assisted suture grasper according to claim 10, wherein the enlarged distal terminus fills 50% or more of an area of the distal hole of the needle body when the enlarged distal terminus is in the first position.

16. The magnet-assisted suture grasper according to claim 1, wherein:

the elongated proximal-to-intermediate portion and the enlarged distal terminus are formed from a cut tube;

the elongated proximal-to-intermediate portion comprises a proximal cylindrical portion and an intermediate semi-cylindrical portion;

the enlarged distal terminus comprises a distal cylindrical portion;

the proximal cylindrical portion is fixedly attached to the retriever tube and extends distally therefrom; and the grasper magnet is disposed adjacent the intermediate semi-cylindrical portion.

17. The magnet-assisted suture grasper according to claim 1, wherein:

the grasper member is integral to the retriever body;

the retriever body and the elongated proximal-to-intermediate portion and the enlarged distal terminus of the grasper member are formed from a cut tube;

the retriever body comprises a proximal cylindrical portion, the elongated proximal-to-intermediate portion comprises an intermediate semi-cylindrical portion, and the enlarged distal terminus comprises a distal cylindrical portion; and the grasper magnet is disposed adjacent the intermediate semi-cylindrical portion.

18. The magnet-assisted suture grasper according to claim 1, further comprising a magnet wire having a proximal portion and a distal portion, wherein the proximal portion of the magnet wire is fixedly disposed within the retriever body and the grasper magnet is fixedly attached to the distal portion of the magnet wire, either directly or indirectly.

19. The magnet-assisted suture grasper according to claim 18, further comprising a grasper ferrule comprising a proximal end, a distal end, and a ferrule body extending therebetween, the ferrule body having a proximal hole, a distal hole, and a ferrule lumen extending therebetween, wherein:

the grasper ferrule is fixedly disposed within the retriever body; and the magnet wire extends distally from the retriever body.

20. The magnet-assisted suture grasper according to claim 19, wherein:

the grasper ferrule has been crimped onto the grasper member and the magnet wire with the elongated proximal-to-intermediate portion of the grasper member and the proximal portion of the magnet wire being disposed within the ferrule lumen of the grasper ferrule; and the retriever body has been crimped onto the grasper ferrule with the grasper ferrule, the elongated proximal-to-intermediate portion of the grasper member, and the proximal portion of the magnet wire being disposed within the retriever body.

21. The magnet-assisted suture grasper according to claim 19, wherein:

the retriever body has been crimped onto the grasper ferrule, the elongated proximal-to-intermediate portion of the grasper member, and the proximal portion of the magnet wire, with the grasper ferrule, the elongated proximal-to-intermediate portion of the grasper member, and the proximal portion of the magnet wire being disposed within the retriever body, and with the elongated proximal-to-intermediate portion of the grasper member and the proximal portion of the magnet wire being disposed adjacent the grasper ferrule and not within the ferrule lumen of the grasper ferrule.

22. The magnet-assisted suture grasper according to claim 1, further comprising a lock mechanism that can be reversibly engaged in a setting that prevents translation of the retriever body within the needle lumen in the first direction but not the second direction when the grasper member is in the first position, wherein the spring is a part of the lock mechanism.

* * * * *